(12) United States Patent
Gellman et al.

(10) Patent No.: US 9,284,362 B2
(45) Date of Patent: Mar. 15, 2016

(54) α/β-PEPTIDE MIMICS OF Z-DOMAIN PEPTIDES

(71) Applicant: Wisconsin Alumni Research Foundation, Madison, WI (US)

(72) Inventors: Samuel H. Gellman, Madison, WI (US); James W. Checco, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/602,734

(22) Filed: Jan. 22, 2015

(65) Prior Publication Data
US 2015/0203555 A1   Jul. 23, 2015

Related U.S. Application Data

(60) Provisional application No. 61/930,449, filed on Jan. 22, 2014.

(51) Int. Cl.
| | |
|---|---|
| C07K 14/525 | (2006.01) |
| C07K 16/22 | (2006.01) |
| C07K 16/42 | (2006.01) |
| C07K 14/52 | (2006.01) |
| C07K 14/31 | (2006.01) |

(52) U.S. Cl.
CPC .............. *C07K 14/525* (2013.01); *C07K 14/31* (2013.01); *C07K 14/52* (2013.01); *C07K 16/22* (2013.01); *C07K 16/4283* (2013.01); *C07K 2317/73* (2013.01); *C07K 2317/76* (2013.01); *C07K 2317/92* (2013.01); *C07K 2318/20* (2013.01); *C12Y 207/10001* (2013.01)

(58) Field of Classification Search
CPC ................................................... C07K 14/525
See application file for complete search history.

(56) References Cited

U.S. PATENT DOCUMENTS

| | | |
|---|---|---|
| 2008/0176278 A1 | 7/2008 | Syud et al. |
| 2010/0099185 A1 | 4/2010 | Horne et al. |
| 2013/0129752 A1 | 5/2013 | Peer et al. |

OTHER PUBLICATIONS

Ahlgren, S. et al., Targeting of HER2-Expressing Tumors using $^{111}$In-ABY-025, a Second-Generation Affibody Molecule with a Fundamentally Reengineered Scaffold, *J. Nucl. Med.* 2010, 51, 1131-1138.
Baum, R. et al., Molecular Imaging of HER2-Expressing Malignant Tumors in Breast Cancer Patients Using Synthetic [111]In- or $^{68}$Ga-labeled Affibody Molecules, *J. Nucl. Med.* 2010, 51, 892.
Binz, H. et al., Engineering novel binding proteins from nonimmunoglobulin domains, *Nat. Biotech.* 2005, 23, 1257.
Braisted, A. et al., Minimizing a binding domain from Protein A, *Proc. Natl. Acad. Sci. U.S.A.* 1996, 93, 5688-5692.
Deisenhofer, J., Chrystallographic Refinement and Atomic Models of a Human Fc Fragment and Its Complex with Fragrant B of Protein A from *Staphyloccocus aureus* at 2.9- and 2.8-Å Resolution, *Biochemistry* 1981, 20, 2361.
Eigenbrot, G. at al., Structural basis for high-affinity HER2 receptor binding by an engineered protein, *Proc. Natl. Acad. Sci. U.S.A* 2010, 107, 15039-15044.
Eklund, M. et al., Anti-idiotypic protein domains selected from protein A-based affibody libraries, *Proteins-Structure Function. Genetics* 2002, 48, 454-462.
Engflldt, T. et al., Chemical Synthesis of Triple-Labelled Three-Helix Bundle Binding Proteins for specific Fluorescent Detection of Unlabelled Protein, *Chembiochem* 2005, 6, 1043.
Fairbrother, W. et al., Novel Peptides Selected to bind Vascular Endothelial Growth Factor Target the Receptor-Binding Site, *Biochemistry* 1998, 37, 17754-17764.
Fedorova, A. et al., The Development of Peptide-based tools for the Analysis of Angiogenesis, *Chem. Biol.* 2011, 18, 839-845.
Ferrara, N. et al., The biology of VEGF and its receptors, *Nat. Med.* 2003, 9, 669-676.
Ferrara, N. et al., Discovery and Development of Bevacizumab, An Anti-VEGF Antibody for Treating Cancer, *Nat. Rev. Drug Disc.* 2004, 3, 391.
Ferrara, N. et al., Angiogenesis as a therapeutic target, *Nature* 2005, 438, 967.
Friedman, M. et al., Phage display selection of Affibody molecules with specific binding to the extracellular domain of the epidermal growth factor receptor, *Protein Eng.* 2007, 20, 189-199.
Friedman, M. et al., Directed Evolution to low nanomolar Affinity of a Tumor-Targeting Epidermal Growth Factor Receptor-Binding Affibody molecule, *J. Mol. Biol.* 2008, 376, 1388-1402.
Gerbauer, M. et al., Engineered protein scaffolds as next-generation antibody therapeutics, *Curr. Opin. Chem. Biol.* 2009, 13, 245-255.
Gilbreth, R. et al., Structural insights for engineering binding proteins based on non-antibody scaffolds, *Curr. Opin. Struc. Biol.* 2012, 22, 413-420.
Gill, S. et al., Calculation of Protein Extinction Coefficients from Amino Acid Sequence Data, *Anal. Biochem.* 1989, 182, 319-326.
Gouda, H. et al., Three-Dimensional Solution Structure of the B Domain of Staphylococcal Protein A: Comparisons of the Solution and Crystal Structures, *Biochemistry* 1992, 31, 9665-9672.
Grönwall, C. et al.. Engineered affinity proteins—Generation and applications, *J. Biotechnol.* 2009, 140, 254-269.
Haase, H. et al., Extending Foldamer Design Beyond α-Helix mimicry: α/βPeptide Inhibitors of Vascular Endothelial Growth Factor Signaling, *J. Am. Chem. Soc.* 2012, 134, 7652-7655.
Hansen et al., Structure and Function of the Core Histone N-Termini: More Than Meets the Eye, *Biochemistry*, 1998, vol. 37, No. 51, 17637-17641.
Hoghom, M. et al., Structural basis for recognition by an in vitro evolved affibody, *Proc. Natl. Acad. Sci. U.S.A.* 2003, 100, 3191-3196.
Honarvar, H. et al., Evaluation of backbone-cyclized HER2-binding 2-helix Affibody molecule for In Vivo molecular imaging, *Nucl. Med. Biol.* 2013, 40, 378-386.

(Continued)

*Primary Examiner* — Amber D Steele
(74) *Attorney, Agent, or Firm* — Joseph T. Leone, Esq.; DeWitt Ross & Stevens S.C.

(57) ABSTRACT

Described are α/β-peptide mimics of Z-domain scaffold peptides, methods of making them, and methods of using them. The α/β-peptide mimics include β-amino acid residues and, optionally, disulfide bonds to stabilize the conformation of the mimics. The compounds may be truncated as compared to conventional Z-domain scaffold peptides and are resistant to proteolytic degradation due to the presence of β-amino acid residues. The mimics can be made so as to bind selectively to a desired target.

23 Claims, 19 Drawing Sheets

(56) References Cited

OTHER PUBLICATIONS

Horne, S. et al., Helix Bundle Quaternary Structure from α/β-Peptide Foldamers, *J. Am. Chem. Soc.* 2007, 129, 4178-4180.
Horne, W., Sequence-Based Design of α/β-Peptide Foldamers That Mimic BH3 Domains, *Angew. Chem., Int. Ed.* 2008, 47, 2853-2856.
Horne, W. et al., Structural and biological mimicry of protein surface recognition by α/β-peptide foldamers, *Proc. Natl. Acad. Sci. U.S.A.* 2009, 106, 14751-14756.
Horne, W., Peptide and peptoid foldamers in medicinal chemistry, *Exp. Opin. Drug Discov.* 2011, 6, 1247-1262.
Hoyer, W. et al., Stabilization of a β-hairpin in monomeric Alzheimer's amyloid-β peptide inhibits amyloid formation, *Proc. Natl. Acad. Sci. U.S.A.* 2008, 105, 5099-5104.
Järver, P. et al., chemical synthesis and evaluation of a backbone-cyclized minimized 2-helix Z-domain, *J. Pept. Sci.* 2011, 17, 463-469.
Jendeberg, L. et al., the Mechanism of Binding Staphylococcal Protein A to Immunogloblin G Does Not Involve Helix Unwinding, *Biochemistry* 1996, 35, 22-31.
Johnson, L. et al., α-Helix Mimicry with α/β-Peptides, *Method Enzymol.* 2013, vol. 523, Chapter Nineteen, pp. 407-425.
Jonsson, A. et al., Generation of tumour-necrosis-factor-α-specific affibody molecules capable of blocking receptor binding in vitro, *Biotechnol. Appl. Biochem.* 2009, 54, 93-103.
Kronqvist, N. et al., A novel affinity protein selection system based on staphylococcal cell surface display and flow cytometry, *Protein Eng. Des. Sel.* 2008, 21, 247-255.
Langone, J. et al., Protein A of *Staphylococcus aureus* and Related Immunoglobulin Receptors Produced by Streptococco and Pneumonococci, *Adv. Immunol.* 1982, 32, 157-252.
Langone, J. et al., Applications of Immobilized Protein a in Immunochemical Techniques, *J. Immunol. Methods* 1982, 55, 277-296.
Lee, H. et al., An Efficient Route to Either Enantiomer of Orthogonally Protected *trans*-3-Aminopyrrolidine-4-carboxylic Acid, *J. Org. Chem.* 2001, 66, 3597-3599.
Lendel, C. et al., Structural basis for Molecular Recognition in an Affibody: Affibody Complex, *J. Mol. Biol.* 2006, 359, 1293-1304.
Lindborg, M. et al., Engineered high-Affinity Affibody Molecules Targeting Platelet-Derived Growth factor Receptor β In vivo, *J. Mol. Biol.* 2011, 407, 298-315.
Löfblom, J. et al., Affibody molecules: Engineered proteins for therapeutic, diagnostic and biotechnological applications, *FEBS Lett.* 2010, 584, 2670-2680.
Löfdahl, P. el al., Affinity maturation of a TNFα-binding Affibody molecule by Darwinian survival selection, *Biotechnol. Appl. Biochem.* 2010, 55, 111-120.
Mandal, K. et al., Chemical synthesis and X-ray structure of a heterochiral {D-protein antagonist *plus* vascular endothelial growth factor} protein complex by racemic crystallography, *Proc. Natl. Acad. Sci. U.S.A.* 2012, 37, 14779-14784.
Muller, Y. et al., Vascular endothelial growth factor: Crystal structure and functional mapping of the kinase domain receptor binding site, *Proc. Natl. Acad. Sci. U.S.A.* 1997, 94, 7192-7197.
Nilsson, B. et al., a synthetic IgG-binding domain based on staphylococcal protein A, *Protein Eng.* 1987, 1, 107-113.
Nilsson, F. et al., Affibody® molecules: new protein domains for molecular imaging and targeted tumor therapy, *Curr. Opin. Drug Disc.* 2007, 10, 167-175.
Niu et al., Size Effect in Molecular Imaging of Vascular Endothielial Growth Factor, *Chemistry & Biology*, 2011, 18, 819-820.
Nord, L. et al., A combinatorial library of an α-helical bacterial receptor domain, *Protein Eng.* 1995, 8, 601-608.
Nord, K. et al., Binding proteins selected from combinatorial libraries of an α-helical bacterial receptor domain, *Nat. Biotech.* 1997, 15, 772.
Nord, K. et al., Recombinant human factor VIII-specific affinity ligands selected from phage-displayed combinatorial libraries of Protein A, *Eur. J. Biochem.* 2001, 268, 4269-4277.
Nygren, P., Binding proteins from alternative scaffolds, *J. Immunol. Methods* 2004, 290, 3-28.
Nygren, P., alternative binding proteins: Affibody binding proteins developed from a small three-helix bundle scaffold, *FEBS J.* 2008, 275, 2668-2676.
Orlova, A. et al., Tumor Imaging Using a Picomolar Affinity HER2 binding Affibody Molecule, *Cancer Res.* 2006, 66, 4339.
Orlova, A. et al., Synthetic Affibody Molecules: A Novel Class of Affinity Ligands for Molecular Imaging of HER2-Expressing Malignant Tumors, *Cancer Res.* 2007, 67, 2178.
Orlova, A. et al., On the Selection of a Tracer for PET Imaging of HER2-Expressing Tumors: Direct Comparison of a [124]Labeled Affibody Molecule and Trastuzumab in a Murine Xenograft Model, *J. Nucl. Med.* 2009, 50, 417.
Pan, B. et al., Solution Structure of a Phage-derived Peptide Antagonist in Complex with Vascular Endothelial Growth Factor, *J. Mol. Biol.* 2002, 316, 769-787.
Peterson, K. et al., A fluorescence polarization assay for identifying ligands that bind to vascular endothelial growth factor, *Anal. Biochem.* 2008, 378, 8-14.
Price, J. et al., Structural Consequences of αβ-Amino Acid preorganization in a Self-Assembling α/βPeptide: Fundamental Studies of Foldameric Helix Bundles, *J. Am. Chem. Soc.* 2010, 132, 12378.
Ren, G. et al., In vivo targeting of ER2-positive tumor using 2-helix affibody molecules, *Amino Acids* 2012, 43, 405-413.
Skerra, A., Engineered protein scaffolds for molecular recognition, *J. Mol. Recognit.* 2000, 13, 167-187.
Skerra, A., Alternative non-antibody scaffolds for molecular recognition, *Curr. Opin. Biotech.* 2007, 18, 295-304.
Starovasnik, M. et al., Structural mimicry of a native protein by a minimized binding domain, *Proc. Natl. Acad. Sci. U.S.A.* 1997, 94, 10080-10085.
Steer, D. et al., β-Amino Acids: Versatile Peptidomimetics, *Curr. Med. Chem.* 2002, 9, 811-822.
Tashiro, M. et al., High-resolution Solution NMR Structure of the Z Domain of Staphylococcal Protein A, *J. Mol. Biol.* 1997, 272, 573-590.
Tolmachev, V. et al., Radionuclide Therapy of HER2-Positive Microxenografts Using a [177]Lu-Labeled HER2-Specific Affibody Molecule, *Cancer Res.* 2007, 67, 2773.
Tolmachev, W. et al., Update on Affibody molecules for in vivo imaging of targets for cancer therapy, *Minerva Biotecnol.* 2009, 21, 21-30.
Wahlberg, E. et al., An affibody in complex with a target protein: Structure and coupled folding, *Proc. Natl. Acad. Sci. U.S.A.* 2003, 100, 3185-3190.
Wahlberg, E. et al, Conformational Stabilization of an Engineered Binding Protein, *J. Am. Chem. Soc.* 2006, 128, 7651-7660.
Wallberg, H. et al., Affinity recovery of eight HER2-binding affibody variants using an anti-idiotypic affibody molecule as a capture ligand, *Prot. Express. Purif.* 2011, 76, 127-135.
Webster, J. et al., Engineered Two-Helix Small Proteins for Molecular Recognition, *ChemBioChem* 2009, 10, 1293-1296.
Wells, J. et al., Reaching for high-hanging fruit in drug discovery at protein-protein interfaces, *Nature* 2007, 450, 1001.
Wiesmann, C. et al., Crystal Structure at 1.7 Å Resolution of VEGF in complex with Domain 2 of the Flt-1 Receptor, *Cell* 1997, 91, 695-704.
Wikman, M. et al., Selection and characterization of HER2/neu-binding affibody ligands, *Protein Eng. Des. Sel.* 2004, 17, 455-462.
Yamaguchi, H. et al., Effect of α,α-Dialkyl Amino Acids on the Protease Resistance of Peptides, *Biosci. Biotechnol. Biochem.* 2003, 67, 2269-2272.

FIG. 1A
|  | Helix 1 | Helix 2 | Helix 3 |  |
|---|---|---|---|---|
| Z-IgG | VDNKFNKEQQNAFYEILHLPNLNEEQRNAFIQSLKDDPSQSANLLAEAKKLNDAQAPK | | | SEQ. ID. NO: 102 |
| Z-TNFα | VDNKFNKELGWAIGEIGTLPNLNHQQFRAFILSLWDDPSQSANLLAEAKKLNDAQAPK | | | SEQ. ID. NO: 63 |
| Z-HER2 | VDNKFNKEMRNAYWEIALLPNLNNQQKRAFIRSLYDDPSQSANLLAEAKKLNDAQAPK | | | SEQ. ID. NO: 81 |
| Z-VEGF | VDNKFNKEMHNAYAIEIALLPNLNDQQFHAFIWSLIDDPSQSANLLAEAKKLNDAQAPK-NH$_2$ | | | SEQ. ID. NO: 16 |
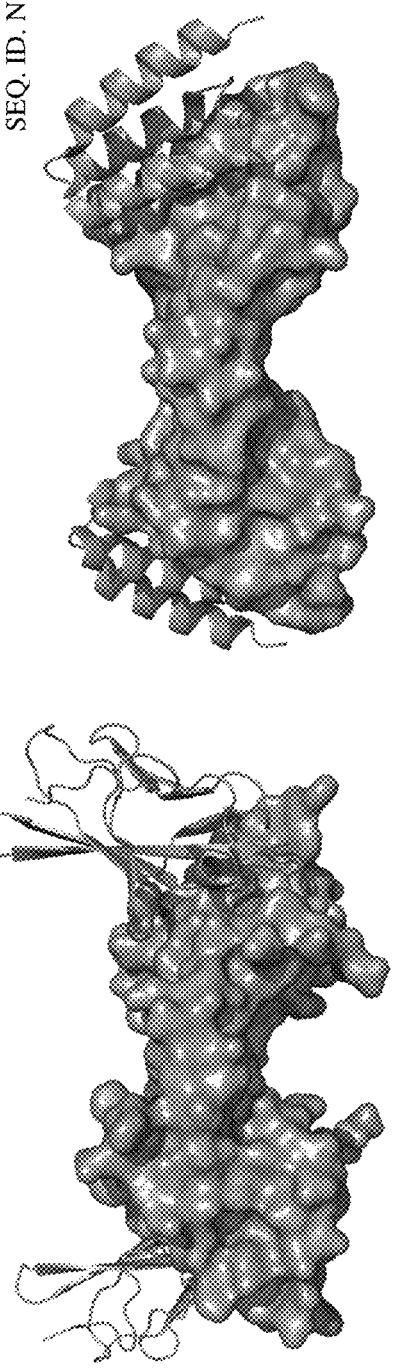
FIG. 1B
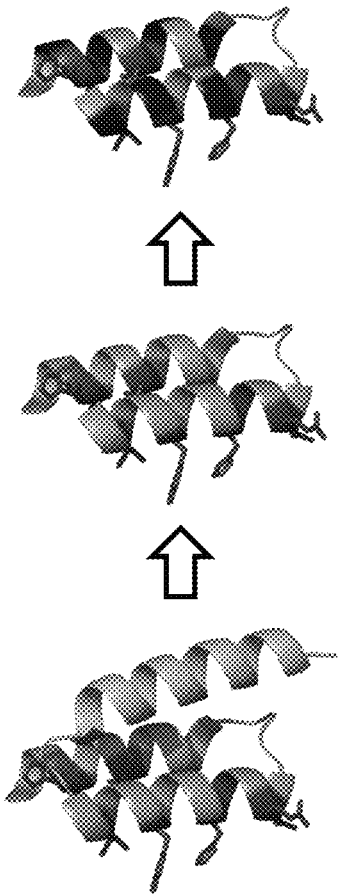
FIG. 1C SEQ. ID. NO: 103 α/β-IgG-1   VDNKFNKXCQZRFYEALHDPNLNEEQRNAKIQZIKXDC-NH₂
SEQ. ID. NO: 104 α/β-IgG-2   VDNKFNKXCQNRFYEALHDPNLNEEQRNAKIQZIKXDC-NH₂
(S-S bridge between the two C residues)

FIG. 5

SEQ. ID. NO: 63 α/β-TNFα-1   VDNKFNKXCQZRIGEAGTDPNLNHQQFRAKILZIWXDC-NH₂
SEQ. ID. NO: 64 α/β-TNFα-2   VDNKFNKXCGWRIGEAGTDPNLNHQQFRAKILZIWXDC-NH₂
(S-S bridge between the two C residues)

FIG. 6

Mini-Z (red), binds IgG
SEQ. ID. NO: 105    FNMQCQRRFYAELHDPNLNEEQRNAKIKSIRDDC

Truncated Z-1-2
SEQ. ID. NO: 106    VDNKFNKEMHNAYAIEIALLPNLNDQQFHAFIWSLIDDP

| Rep. | Note | v114* | α/β-VEGF-1 | α/β-VEGF-2 | Z-VEGF |
|---|---|---|---|---|---|
| 1 | VII-209 | - | - | 0.35 | - |
| 2 | VII-218 | - | 0.083 | - | - |
| 3 | VII-274 | 0.10 | 0.097 | 0.33 | - |
| 4 | VII-282 | 0.084 | 0.11 | 0.38 | 0.41 |

| | | $K_i$ (μM) |
|---|---|---|
| SEQ. ID. NO: 28 α-VEGF-2 | VDNKFNKEQCNARAIEAALDPNLNDQQFHAKIWSIIDDC-NH$_2$ (S-S) | 0.42 |
| SEQ. ID. NO: 19 S1 | VDNKFNKEQCNARAIEAALDPNLNDQQFHAKIWSIIDDCG-NH$_2$ | 0.27 |
| SEQ. ID. NO: 20 S2 | VDNKFNKEQCNARAIEAALDPNLNDQQFHAKIWSIIDDCG-NH$_2$ | 20 |
| SEQ. ID. NO: 21 S3 | VDNKFNKEQCNARAIEAALDPNLNDQQFHAKIWSIIDDCG-NH$_2$ | 1.3 |
| SEQ. ID. NO: 22 S4 | VDNKFNKEQCNARAIEAALDPNLNDQQFHAKIWSIIDDCG-NH$_2$ | 42 |
| SEQ. ID. NO: 23 S5 | VDNKFNKEQCNARAIEAALDPNLNDQQFHAKIWAIIDDCG-NH$_2$ | 0.22 |
| SEQ. ID. NO: 26 S6 | VDNKFNKEQCNARAIEAALDPNLNDQQFHAKIWAIIDDCG-NH$_2$ | 27 |
| SEQ. ID. NO: 29 S7 | VDNKFNKEQCNARAIEAALDPNLNDQQFHAKIWAIIDDCG-NH$_2$ | 0.19 |
| SEQ. ID. NO: 30 S8 | VDNKFNKEQCNARAIEAALDPNLNDQQFHAKIWAIIDDCG-NH$_2$ | 0.35 |
| SEQ. ID. NO: 31 S9 | VDNKFNKEQCNARAIEAALDPNLNDQQFHAKIWAIIDDCG-NH$_2$ | 0.71 |
| SEQ. ID. NO: 32 S10 | VDNKFNKEQCNARAIEAALDPNLNDQQFHAKIWAIIDDCG-NH$_2$ | 0.29 |
| SEQ. ID. NO: 33 S11 | VDNKFNKEQCNARAIEAALDPNLNDQQFHAKIWAIIDDCG-NH$_2$ | 0.26 |
| SEQ. ID. NO: 34 S12 | VDNKFNKEQCNARAIEAALDPNLNDQQFHAKIWAIIDDCG-NH$_2$ | 0.10 |
| SEQ. ID. NO: 35 S13 | VDNKFNKEECNRRAIEAALDPNLNDQQFHEKIWRIIEDCG-NH$_2$ | 0.13 |
| SEQ. ID. NO: 36 S14 | VDNKFNKEECNRRAIEAALDPNLNDQQFHEKIWRIIEDC-NH$_2$ | 0.10 |
| α/β-VEGF-1 SEQ. ID. NO: 27 | VDNKFNKEECNRRAIEAALDPNLNDQQFHEKIWRIIEDC-NH$_2$ | 0.11 |
| α/β-VEGF-1-linear SEQ. ID. NO: 50 | VDNKFNKEEHNRRAIEAALDPNLNDQQFHEKIWRIIED-NH$_2$ | >50 |

FIG. 11

| | | $K_i$ (μM) |
|---|---|---|
| SEQ. ID. NO: 16 Z-VEGF | VDNKFNKEMHNAYAIEIALLPNLNDQQFHAFIWSLIDDPSQSANLLAEAKKLNDAQAPK-NH₂ | 0.41 |
| Z-VEGF (7-56) SEQ. ID. NO: 24 | KEMHNAYAIEIALLPNLNDQQFHAFIWSLIDDPSQSANLLAEAKKLNDAQ-NH₂ | 6.3 |
| SEQ. ID. NO: 19 S1 | VDNKFNKEQCNARAIEAALDPNLNDQQFHAKIWSIIDDCG-NH₂ | 0.27 |
| S15 SEQ. ID. NO: 37 | KEMCNARAIEAALDPNLNDQQFHAKIWSIIDDCG-NH₂ | 11.4 |

M = Nle

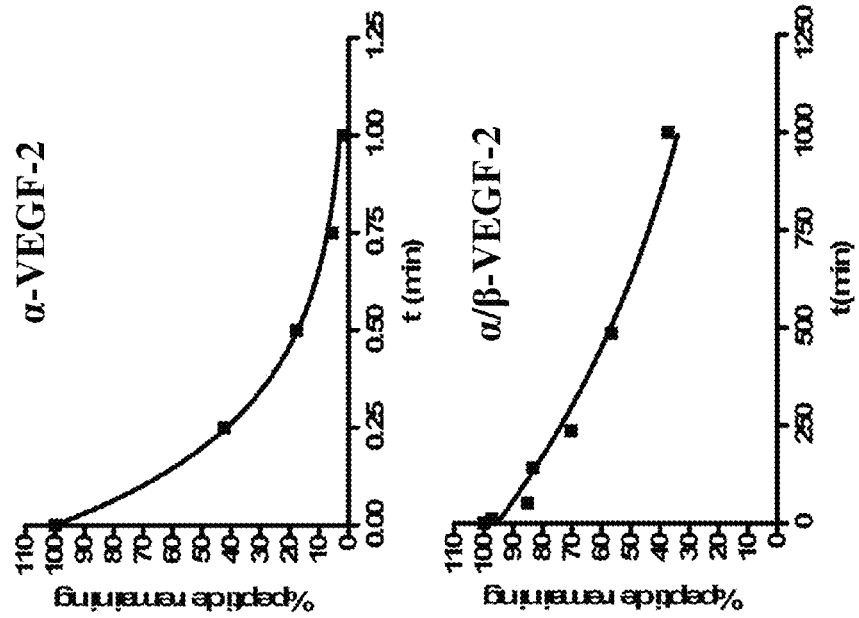
FIG. 15A Z-VEGF
FIG. 15B α-VEGF-2
FIG. 15C α/β-VEGF-1
FIG. 15D α/β-VEGF-2

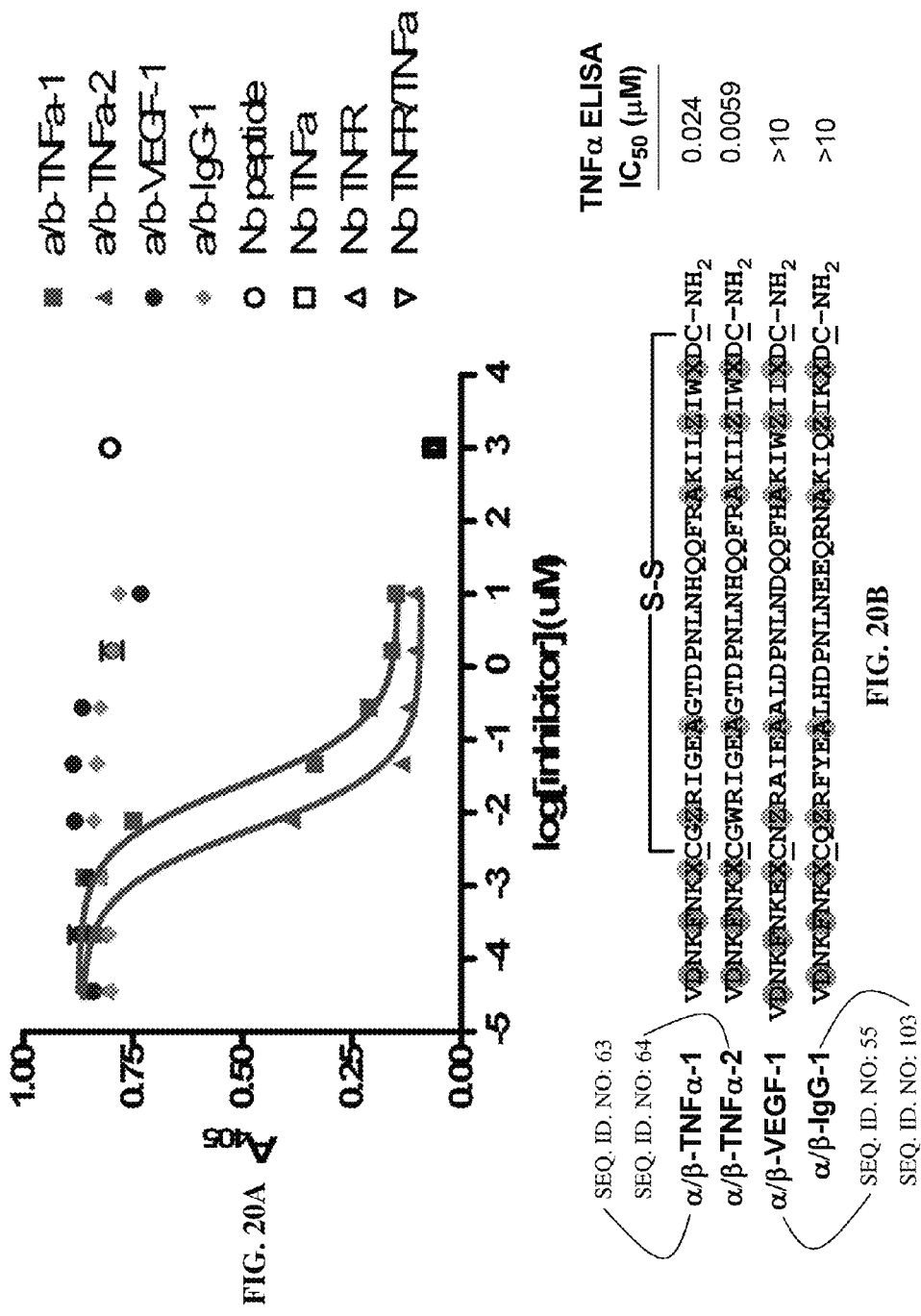

SEQUENCE LISTING

```
<160> NUMBER OF SEQ ID NOS: 106

<210> SEQ ID NO 1
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: Nle

<400> SEQUENCE: 1

Lys Glu Xaa His Asn Arg Tyr Ala Ile Glu Ala Ala Leu Asp Pro Asn
1               5                   10                  15

Leu Asn Asp Gln Gln Phe His Ala Lys Ile Trp Ser Ile Ile Asp Asp
            20                  25                  30

Pro Ser

<210> SEQ ID NO 2
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: Nle
<220> FEATURE:
<221> NAME/KEY: DISULFID
<222> LOCATION: (14)..(25)

<400> SEQUENCE: 2

Lys Glu Xaa His Asn Arg Tyr Ala Ile Glu Ala Ala Leu Cys Pro Asn
1               5                   10                  15

Leu Asn Asp Gln Gln Phe His Ala Cys Ile Trp Ser Ile Ile Asp Asp
            20                  25                  30

Pro Ser

<210> SEQ ID NO 3
```

```
<211> LENGTH: 37
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (1)..(36)
<220> FEATURE:
<221> NAME/KEY: MOD_RES
<222> LOCATION: (5)..(5)
<223> OTHER INFORMATION: 2-aminocyclopentanecarboxylic acid
<220> FEATURE:
<221> NAME/KEY: MOD_RES
<222> LOCATION: (27)..(27)
<223> OTHER INFORMATION: 2-aminocyclopentanecarboxylic acid
<220> FEATURE:
<221> NAME/KEY: MOD_RES
<222> LOCATION: (30)..(30)
<223> OTHER INFORMATION: 2-aminocyclopentanecarboxylic acid

<400> SEQUENCE: 3

Cys Asn Lys Glu Xaa His Asn Ala Tyr Ala Ile Glu Ile Ala Leu Leu
1               5                   10                  15

Pro Asn Leu Asn Asp Gln Gln Phe His Ala Xaa Ile Trp Xaa Leu Ile
            20                  25                  30

Asp Asp Pro Cys Gln
        35

<210> SEQ ID NO 4
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 2-aminocyclopentanecarboxylic acid
<220> FEATURE:
<221> NAME/KEY: MOD_RES
<222> LOCATION: (25)..(25)
<223> OTHER INFORMATION: 2-aminocyclopentanecarboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 4

Lys Glu Xaa His Asn Ala Xaa Ala Ile Glu Ile Ala Leu Leu Pro Asn
1               5                   10                  15

Leu Asn Asp Gln Gln Phe His Ala Xaa Ile Trp Xaa Leu Ile Asp Asp
            20                  25                  30

Pro Ser

<210> SEQ ID NO 5
<211> LENGTH: 34
<212> TYPE: PRT
<213> ORGANISM: Artificial Sequence
<220> FEATURE:
<223> OTHER INFORMATION: Synthesized, unnatural polypeptide

<400> SEQUENCE: 5

Phe Asn Lys Glu Ala Leu Leu Arg Tyr Lys Glu Ala Ala Leu Asp Pro
1               5                   10                  15
```

```
Asn Leu Asn Leu Tyr Gln Arg Ile Ala Lys Ile Val Ser Ile Asp Asp
            20                  25                  30

Asp Ala
```

<210> SEQ ID NO 6
<211> LENGTH: 39
<212> TYPE: PRT
<213> ORGANISM: Artificial Sequence
<220> FEATURE:
<223> OTHER INFORMATION: Synthesized, unnatural polypeptide

<400> SEQUENCE: 6

```
Phe Asn Lys Glu Ala Leu Leu Arg Tyr Lys Glu Ala Ala Leu Asp Pro
1               5                   10                  15

Asn Leu Gly Gly Gly Gly Gly Asn Leu Tyr Gln Arg Ile Ala Lys Ile
            20                  25                  30

Val Ser Ile Asp Asp Asp Ala
            35
```

<210> SEQ ID NO 7
<211> LENGTH: 40
<212> TYPE: PRT
<213> ORGANISM: Artificial Sequence
<220> FEATURE:
<223> OTHER INFORMATION: Synthesized, unnatural polypeptide

<400> SEQUENCE: 7

```
Phe Asn Lys Glu Ala Leu Leu Arg Tyr Lys Glu Ala Ala Leu Asp Pro
1               5                   10                  15

Asn Leu Gly Gly Gly Gly Gly Gly Asn Leu Tyr Gln Arg Ile Ala Lys
            20                  25                  30

Ile Val Ser Ile Asp Asp Asp Ala
            35                  40
```

<210> SEQ ID NO 8
<211> LENGTH: 17
<212> TYPE: PRT
<213> ORGANISM: Artificial Sequence
<220> FEATURE:
<223> OTHER INFORMATION: Synthesized, unnatural polypeptide

<400> SEQUENCE: 8

```
Arg Arg Leu Tyr Glu Glu Ile Arg Arg Ile Val Glu Glu Asp Arg Arg
1               5                   10                  15

Ala
```

<210> SEQ ID NO 9
<211> LENGTH: 17
<212> TYPE: PRT
<213> ORGANISM: Artificial Sequence
<220> FEATURE:
<223> OTHER INFORMATION: Synthesized, unnatural polypeptide

<400> SEQUENCE: 9

```
Ala Arg Leu Tyr Glu Ala Ile Ala Arg Ile Val Glu Ala Asp Ala Arg
1               5                   10                  15

Ala
```

<210> SEQ ID NO 10
<211> LENGTH: 17
<212> TYPE: PRT
<213> ORGANISM: Artificial Sequence
<220> FEATURE:

```
<223> OTHER INFORMATION: Synthesized, unnatural polypeptide

<400> SEQUENCE: 10

Glu Glu Leu Tyr Arg Arg Ile Glu Glu Ile Val Arg Arg Asp Glu Glu
1               5                   10                  15

Ala

<210> SEQ ID NO 11
<211> LENGTH: 17
<212> TYPE: PRT
<213> ORGANISM: Artificial Sequence
<220> FEATURE:
<223> OTHER INFORMATION: Synthesized, unnatural polypeptide

<400> SEQUENCE: 11

Ala Glu Leu Tyr Arg Ala Ile Ala Glu Ile Val Arg Ala Asp Ala Glu
1               5                   10                  15

Ala

<210> SEQ ID NO 12
<211> LENGTH: 17
<212> TYPE: PRT
<213> ORGANISM: Artificial Sequence
<220> FEATURE:
<223> OTHER INFORMATION: Synthesized, unnatural polypeptide

<400> SEQUENCE: 12

Leu Glu Leu Tyr Arg Arg Ile Ala Glu Ile Val Arg Ile Asp Asp Glu
1               5                   10                  15

Ala

<210> SEQ ID NO 13
<211> LENGTH: 17
<212> TYPE: PRT
<213> ORGANISM: Artificial Sequence
<220> FEATURE:
<223> OTHER INFORMATION: Synthesized, unnatural polypeptide

<400> SEQUENCE: 13

Leu Arg Leu Tyr Glu Arg Ile Ala Arg Ile Val Glu Ile Asp Asp Arg
1               5                   10                  15

Ala

<210> SEQ ID NO 14
<211> LENGTH: 17
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (16)..(16)
<223> OTHER INFORMATION: Aib

<400> SEQUENCE: 14

Leu Asn Leu Tyr Xaa Arg Ile Ala Lys Ile Val Ser Ile Asp Asp Xaa
1               5                   10                  15

Ala

<210> SEQ ID NO 15
```

```
<211> LENGTH: 17
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (16)..(16)
<223> OTHER INFORMATION: Aib

<400> SEQUENCE: 15

Leu Asn Leu Tyr Xaa Arg Ile Ala Xaa Ile Val Xaa Ile Asp Asp Xaa
1               5                   10                  15

Ala

<210> SEQ ID NO 16
<211> LENGTH: 59
<212> TYPE: PRT
<213> ORGANISM: Homo sapiens

<400> SEQUENCE: 16

Val Asp Asn Lys Phe Asn Lys Glu Met His Asn Ala Tyr Ala Ile Glu
1               5                   10                  15

Ile Ala Leu Leu Pro Asn Leu Asn Asp Gln Gln Phe His Ala Phe Ile
            20                  25                  30

Trp Ser Leu Ile Asp Asp Pro Ser Gln Ser Ala Asn Leu Leu Ala Glu
        35                  40                  45

Ala Lys Lys Leu Asn Asp Ala Gln Ala Pro Lys
    50                  55

<210> SEQ ID NO 17
<211> LENGTH: 59
<212> TYPE: PRT
<213> ORGANISM: Artificial Sequence
<220> FEATURE:
<223> OTHER INFORMATION: Synthesized, unnatural polypeptide

<400> SEQUENCE: 17

Val Asp Asn Lys Phe Asn Lys Glu Met His Asn Ala Tyr Ala Ile Glu
1               5                   10                  15

Ile Ala Leu Leu Pro Asn Leu Asn Asp Gln Gln Phe His Ala Phe Ile
            20                  25                  30

Trp Ser Leu Ile Asp Asp Pro Ser Gln Ser Ala Asn Leu Leu Ala Glu
        35                  40                  45

Ala Lys Lys Leu Asn Asp Ala Gln Ala Pro Lys
    50                  55

<210> SEQ ID NO 18
<211> LENGTH: 34
<212> TYPE: PRT
<213> ORGANISM: Homo sapiens

<400> SEQUENCE: 18
```

-continued

Lys Glu Met His Asn Ala Tyr Ala Ile Glu Ile Ala Leu Leu Pro Asn
1               5                   10                  15
Leu Asn Asp Gln Gln Phe His Ala Phe Ile Trp Ser Leu Ile Asp Asp
            20                  25                  30
Pro Ser

<210> SEQ ID NO 19
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: DISULFID
<222> LOCATION: (4)..(33)

<400> SEQUENCE: 19

Lys Glu Xaa Cys Asn Ala Arg Ala Ile Glu Ala Ala Leu Asp Pro Asn
1               5                   10                  15
Leu Asn Asp Gln Gln Phe His Ala Lys Ile Trp Ser Ile Ile Asp Asp
            20                  25                  30
Cys Gly

<210> SEQ ID NO 20
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(33)
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib

<400> SEQUENCE: 20

Lys Glu Gln Cys Asn Ala Arg Ala Ile Glu Xaa Ala Leu Asp Pro Asn
1               5                   10                  15
Leu Asn Asp Gln Gln Phe His Xaa Lys Ile Trp Ser Ile Ile Asp Asp
            20                  25                  30
Cys Gly

<210> SEQ ID NO 21
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(33)
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)

```
<223> OTHER INFORMATION: Aib
<220> FEATURE:
<221> NAME/KEY: MOD_RES
<222> LOCATION: (28)..(28)
<223> OTHER INFORMATION: Aib

<400> SEQUENCE: 21

Lys Glu Gln Cys Asn Ala Arg Ala Ile Glu Xaa Ala Leu Asp Pro Asn
1               5                   10                  15

Leu Asn Asp Gln Gln Phe His Xaa Lys Ile Trp Xaa Ile Ile Asp Asp
            20                  25                  30

Cys Gly

<210> SEQ ID NO 22
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(33)
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (28)..(28)
<223> OTHER INFORMATION: Aib

<400> SEQUENCE: 22

Lys Glu Gln Cys Asn Ala Xaa Ala Ile Glu Xaa Ala Leu Asp Pro Asn
1               5                   10                  15

Leu Asn Asp Gln Gln Phe His Xaa Lys Ile Trp Xaa Ile Ile Asp Asp
            20                  25                  30

Cys Gly

<210> SEQ ID NO 23
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(33)
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (24)..(24)
<223> OTHER INFORMATION: 2-aminocyclopentanecarboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 23

Lys Glu Gln Cys Asn Ala Xaa Ala Ile Glu Ala Ala Leu Asp Pro Asn
```

```
                1               5                  10                  15
Leu Asn Asp Gln Gln Phe His Xaa Lys Ile Trp Xaa Ile Ile Asp Asp
            20                  25                  30

Cys Gly

<210> SEQ ID NO 24
<211> LENGTH: 50
<212> TYPE: PRT
<213> ORGANISM: Homo sapiens

<400> SEQUENCE: 24

Lys Glu Met His Asn Ala Tyr Ala Ile Glu Ile Ala Leu Leu Pro Asn
1               5                  10                  15

Leu Asn Asp Gln Gln Phe His Ala Phe Ile Trp Ser Leu Ile Asp Asp
            20                  25                  30

Pro Ser Gln Ser Ala Asn Leu Leu Ala Glu Ala Lys Lys Leu Asn Asp
        35                  40                  45

Ala Gln
    50

<210> SEQ ID NO 25
<211> LENGTH: 38
<212> TYPE: PRT
<213> ORGANISM: Homo sapiens

<400> SEQUENCE: 25

Val Asp Asn Lys Phe Asn Lys Glu Met His Asn Ala Tyr Ala Ile Glu
1               5                  10                  15

Ile Ala Leu Leu Pro Asn Leu Asn Asp Gln Gln Phe His Ala Phe Ile
            20                  25                  30

Trp Ser Leu Ile Asp Asp
        35

<210> SEQ ID NO 26
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 26

Val Asp Asn Lys Phe Asn Lys Glu Gln Cys Asn Ala Tyr Ala Ile Glu
1               5                  10                  15

Ile Ala Leu Leu Pro Asn Leu Asn Asp Gln Gln Phe His Ala Phe Ile
            20                  25                  30

Trp Ser Leu Ile Asp Asp Cys Gly
        35                  40

<210> SEQ ID NO 27
<211> LENGTH: 38
<212> TYPE: PRT
<213> ORGANISM: Artificial Sequence
<220> FEATURE:
<223> OTHER INFORMATION: Synthesized, unnatural polypeptide

<400> SEQUENCE: 27

Val Asp Asn Lys Phe Asn Lys Glu Gln His Asn Ala Arg Ala Ile Glu
1               5                  10                  15
```

Ala Ala Leu Asp Pro Asn Leu Asn Asp Gln Gln Phe His Ala Lys Ile
            20                  25                  30

Trp Ser Ile Ile Asp Asp
        35

<210> SEQ ID NO 28
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 28

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Ala Lys Ile
            20                  25                  30

Trp Ser Ile Ile Asp Asp Cys
        35

<210> SEQ ID NO 29
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 29

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Ala Lys Ile
            20                  25                  30

Trp Ser Ile Ile Asp Asp Cys Gly
        35                  40

<210> SEQ ID NO 30
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (31)..(31)
<223> OTHER INFORMATION: Beta-3 Lys
<220> FEATURE:
<221> NAME/KEY: MOD_RES
<222> LOCATION: (34)..(34)
<223> OTHER INFORMATION: Beta-3 Ser
<220> FEATURE:
<221> NAME/KEY: MOD_RES
<222> LOCATION: (38)..(38)
<223> OTHER INFORMATION: Beta-3 Asp

<400> SEQUENCE: 30

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Ala Xaa Ile

```
            20                  25                  30

Trp Xaa Ile Ile Asp Xaa Cys Gly
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (30)..(30)
<223> OTHER INFORMATION: 2-aminocyclopentanecarboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 31

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Xaa Lys Ile
            20                  25                  30

Trp Xaa Ile Ile Asp Asp Cys Gly
        35                  40

<210> SEQ ID NO 32
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (30)..(30)
<223> OTHER INFORMATION: 2-aminocyclopentanecarboxylic acid

<400> SEQUENCE: 32

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Xaa Lys Ile
            20                  25                  30

Trp Ser Ile Ile Asp Asp Cys Gly
        35                  40

<210> SEQ ID NO 33
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 33

Val Asp Asn Lys Phe Asn Lys Glu Gln Cys Asn Ala Arg Ala Ile Glu
```

```
                1               5                  10                 15
Ala Ala Leu Asp Pro Asn Leu Asn Asp Gln Gln Phe His Ala Lys Ile
            20                  25                 30

Trp Xaa Ile Ile Asp Asp Cys Gly
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (38)..(38)
<223> OTHER INFORMATION: N-succinyl-3-aminopyrrolidine-4-carboxylic acid

<400> SEQUENCE: 34

Val Asp Asn Lys Phe Asn Lys Glu Gln Cys Asn Ala Arg Ala Ile Glu
1               5                   10                  15

Ala Ala Leu Asp Pro Asn Leu Asn Asp Gln Gln Phe His Ala Lys Ile
            20                  25                 30

Trp Ser Ile Ile Asp Xaa Cys Gly
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: Aib

<400> SEQUENCE: 35

Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                 30

Trp Xaa Ile Ile Asp Asp Cys Gly
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
```

```
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: 2-aminocyclopentanecarboxylic acid
<220> FEATURE:
<221> NAME/KEY: MOD_RES
<222> LOCATION: (34)..(34)
<223> OTHER INFORMATION: Aib

<400> SEQUENCE: 36

Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 37

Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40

<210> SEQ ID NO 38
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid
```

```
-continued

<220> FEATURE:
<221> NAME/KEY: MOD_RES
<222> LOCATION: (38)..(38)
<223> OTHER INFORMATION: N-succinyl-3-aminopyrrolidine-4-carboxylic acid

<400> SEQUENCE: 38

Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Xaa Cys Gly
        35                  40

<210> SEQ ID NO 39
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid
<220> FEATURE:
<221> NAME/KEY: MOD_RES
<222> LOCATION: (37)..(37)
<223> OTHER INFORMATION: N-succinyl-3-aminopyrrolidine-4-carboxylic acid

<400> SEQUENCE: 39

Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp Cys Gly
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 40
```

```
Val Asp Asn Lys Phe Asn Lys Glu Gln Cys Asn Ala Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40
```

<210> SEQ ID NO 41
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: Aib
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 41

```
Val Asp Asn Lys Phe Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40
```

<210> SEQ ID NO 42
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 2-aminocyclopentanecarboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 42

```
Val Asp Asn Lys Phe Asn Lys Glu Gln Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40
```

<210> SEQ ID NO 43
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 43

```
Val Asp Asn Lys Phe Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Asp Asp Cys Gly
        35                  40
```

<210> SEQ ID NO 44
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 2-aminocyclopentanecarboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:

```
<221> NAME/KEY: MOD_RES
<222> LOCATION: (34)..(34)
<223> OTHER INFORMATION: 2-aminocyclopentanecarboxylic acid
<220> FEATURE:
<221> NAME/KEY: MOD_RES
<222> LOCATION: (37)..(37)
<223> OTHER INFORMATION: N-succinyl-3-aminopyrrolidine-4-carboxylic acid

<400> SEQUENCE: 44

Val Asp Asn Lys Phe Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp Cys Gly
        35                  40

<210> SEQ ID NO 45
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 2-aminocyclopentanecarboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 2-aminocyclopentanecarboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 45

Val Asp Asn Lys Phe Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp Cys Gly
        35                  40

<210> SEQ ID NO 46
<211> LENGTH: 37
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (6)..(6)
<223> OTHER INFORMATION: 2-aminocyclopentanecarboxylic acid
<220> FEATURE:
<221> NAME/KEY: DISULFID
<222> LOCATION: (7)..(36)
```

-continued

```
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: MOD_RES
<222> LOCATION: (14)..(14)
<223> OTHER INFORMATION: Aib
<220> FEATURE:
<221> NAME/KEY: MOD_RES
<222> LOCATION: (27)..(27)
<223> OTHER INFORMATION: Aib
<220> FEATURE:
<221> NAME/KEY: MOD_RES
<222> LOCATION: (31)..(31)
<223> OTHER INFORMATION: 2-aminocyclopentanecarboxylic acid
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 46

Lys Phe Asn Lys Glu Xaa Cys Asn Xaa Arg Ala Ile Glu Xaa Ala Leu
1               5                   10                  15

Asp Pro Asn Leu Asn Asp Gln Gln Phe His Xaa Lys Ile Trp Xaa Ile
            20                  25                  30

Ile Xaa Asp Cys Gly
        35

<210> SEQ ID NO 47
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: 2-aminocyclopentanecarboxylic acid
<220> FEATURE:
<221> NAME/KEY: DISULFID
<222> LOCATION: (4)..(33)
<220> FEATURE:
<221> NAME/KEY: MOD_RES
<222> LOCATION: (6)..(6)
<223> OTHER INFORMATION: 2-aminocyclopentanecarboxylic acid
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (28)..(28)
<223> OTHER INFORMATION: 2-aminocyclopentanecarboxylic acid
<220> FEATURE:
<221> NAME/KEY: MOD_RES
<222> LOCATION: (31)..(31)
<223> OTHER INFORMATION: 2-aminocyclopentanecarboxylic acid

<400> SEQUENCE: 47

Lys Glu Xaa Cys Asn Xaa Arg Ala Ile Glu Xaa Ala Leu Asp Pro Asn
1               5                   10                  15

Leu Asn Asp Gln Gln Phe His Xaa Lys Ile Trp Xaa Ile Ile Xaa Asp
            20                  25                  30

Cys Gly

<210> SEQ ID NO 48
```

```
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 48

Val Asp Asn Lys Phe Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp Cys
        35

<210> SEQ ID NO 49
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
```

```
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 49

Val Xaa Asn Lys Xaa Asn Lys Glu Xaa Cys Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp Cys
        35

<210> SEQ ID NO 50
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 50

Val Xaa Asn Lys Xaa Asn Lys Glu Xaa His Asn Xaa Arg Ala Ile Glu
1               5                   10                  15

Xaa Ala Leu Asp Pro Asn Leu Asn Asp Gln Gln Phe His Xaa Lys Ile
            20                  25                  30

Trp Xaa Ile Ile Xaa Asp
        35

<210> SEQ ID NO 51
<211> LENGTH: 36
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
```

```
<222> LOCATION: (2)..(2)
<223> OTHER INFORMATION: Beta-3 Phe
<220> FEATURE:
<221> NAME/KEY: MOD_RES
<222> LOCATION: (6)..(6)
<223> OTHER INFORMATION: 2-aminocyclopentanecarboxylic acid
<220> FEATURE:
<221> NAME/KEY: DISULFID
<222> LOCATION: (7)..(36)
<220> FEATURE:
<221> NAME/KEY: MOD_RES
<222> LOCATION: (9)..(9)
<223> OTHER INFORMATION: 3-aminopyrrolidine-4-carboxylic acid
<220> FEATURE:
<221> NAME/KEY: MOD_RES
<222> LOCATION: (14)..(14)
<223> OTHER INFORMATION: Aib
<220> FEATURE:
<221> NAME/KEY: MOD_RES
<222> LOCATION: (27)..(27)
<223> OTHER INFORMATION: Aib
<220> FEATURE:
<221> NAME/KEY: MOD_RES
<222> LOCATION: (31)..(31)
<223> OTHER INFORMATION: 3-aminopyrrolidine-4-carboxylic acid
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 51

Lys Xaa Asn Lys Glu Xaa Cys Asn Xaa Arg Ala Ile Glu Xaa Ala Leu
1               5                  10                  15

Asp Pro Asn Leu Asn Asp Gln Gln Phe His Xaa Lys Ile Trp Xaa Ile
            20                  25                  30

Ile Xaa Asp Cys
        35

<210> SEQ ID NO 52
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 52

Val Asp Asn Lys Phe Asn Lys Glu Xaa Cys Asn Xaa Arg Ala Ile Glu
```

```
                1               5                   10                  15
Xaa Ala Leu Asp Pro Asn Leu Asn Asp Ala Gln Phe His Xaa Lys Ile
            20                  25                  30

Trp Xaa Ile Ile Xaa Asp Cys
        35

<210> SEQ ID NO 53
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 53

Val Xaa Asn Lys Xaa Asn Lys Glu Xaa Cys Asn Xaa Arg Ala Ile Glu
1               5                   10                  15

Xaa Ala Leu Asp Pro Asn Leu Asn Asp Ala Gln Phe His Xaa Lys Ile
            20                  25                  30

Trp Xaa Ile Ile Xaa Asp Cys
        35

<210> SEQ ID NO 54
<211> LENGTH: 36
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Phe
<220> FEATURE:
<221> NAME/KEY: MOD_RES
<222> LOCATION: (6)..(6)
<223> OTHER INFORMATION: 2-aminocyclopentanecarboxylic acid
<220> FEATURE:
<221> NAME/KEY: DISULFID
```

-continued

```
<222> LOCATION: (7)..(36)
<220> FEATURE:
<221> NAME/KEY: MOD_RES
<222> LOCATION: (9)..(9)
<223> OTHER INFORMATION: 3-aminopyrrolidine-4-carboxylic acid
<220> FEATURE:
<221> NAME/KEY: MOD_RES
<222> LOCATION: (14)..(14)
<223> OTHER INFORMATION: Aib
<220> FEATURE:
<221> NAME/KEY: MOD_RES
<222> LOCATION: (27)..(27)
<223> OTHER INFORMATION: Aib
<220> FEATURE:
<221> NAME/KEY: MOD_RES
<222> LOCATION: (31)..(31)
<223> OTHER INFORMATION: 3-aminopyrrolidine-4-carboxylic acid
<220> FEATURE:
<221> NAME/KEY: MOD_RES
<222> LOCATION: (34)..(34)
<223> OTHER INFORMATION: 2-aminocyclopentanecarboxylic acid

<400> SEQUENCE: 54

Lys Xaa Asn Lys Glu Xaa Cys Asn Xaa Arg Ala Ile Glu Xaa Ala Leu
1               5                   10                  15

Asp Pro Asn Leu Asn Asp Ala Gln Phe His Xaa Lys Ile Trp Xaa Ile
                20                  25                  30

Ile Xaa Asp Cys
        35

<210> SEQ ID NO 55
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (9)..(9)
<223> OTHER INFORMATION: 2-aminocyclopentanecarboxylic acid
<220> FEATURE:
<221> NAME/KEY: DISULFID
<222> LOCATION: (10)..(39)
<220> FEATURE:
<221> NAME/KEY: MOD_RES
<222> LOCATION: (12)..(12)
<223> OTHER INFORMATION: 3-aminopyrrolidine-4-carboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (30)..(30)
<223> OTHER INFORMATION: Aib
<220> FEATURE:
<221> NAME/KEY: MOD_RES
<222> LOCATION: (34)..(34)
<223> OTHER INFORMATION: 3-aminopyrrolidine-4-carboxylic acid
<220> FEATURE:
<221> NAME/KEY: MOD_RES
<222> LOCATION: (37)..(37)
<223> OTHER INFORMATION: 2-aminocyclopentanecarboxylic acid

<400> SEQUENCE: 55

Val Xaa Asn Lys Xaa Asn Lys Glu Xaa Cys Asn Xaa Arg Ala Ile Glu
```

```
1               5                   10                  15
Xaa Ala Leu Asp Pro Asn Leu Asn Asp Gln Gln Phe His Xaa Lys Ile
            20                  25                  30

Trp Xaa Ile Ile Xaa Asp Cys
        35
```

<210> SEQ ID NO 56
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 56

```
Val Asp Asn Lys Phe Asn Lys Glu Glu Cys Asn Ala Arg Ala Ile Glu
1               5                   10                  15

Ala Ala Leu Asp Pro Asn Leu Asn Asp Gln Gln Phe His Ala Lys Ile
            20                  25                  30

Trp Arg Ile Ile Asp Asp Cys Gly
        35                  40
```

<210> SEQ ID NO 57
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 57

```
Val Asp Asn Lys Phe Asn Lys Glu Glu Cys Asn Arg Arg Ala Ile Glu
1               5                   10                  15

Ala Ala Leu Asp Pro Asn Leu Asn Asp Gln Gln Phe His Glu Lys Ile
            20                  25                  30

Trp Arg Ile Ile Glu Asp Cys Gly
        35                  40
```

<210> SEQ ID NO 58
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 58

```
Val Asp Asn Lys Phe Asn Lys Glu Glu Cys Asn Arg Arg Ala Ile Glu
1               5                   10                  15

Ala Ala Leu Arg Pro Asn Leu Asn Asp Gln Gln Phe His Glu Glu Ile
            20                  25                  30

Trp Arg Ile Ile Glu Glu Cys Gly
        35                  40
```

<210> SEQ ID NO 59
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 59

Val Asp Asn Lys Phe Asn Lys Glu Glu Cys Asn Arg Arg Ala Ile Glu
1               5                   10                  15

Ala Ala Leu Arg Pro Asn Leu Asn Asp Gln Gln Phe His Arg Arg Ile
            20                  25                  30

Trp Glu Ile Ile Arg Arg Cys Gly
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 60

Val Asp Asn Lys Phe Asn Lys Glu Arg Cys Asn Glu Glu Ala Ile Arg
1               5                   10                  15

Ala Ala Leu Asp Pro Asn Leu Asn Asp Gln Gln Phe His Arg Arg Ile
            20                  25                  30

Trp Glu Ile Ile Arg Arg Cys Gly
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (10)..(39)

<400> SEQUENCE: 61

Val Asp Asn Lys Phe Asn Lys Glu Arg Cys Asn Glu Glu Ala Ile Arg
1               5                   10                  15

Ala Ala Leu Asp Pro Asn Leu Asn Asp Gln Gln Phe His Glu Glu Ile
            20                  25                  30

Trp Arg Ile Ile Glu Glu Cys Gly
        35                  40

<210> SEQ ID NO 62
<211> LENGTH: 58
<212> TYPE: PRT
<213> ORGANISM: Homo sapiens

<400> SEQUENCE: 62

Val Asp Asn Lys Phe Asn Lys Glu Leu Gly Trp Ala Ile Gly Glu Ile
1               5                   10                  15

Gly Thr Leu Pro Asn Leu Asn His Gln Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys

<210> SEQ ID NO 63
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (11)..(11)
<223> OTHER INFORMATION: 3-aminopyrrolidine-4-carboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 63

Val Xaa Asn Lys Xaa Asn Lys Xaa Cys Gly Xaa Arg Ile Gly Glu Xaa
 1               5                  10                  15

Gly Thr Asp Pro Asn Leu Asn His Gln Gln Phe Arg Xaa Lys Ile Leu
            20                  25                  30

Xaa Ile Trp Xaa Asp Cys
        35

<210> SEQ ID NO 64
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)

<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 64

Val Xaa Asn Lys Xaa Asn Lys Xaa Cys Gly Trp Arg Ile Gly Glu Xaa
1               5                   10                  15

Gly Thr Asp Pro Asn Leu Asn His Gln Gln Phe Arg Xaa Lys Ile Leu
            20                  25                  30

Xaa Ile Trp Xaa Asp Cys
        35

<210> SEQ ID NO 65
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 65

Val Xaa Asn Lys Xaa Asn Lys Xaa Leu Gly Trp Arg Ile Gly Glu Xaa
1               5                   10                  15

Gly Thr Asp Pro Asn Leu Asn His Gln Gln Phe Arg Xaa Lys Ile Leu
            20                  25                  30

Xaa Ile Trp Xaa Asp Pro
        35

<210> SEQ ID NO 66
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp

```
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (11)..(11)
<223> OTHER INFORMATION: Beta-3 Trp
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 66

Val Xaa Asn Lys Xaa Asn Lys Xaa Cys Gly Xaa Arg Ile Gly Glu Xaa
1               5                   10                  15

Gly Thr Asp Pro Asn Leu Asn His Gln Gln Phe Arg Xaa Lys Ile Leu
            20                  25                  30

Xaa Ile Trp Xaa Asp Cys
        35

<210> SEQ ID NO 67
<211> LENGTH: 33
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: 2-aminocyclopentanecarboxylic acid
<220> FEATURE:
<221> NAME/KEY: MOD_RES
<222> LOCATION: (6)..(6)
<223> OTHER INFORMATION: 3-aminopyrrolidine-4-carboxylic acid
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (28)..(28)
<223> OTHER INFORMATION: 3-aminopyrrolidine-4-carboxylic acid
<220> FEATURE:
<221> NAME/KEY: MOD_RES
<222> LOCATION: (31)..(31)
<223> OTHER INFORMATION: 2-aminocyclopentanecarboxylic acid

<400> SEQUENCE: 67

Asn Lys Xaa Cys Gly Xaa Arg Ile Gly Glu Xaa Gly Thr Asp Pro Asn
1               5                   10                  15

Leu Asn His Gln Gln Phe Arg Xaa Lys Ile Leu Xaa Ile Trp Xaa Asp
            20                  25                  30
```

Cys

<210> SEQ ID NO 68
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (11)..(11)
<223> OTHER INFORMATION: 3-aminopyrrolidine-4-carboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 68

Val Xaa Asn Lys Xaa Asn Lys Xaa Leu Gly Xaa Arg Ile Gly Glu Xaa
1               5                   10                  15

Gly Thr Asp Pro Asn Leu Asn His Gln Gln Phe Arg Xaa Lys Ile Leu
            20                  25                  30

Xaa Ile Trp Xaa Asp Pro
        35

<210> SEQ ID NO 69
<211> LENGTH: 33
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: 2-aminocyclopentanecarboxylic acid
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (28)..(28)
<223> OTHER INFORMATION: 3-aminopyrrolidine-4-carboxylic acid
<220> FEATURE:
<221> NAME/KEY: MOD_RES
<222> LOCATION: (31)..(31)
<223> OTHER INFORMATION: 2-aminocyclopentanecarboxylic acid

<400> SEQUENCE: 69

Asn Lys Xaa Leu Gly Trp Arg Ile Gly Glu Xaa Gly Thr Asp Pro Asn
1               5                   10                  15

Leu Asn His Gln Gln Phe Arg Xaa Lys Ile Leu Xaa Ile Trp Xaa Asp
            20                  25                  30

Pro

<210> SEQ ID NO 70
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 70

Val Xaa Asn Lys Xaa Asn Lys Xaa Leu Gly Trp Ala Ile Gly Glu Leu
1               5                   10                  15

Gly Thr Asp Pro Asn Leu Asn His Gln Gln Phe Arg Xaa Lys Ala Leu
            20                  25                  30

Xaa Leu Trp Xaa Asp Pro
        35

<210> SEQ ID NO 71
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: MOD_RES
<222> LOCATION: (29)..(29)
<223> OTHER INFORMATION: Aib

```
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 71

Val Xaa Asn Lys Xaa Asn Lys Xaa Cys Gly Trp Ala Ile Gly Glu Leu
1               5                   10                  15

Gly Thr Asp Pro Asn Leu Asn His Gln Gln Phe Arg Xaa Lys Ala Leu
            20                  25                  30

Xaa Leu Trp Xaa Asp Cys
        35

<210> SEQ ID NO 72
<211> LENGTH: 30
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (25)..(25)
<223> OTHER INFORMATION: 3-aminopyrrolidine-4-carboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 72

Cys Gly Trp Arg Ile Gly Glu Xaa Gly Thr Asp Pro Asn Leu Asn His
1               5                   10                  15

Gln Gln Phe Arg Xaa Lys Ile Leu Xaa Ile Trp Xaa Asp Cys
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (25)..(25)
<223> OTHER INFORMATION: 3-aminopyrrolidine-4-carboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 73

Leu Gly Trp Arg Ile Gly Glu Xaa Gly Thr Asp Pro Asn Leu Asn His
```

```
1               5                   10                  15
Gln Gln Phe Arg Xaa Lys Ile Leu Xaa Ile Trp Xaa Asp Pro
        20                  25                  30

<210> SEQ ID NO 74
<211> LENGTH: 28
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (19)..(19)
<223> OTHER INFORMATION: Aib
<220> FEATURE:
<221> NAME/KEY: MOD_RES
<222> LOCATION: (23)..(23)
<223> OTHER INFORMATION: 3-aminopyrrolidine-4-carboxylic acid
<220> FEATURE:
<221> NAME/KEY: MOD_RES
<222> LOCATION: (26)..(26)
<223> OTHER INFORMATION: 2-aminocyclopentanecarboxylic acid

<400> SEQUENCE: 74

Trp Arg Ile Gly Glu Xaa Gly Thr Asp Pro Asn Leu Asn His Gln Gln
1               5                   10                  15

Phe Arg Xaa Lys Ile Leu Xaa Ile Trp Xaa Asp Pro
        20                  25

<210> SEQ ID NO 75
<211> LENGTH: 28
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: Beta-3 Trp
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (19)..(19)
<223> OTHER INFORMATION: Aib
<220> FEATURE:
<221> NAME/KEY: MOD_RES
<222> LOCATION: (23)..(23)
<223> OTHER INFORMATION: 3-aminopyrrolidine-4-carboxylic acid
<220> FEATURE:
<221> NAME/KEY: MOD_RES
<222> LOCATION: (26)..(26)
<223> OTHER INFORMATION: 2-aminocyclopentanecarboxylic acid

<400> SEQUENCE: 75

Xaa Arg Ile Gly Glu Xaa Gly Thr Asp Pro Asn Leu Asn His Gln Gln
1               5                   10                  15

Phe Arg Xaa Lys Ile Leu Xaa Ile Trp Xaa Asp Pro
        20                  25

<210> SEQ ID NO 76
<211> LENGTH: 28
<212> TYPE: PRT
<213> ORGANISM: Artificial Sequence
<220> FEATURE:
```

```
<223> OTHER INFORMATION: Synthesized, unnatural polypeptide
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (25)..(25)
<223> OTHER INFORMATION: 3-aminopyrrolidine-4-carboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 76

Leu Gly Trp Arg Ile Gly Glu Xaa Gly Thr Asp Pro Asn Leu Asn His
1               5                   10                  15

Gln Gln Phe Arg Xaa Lys Ile Leu Xaa Ile Trp Xaa
            20                  25

<210> SEQ ID NO 77
<211> LENGTH: 27
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: 3-aminopyrrolidine-4-carboxylic acid
<220> FEATURE:
<221> NAME/KEY: MOD_RES
<222> LOCATION: (27)..(27)
<223> OTHER INFORMATION: 2-aminocyclopentanecarboxylic acid

<400> SEQUENCE: 77

Xaa Trp Arg Ile Gly Glu Xaa Gly Thr Asp Pro Asn Leu Asn His Gln
1               5                   10                  15

Gln Phe Arg Xaa Lys Ile Leu Xaa Ile Trp Xaa
            20                  25

<210> SEQ ID NO 78
<211> LENGTH: 29
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: 2-aminocyclopentanecarboxylic acid
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
```

<222> LOCATION: (22)..(22)
<223> OTHER INFORMATION: Aib
<220> FEATURE:
<221> NAME/KEY: MOD_RES
<222> LOCATION: (26)..(26)
<223> OTHER INFORMATION: 3-aminopyrrolidine-4-carboxylic acid
<220> FEATURE:
<221> NAME/KEY: MOD_RES
<222> LOCATION: (29)..(29)
<223> OTHER INFORMATION: 2-aminocyclopentanecarboxylic acid

<400> SEQUENCE: 78

Xaa Leu Gly Trp Arg Ile Gly Glu Xaa Gly Thr Asp Pro Asn Leu Asn
1               5                   10                  15

His Gln Gln Phe Arg Xaa Lys Ile Leu Xaa Ile Trp Xaa
            20                  25

<210> SEQ ID NO 79
<211> LENGTH: 29
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: 2-aminocyclopentanecarboxylic acid
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (22)..(22)
<223> OTHER INFORMATION: Aib
<220> FEATURE:
<221> NAME/KEY: MOD_RES
<222> LOCATION: (26)..(26)
<223> OTHER INFORMATION: 3-aminopyrrolidine-4-carboxylic acid
<220> FEATURE:
<221> NAME/KEY: MOD_RES
<222> LOCATION: (29)..(29)
<223> OTHER INFORMATION: 2-aminocyclopentanecarboxylic acid

<400> SEQUENCE: 79

Xaa Leu Gly Trp Cys Ile Gly Glu Xaa Gly Thr Asp Pro Asn Leu Asn
1               5                   10                  15

His Gln Gln Phe Arg Xaa Lys Ile Leu Xaa Cys Trp Xaa
            20                  25

<210> SEQ ID NO 80
<211> LENGTH: 29
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: 2-aminocyclopentanecarboxylic acid
<220> FEATURE:
<221> NAME/KEY: MOD_RES
<222> LOCATION: (22)..(22)
<223> OTHER INFORMATION: Aib
<220> FEATURE:
<221> NAME/KEY: MOD_RES
<222> LOCATION: (26)..(26)
<223> OTHER INFORMATION: 3-aminopyrrolidine-4-carboxylic acid
<220> FEATURE:
<221> NAME/KEY: MOD_RES
<222> LOCATION: (29)..(29)
<223> OTHER INFORMATION: 2-aminocyclopentanecarboxylic acid

<400> SEQUENCE: 80

Xaa Leu Gly Trp Arg Ile Gly Glu Cys Gly Thr Asp Pro Asn Leu Asn
1               5                   10                  15

His Gln Gln Phe Arg Xaa Cys Ile Leu Xaa Ile Trp Xaa
            20                  25

<210> SEQ ID NO 81
<211> LENGTH: 58
<212> TYPE: PRT
<213> ORGANISM: Homo sapiens

<400> SEQUENCE: 81

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 82
<211> LENGTH: 39
<212> TYPE: PRT
<213> ORGANISM: Homo sapiens

<400> SEQUENCE: 82

Val Glu Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Gly
        35

<210> SEQ ID NO 83
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (5)..(39)

<400> SEQUENCE: 83

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 84
<211> LENGTH: 39
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (5)..(39)

<400> SEQUENCE: 84

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 85
<211> LENGTH: 35
<212> TYPE: PRT
<213> ORGANISM: Artificial Sequence
<220> FEATURE:
<223> OTHER INFORMATION: Synthesized, unnatural polypeptide

<400> SEQUENCE: 85

Phe Asn Lys Glu Met Arg Asn Arg Tyr Trp Glu Ala Ala Leu Asp Pro
1               5                   10                  15

Asn Leu Asn Asn Gln Gln Lys Arg Ala Lys Ile Arg Ser Ile Tyr Asp
            20                  25                  30

Asp Pro Ser
        35

<210> SEQ ID NO 86
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (1)..(35)

<400> SEQUENCE: 86

Cys Asn Lys Glu Met Arg Asn Arg Tyr Trp Glu Ala Ala Leu Asp Pro
1               5                   10                  15

Asn Leu Asn Asn Gln Gln Lys Arg Ala Lys Ile Arg Ser Ile Tyr Asp
            20                  25                  30

Asp Pro Cys
        35

<210> SEQ ID NO 87
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (1)..(35)
<220> FEATURE:
<221> NAME/KEY: MOD_RES
<222> LOCATION: (1)..(1)
<223> OTHER INFORMATION: Homocysteine (Hey)
<220> FEATURE:
<221> NAME/KEY: MOD_RES
<222> LOCATION: (35)..(35)
<223> OTHER INFORMATION: Homocysteine (Hey)

<400> SEQUENCE: 87

Xaa Asn Lys Glu Met Arg Asn Arg Tyr Trp Glu Ala Ala Leu Asp Pro
1               5                   10                  15

Asn Leu Asn Asn Gln Gln Lys Arg Ala Lys Ile Arg Ser Ile Tyr Asp
            20                  25                  30

Asp Pro Xaa

```
<210> SEQ ID NO 88
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: DISULFID
<222> LOCATION: (9)..(38)
<220> FEATURE:
<221> NAME/KEY: MOD_RES
<222> LOCATION: (11)..(11)
<223> OTHER INFORMATION: 3-aminopyrrolidine-4-carboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 88

Val Asp Asn Lys Phe Asn Lys Xaa Cys Arg Xaa Arg Tyr Trp Glu Xaa
1               5                   10                  15

Ala Leu Asp Pro Asn Leu Asn Asn Gln Gln Lys Arg Xaa Lys Ile Arg
            20                  25                  30

Xaa Ile Tyr Xaa Asp Cys
        35

<210> SEQ ID NO 89
<211> LENGTH: 33
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (3)..(3)
<223> OTHER INFORMATION: 2-aminocyclopentanecarboxylic acid
<220> FEATURE:
<221> NAME/KEY: DISULFID
<222> LOCATION: (4)..(33)
<220> FEATURE:
<221> NAME/KEY: MOD_RES
<222> LOCATION: (6)..(6)
<223> OTHER INFORMATION: 3-aminopyrrolidine-4-carboxylic acid
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (28)..(28)
<223> OTHER INFORMATION: 3-aminopyrrolidine-4-carboxylic acid
<220> FEATURE:
```

```
<221> NAME/KEY: MOD_RES
<222> LOCATION: (31)..(31)
<223> OTHER INFORMATION: 2-aminocyclopentanecarboxylic acid

<400> SEQUENCE: 89

Asn Lys Xaa Cys Arg Xaa Arg Tyr Trp Glu Xaa Ala Leu Asp Pro Asn
1               5                   10                  15

Leu Asn Asn Gln Gln Lys Arg Xaa Lys Ile Arg Xaa Ile Tyr Xaa Asp
            20                  25                  30

Cys

<210> SEQ ID NO 90
<211> LENGTH: 30
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (1)..(30)
<220> FEATURE:
<221> NAME/KEY: MOD_RES
<222> LOCATION: (3)..(3)
<223> OTHER INFORMATION: 3-aminopyrrolidine-4-carboxylic acid
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (25)..(25)
<223> OTHER INFORMATION: 3-aminopyrrolidine-4-carboxylic acid
<220> FEATURE:
<221> NAME/KEY: MOD_RES
<222> LOCATION: (28)..(28)
<223> OTHER INFORMATION: 2-aminocyclopentanecarboxylic acid

<400> SEQUENCE: 90

Cys Arg Xaa Arg Tyr Trp Glu Xaa Ala Leu Asp Pro Asn Leu Asn Asn
1               5                   10                  15

Gln Gln Lys Arg Xaa Lys Ile Arg Xaa Ile Tyr Xaa Asp Cys
            20                  25                  30

<210> SEQ ID NO 91
<211> LENGTH: 33
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(33)

<400> SEQUENCE: 91

Asn Lys Glu Cys Arg Asn Arg Tyr Trp Glu Ala Ala Leu Asp Pro Asn
1               5                   10                  15

Leu Asn Asn Gln Gln Lys Arg Ala Lys Ile Arg Ser Ile Tyr Asp Asp
            20                  25                  30

Cys

<210> SEQ ID NO 92
<211> LENGTH: 35
<212> TYPE: PRT
<213> ORGANISM: Artificial Sequence
```

```
<220> FEATURE:
<223> OTHER INFORMATION: Synthesized, unnatural polypeptide
<220> FEATURE:
<221> NAME/KEY: DISULFID
<222> LOCATION: (1)..(35)
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid
<220> FEATURE:
<221> NAME/KEY: MOD_RES
<222> LOCATION: (32)..(32)
<223> OTHER INFORMATION: 2-aminocyclopentanecarboxylic acid

<400> SEQUENCE: 92

Cys Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Xaa
            20                  25                  30

Asp Pro Cys
        35

<210> SEQ ID NO 93
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (1)..(35)
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid

<400> SEQUENCE: 93

Cys Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Asp
            20                  25                  30
```

Asp Pro Cys
        35

<210> SEQ ID NO 94
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid
<220> FEATURE:
<221> NAME/KEY: MOD_RES
<222> LOCATION: (32)..(32)
<223> OTHER INFORMATION: 2-aminocyclopentanecarboxylic acid

<400> SEQUENCE: 94

Phe Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Xaa
            20                  25                  30

Asp Pro Ser
        35

<210> SEQ ID NO 95
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid

<400> SEQUENCE: 95

Phe Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Asp
            20                  25                  30

Asp Pro Ser
        35

<210> SEQ ID NO 96
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid

<400> SEQUENCE: 96

Phe Asn Lys Xaa Met Arg Xaa Arg Tyr Trp Xaa Ala Ala Leu Asp Pro
1               5                   10                  15

Asn Leu Asn Asn Gln Gln Lys Arg Xaa Lys Ile Arg Xaa Ile Tyr Asp
            20                  25                  30

Asp Pro Ser
        35

<210> SEQ ID NO 97
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid

<400> SEQUENCE: 97

Phe Asn Lys Xaa Met Arg Xaa Arg Tyr Trp Glu Xaa Ala Leu Asp Pro
1               5                   10                  15

Asn Leu Asn Asn Xaa Gln Lys Arg Xaa Lys Ile Arg Xaa Ile Tyr Asp
            20              25                  30

Asp Pro Ser
        35

<210> SEQ ID NO 98
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (4)..(4)
<223> OTHER INFORMATION: 2-aminocyclopentanecarboxylic acid
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid
<220> FEATURE:
<221> NAME/KEY: MOD_RES
<222> LOCATION: (33)..(33)
<223> OTHER INFORMATION: 2-aminocyclopentanecarboxylic acid

<400> SEQUENCE: 98

Phe Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Asp
            20              25                  30

Xaa Pro Ser
        35

<210> SEQ ID NO 99
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(35)
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid

<400> SEQUENCE: 99

```
Phe Asn Lys Cys Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Asp
            20                  25                  30

Asp Pro Cys
        35
```

<210> SEQ ID NO 100
<211> LENGTH: 35
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (4)..(35)
<220> FEATURE:
<221> NAME/KEY: MOD_RES
<222> LOCATION: (4)..(4)
<223> OTHER INFORMATION: Homocysteine (Hey)
<220> FEATURE:
<221> NAME/KEY: MOD_RES
<222> LOCATION: (7)..(7)
<223> OTHER INFORMATION: 3-aminopyrrolidine-4-carboxylic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (25)..(25)
<223> OTHER INFORMATION: Aib
<220> FEATURE:
<221> NAME/KEY: MOD_RES
<222> LOCATION: (29)..(29)
<223> OTHER INFORMATION: 3-aminopyrrolidine-4-carboxylic acid
<220> FEATURE:
<221> NAME/KEY: MOD_RES
<222> LOCATION: (35)..(35)
<223> OTHER INFORMATION: Homocysteine (Hey)

<400> SEQUENCE: 100

```
Phe Asn Lys Xaa Met Arg Xaa Arg Tyr Trp Glu Xaa Ala Leu Asp Pro
1               5                   10                  15

Asn Leu Asn Asn Gln Gln Lys Arg Xaa Lys Ile Arg Xaa Ile Tyr Asp
            20                  25                  30

Asp Pro Xaa
        35
```

<210> SEQ ID NO 101
<211> LENGTH: 16
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (1)..(1)
<223> OTHER INFORMATION: [2-(2-amino-ethoxy)-ethoxy]acetic acid
<220> FEATURE:
<221> NAME/KEY: MOD_RES
<222> LOCATION: (7)..(7)
<223> OTHER INFORMATION: Nle

<400> SEQUENCE: 101

```
Xaa Cys Asp Ile His Val Xaa Trp Glu Trp Glu Cys Phe Glu Arg Leu
1               5                   10                  15
```

<210> SEQ ID NO 102
<211> LENGTH: 58
<212> TYPE: PRT
<213> ORGANISM: Homo sapiens

<400> SEQUENCE: 102

```
Val Asp Asn Phe Lys Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 103
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: DISULFID
<222> LOCATION: (9)..(38)
<220> FEATURE:
<221> NAME/KEY: MOD_RES
<222> LOCATION: (11)..(11)
<223> OTHER INFORMATION: 3-aminopyrrolidine-4-carboxylic acid
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 103

```
Val Xaa Asn Lys Xaa Asn Lys Xaa Cys Gln Xaa Arg Phe Tyr Glu Xaa
1               5                   10                  15

Leu His Asp Pro Asn Leu Asn Glu Glu Gln Arg Asn Xaa Lys Ile Gln
            20                  25                  30

Xaa Ile Lys Xaa Asp Cys
        35
```

```
<210> SEQ ID NO 104
<211> LENGTH: 38
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: MOD_RES
<222> LOCATION: (2)..(2)
<223> OTHER INFORMATION: Beta-3 Asp
<220> FEATURE:
<221> NAME/KEY: MOD_RES
<222> LOCATION: (5)..(5)
<223> OTHER INFORMATION: Beta-3 Phe
<220> FEATURE:
<221> NAME/KEY: MOD_RES
<222> LOCATION: (8)..(8)
<223> OTHER INFORMATION: 2-aminocyclopentanecarboxylic acid
<220> FEATURE:
<221> NAME/KEY: DISULFID
<222> LOCATION: (9)..(38)
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (33)..(33)
<223> OTHER INFORMATION: 3-aminopyrrolidine-4-carboxylic acid
<220> FEATURE:
<221> NAME/KEY: MOD_RES
<222> LOCATION: (36)..(36)
<223> OTHER INFORMATION: 2-aminocyclopentanecarboxylic acid

<400> SEQUENCE: 104

Val Xaa Asn Lys Xaa Asn Lys Xaa Cys Gln Asn Arg Phe Tyr Glu Xaa
1               5                   10                  15

Leu His Asp Pro Asn Leu Asn Glu Glu Gln Arg Asn Xaa Lys Ile Gln
            20                  25                  30

Xaa Ile Lys Xaa Asp Cys
        35

<210> SEQ ID NO 105
<211> LENGTH: 34
<212> TYPE: PRT
<213> ORGANISM: Artificial Sequence
<220> FEATURE:
<223> OTHER INFORMATION: Synthesized, unnatural polypeptide
<220> FEATURE:
<221> NAME/KEY: DISULFID
<222> LOCATION: (5)..(34)

<400> SEQUENCE: 105

Phe Asn Met Gln Cys Gln Arg Arg Phe Tyr Ala Glu Leu His Asp Pro
1               5                   10                  15

Asn Leu Asn Glu Glu Gln Arg Asn Ala Lys Ile Lys Ser Ile Arg Asp
            20                  25                  30

Asp Cys

<210> SEQ ID NO 106
<211> LENGTH: 39
<212> TYPE: PRT
<213> ORGANISM: Artificial Sequence
<220> FEATURE:
<223> OTHER INFORMATION: Synthesized, unnatural polypeptide

<400> SEQUENCE: 106
```

```
Val Asp Asn Lys Phe Asn Lys Glu Met His Asn Ala Tyr Ala Ile Glu
1               5                   10                  15
Ile Ala Leu Leu Pro Asn Leu Asn Asp Gln Gln Phe His Ala Phe Ile
                20              25                  30
Trp Ser Leu Ile Asp Asp Pro
            35
```

α/β-PEPTIDE MIMICS OF Z-DOMAIN PEPTIDES

CROSS-REFERENCE TO RELATED APPLICATIONS

Priority is hereby claimed to provisional application Ser. No. 61/930,449, filed Jan. 22, 2014, which is incorporated herein by reference.

FEDERAL FUNDING STATEMENT

This invention was made with government support under GM056414 awarded by the National Institutes of Health. The government has certain rights in the invention.

BACKGROUND

Modulating protein-protein interactions represents an attractive goal both for probing protein function and for therapeutic applications. However, developing modulating agents using traditional small molecule-based approaches is quite challenging. This is due to the large and irregularly shaped interfaces inherent in protein-protein interactions. Because of their relatively large size and ability to mimic natural protein surfaces, synthetic peptides and proteins can be developed to bind target protein surfaces with high affinity and selectivity. However, peptides and proteins suffer from several significant disadvantages, in particular low bioavailability due to their rapid degradation by proteases. As a general proposition, proteolytic degradation of peptide pharmaceuticals limits the practical scope of their therapeutic use.

Various groups have sought to target large and complex protein-protein interaction interfaces using a variety of different classes of compounds, including peptides derived from phage display, antibody conjugates, nucleic acid aptamers, and rigid macrocyclic peptide scaffolds. In one recent example, mirror-image phage display was used to develop a D-peptide targeting vascular endothelial growth factor (VEGF). Although this approach yielded a 56-amino acid D-peptide that is anticipated to have decreased susceptibility to proteolytic degradation, it required the total chemical synthesis of the D-VEGF protein. This limits its general utility for developing inhibitors of other protein targets because it is not cost-effective (and for larger proteins, not possible) to fabricate the D-stereoisomer of a natural L-protein target.

It has been shown that peptide foldamers in which a subset of the residues contain backbone modifications in the form of β-amino acid residues α/β-peptides) can effectively mimic α-helices in the disruption of helix-mediated protein-protein interactions. Such oligomers can show high affinity and selectivity for target proteins and are less susceptible to proteolytic degradation than α-peptides composed exclusively of natural α-amino acid residues. Recently, it has also been shown that α/β-peptides can also have improved pharmacokinetic properties in vivo over their α-peptide counterparts, validating compounds of this type for potential therapeutic applications. See U.S. Pat. Publ. 2013/0177981, published Jul. 11, 2013.

Vascular endothelial growth factor (VEGF) is a soluble homodimeric protein which binds two cell-surface receptor tyrosine kinases, VEGFR1 and VEGFR2, to trigger receptor dimerization, phosphorylation, and intracellular signaling to initiate angiogenesis. Because of its critical role in angiogenesis, antagonists of the VEGF/VEGFR interaction are currently used in the treatment of both cancer and wet macular degeneration. The receptor recognition site on VEGF is large and topologically complex, with over 800 Å$^2$ of the surface of VEGF buried upon receptor binding. The receptor recognition site appears to be representative of many protein-protein interactions that interact primarily though flat, hydrophobic surfaces. α/β-Peptide analogs of phage-derived peptide v114 that bound VEGF with modest binding affinity ($K_i$=~2-5 μM in our fluorescence polarization (FP) assay), inhibited VEGF-induced proliferation of human umbilical vein endothelial cells (HUVECs) in culture, and had a reduced susceptibility to proteolytic degradation relative to the parent α-peptide have been reported in the literature. Haase, H. S.; Peterson-Kaufman, K. J.; Lan Levengood, S. K.; Checco, J. W.; Murphy, W. L.; Gellman, S. H. "Extending Foldamer Design beyond α-Helix Mimicry: α/β-Peptide Inhibitors of Vascular Endothelial Growth Factor Signaling. *J Am Chem Soc.* 2012, 134, 7652-5. However, because of v114's irregular conformation when bound to VEGF, the strategies employed for mimicry of this peptide are not general for mimicry of other protein-protein interaction inhibitors. Thus, there is a long-felt and unmet need for a method that can be widely applied to generate α/β-peptides to modulate a variety of different proteins of interest starting from peptides that bind to these proteins.

Protein-based affinity reagents derived from well-defined, non-immunoglobulin scaffolds offer an alternative to antibodies for selective and high affinity recognition of proteins in modulating protein-protein interactions, protein targeting, and imaging. The "Z-domain" scaffold derived from the domain B of staphylococcal protein A, is a relatively stable, three-helix bundle protein that presents a large "protein binding face" on helices 1 and 2. The protein binding face can be altered to selectively bind desired proteins using combinatorial approaches. The wild type Z-domain (Z-IgG, FIG. 1A) binds the Fc portion of IgGs. Randomization of up to 13 protein-contacting residues in helices 1 and 2 can be used to develop Z-domain peptides that bind a variety of different proteins. For example, a peptide adopting the Z-domain structure has been developed to bind HER2 (Z-HER2), a cell surface receptor overexpressed on many cancer cells. The Z-HER2 compound is useful for tumor targeting and diagnostic imaging and recently reported clinical data has validated its use for the imaging of breast cancer tumors in humans. Peptides derived from the Z-domain scaffold have also been developed to antagonize the binding of several soluble proteins such as VEGF and tumor necrosis factor-α (TNFα) to their cognate receptors (Z-VEGF and Z-TNFα, respectively, FIG. 1A). These compounds provide potential alternatives to antibodies for the selective therapeutic inhibition of their respective interactions or for analyte detection/capture. In 1998, the biotechnology company Affibody Biotechnology AB (Bromma, Sweden) was founded to develop Z-domain-based peptides for use as antibody alternatives. ("AFFIBODY" is a registered trademark in the United States for use in association with pharmaceutical preparations for the treatment of cancer and infectious diseases, and for diagnostic preparations or reagents for clinical and medical laboratory use.)

Two-helix analogs of the Z-IgG and Z-HER2 have been reported that stabilize the intended conformation with several α-amino acid substitutions and an interhelical disulfide bond. In the case of the two-helix Z-HER2 analog, the incorporation of helix-promoting 2-aminoisobutyric acid (Aib) residues throughout the sequence (which may be used to increase resistance to proteolytic degradation) lead to an 8000-fold decrease in binding affinity for HER2 relative to the full length Z-HER2. Incorporation of only two of these Aib substitutions lead to a high binding two-helix peptide, though this still bound HER2 with affinity weaker than the parent Z-domain. See, for example, U.S. Pat. No. 8,198,043, issued Jun. 12, 2012.

SUMMARY OF THE INVENTION

Disclosed herein are of α/β-peptide foldamers that mimic the Z-domain-derived peptides. In some versions, the Z-domain α/β-peptide foldamers disclosed herein are significantly smaller than the original, having only two helical domains as contrasted to the three-helix Z-scaffold itself. That is, some versions of the compounds disclosed herein are α/β-polypeptide sequences of the staphylococcal protein A, Z binding domain that exclude the third helix, adopt a conformation having only two helical domains, and demonstrate the ability to bind a polypeptide target selectively. In short, the subject compounds can be designed to retain their binding affinity for their protein targets, and have certain advantages over the original Z-domain scaffolds. Most notably they are easier to make (because of their smaller size), easier to modify, and easier to administer therapeutically. Importantly, the compounds described herein differ from previously described two-helix binding Z-domain mimics in that they contain β-amino acid residues, which significantly decrease the susceptibility of these compounds to degradation by proteases.

We describe the design of α/β-peptide foldamers that target the receptor recognition surface of VEGF by mimicking Z-VEGF, a VEGF-binding peptide derived from the Z-domain scaffold (FIGS. 1A and 1B). Starting from Z-VEGF, we developed truncated analogues containing non-natural residues scattered throughout their sequences that retain high affinity for VEGF. Our foldamers are roughly two-thirds the size of Z-VEGF (39 residues versus 59 residues), exhibit significantly decreased susceptibility to proteolysis relative to the original α-peptide, and are able to inhibit VEGF-induced proliferation of HUVECs. Furthermore, we show that the strategies that were ultimately successful for foldamer mimicry of the VEGF-binding Z-domain peptide can be extended to mimic other peptides based on the same scaffold, Z-IgG and Z-TNFα. Because Z-domain peptides can be developed via phage display to selectively bind to a variety of target proteins, we believe that the strategies presented here may be generalized to target many distinct protein-protein interactions.

Thus, disclosed herein are the following:

A method of making peptidomimetic affinity reagents. The method comprises generating a Z-domain scaffold peptide having affinity recognition and/or binding to a desired target compound. Then substituting at least one β-amino acid residue into at least one helical domain of the Z-domain scaffold peptide, thereby generating an α/β-peptide mimic of a Z-domain scaffold peptide. Optionally, at least one β-amino acid residue is cyclically constrained by a ring structure that incorporates the two methylene carbon atoms of the backbone of the β-amino acid residue (i.e., the alpha-position and beta-position carbon atoms). Additionally (and optionally) the Z-domain scaffold peptide may comprise three helical domains (designated helix 1, helix 2, and helix 3) wherein the method further comprising cleaving helix 3 from the α/β-peptide mimic, and wherein the at least one β-amino acid residue is substituted into helix 1 or helix 2. Note that the Z-domain scaffold peptide need not exhibit any specified secondary structure in solution and may be entirely devoid of helical domains.

Any of the methods described herein for making an α/β-peptide mimic of a Z-domain scaffold peptide may further comprise the optional step of forming at least one disulfide bond between two residues in the α/β-peptide mimic.

Also disclosed herein is a method of making peptidomimetic affinity reagents. The method comprises generating by any means now know or developed in the future an α/β-peptide mimic of a Z-domain scaffold. The α/β-peptide mimic of the Z-domain scaffold comprising no more than 60 amino acid residues, includes at least one β-amino acid residue, and has specific affinity recognition and/or binding to a desired target compound. As noted earlier, α/β-peptide mimic may optionally comprise at least one disulfide bond between two residues in the α/β-peptide mimic. In other words, the method may optionally comprise incorporating into the α/β-peptide mimic of a Z-domain scaffold at least two amino acid residues that are capable of forming a disulfide bridge between them and then forming a disulfide bond between the at least two amino acid residues. Again, the at least one β-amino acid residue may optionally be cyclically constrained by a ring structure that incorporates the two methylene carbon atoms of the backbone of the β-amino acid residue. If the α/β-peptide mimic of a Z-domain scaffold is sufficiently long (roughly 55 to 60 residues), it may optionally adopt three distinct helical domains in aqueous solution. (In all of the Z-domain scaffold peptide mimics disclosed herein, the helical domains may include one or more of the β-amino acid residues.) If the α/β-peptide mimic of a Z-domain scaffold is truncated, to roughly no more than 45 residues and it may optionally adopt only two distinct helical domains in aqueous solution.

Also disclosed herein is a method of inhibiting proteolytic degradation of Z-domain scaffold peptides. The method comprising: providing an α/β-peptide mimic of a Z-domain scaffold peptide in which at least one α-amino acid residue present in the Z-domain scaffold peptide is replaced with at least one β-amino acid residue. Optionally an unnatural α/β-peptide mimic having at least three β-amino acid residues is provided.

Further disclosed herein is a method of selectively delivering a therapeutic agent to a specific cell type or a specific tissue. The method comprising conjugating, binding, or linking the therapeutic agent to an α/β-peptide mimic of a Z-domain scaffold as recited in any one of Claims 13, 14, 15, or 16 to yield a mimic-agent conjugate, wherein the α/β-peptide mimic selectively binds to the specific cell type or the specific tissue, and then contacting the mimic-agent conjugate with the specific cell type or specific tissue. The method can be performed in vivo, ex vivo, or in vitro. For example, the method can be used to target therapeutic agents to neoplastic cells by conjugating a therapeutic agent to an α/β-peptide mimic of a Z-domain scaffold that binds selectively to a neoplastic cell.

Also disclosed herein are α/β-peptide mimics of a Z-domain scaffold peptide, the α/β-peptide mimics comprising from 40 to 60 amino acid residues, having no more than three distinct helical domains in aqueous solution, and wherein at least one of the amino acid residues is a β-amino acid residue, and salts thereof.

Additionally disclosed herein are α/β-peptide mimics of a Z-domain scaffold peptide, the α/β-peptide mimics comprising no more than 45 amino acid residues, having no more than two distinct helical domains in aqueous solution, wherein at least one of the amino acid residues is a β-amino acid residue, and including at least one disulfide bond, and salts thereof.

Further disclosed herein are α/β-peptide mimics of a Z-domain scaffold peptide, the α/β-peptide mimics comprising no more than 45 amino acid residues, having no more than two distinct helical domains, wherein at least one of the amino acid residues is a cyclically constrained β-amino acid residue, and including at least one disulfide bond, and salts thereof.

Also disclosed herein is a conjugate comprising an α/β-peptide mimic of a Z-domain scaffold as disclosed herein, which is conjugated, bound, or linked to a therapeutic agent. In this sense, "conjugated, bound, or linked" means that the α/β-peptide mimic of a Z-domain scaffold is operationally joined to the therapeutic agent so that the therapeutic agent can be delivered to a desired cell type or tissue type without vitiating the desired therapeutic action of the operationally joined therapeutic agent.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 1A: Sequences of several peptides derived from the Z-domain scaffold targeting different proteins. Helix 1, 2, and 3 are indicated by brackets. Residues on the protein-binding face of helix 1 and helix 2 that were randomized to derive binding to corresponding protein shown in red. FIG. 1B: Left: VEGF (grey) in complex with VEGFR1$_{D2}$ (orange) (PDB: 1QTY). Right: Z-VEGF (orange) bound to VEGF (PDB: 3S1K). FIG. 1C: Overall design strategy for development of α/β-peptides based on the Z-domain scaffold. Red residues indicate randomized residues that contact VEGF; helix 3 shown in teal; potential sites for non-natural residue replacement shown in dark blue.

FIG. 5. Sequences α/β-peptides designed to targeting the Fc portion of human IgGs based on Z-IgG. Residue notation is the same as FIG. 2.

FIG. 6. Sequences α/β-peptides designed to bind TNFα and inhibit its interaction with TNFR based on Z-TNFα. Residue notation is the same as FIG. 2.

FIG. 11. Various α→β-amino acid residue substitutions of α-VEGF-2 and their $K_i$ values.

FIGS. 15A, 15B, 15C, and 15D. Time-dependent proteolysis of peptides Z-VEGF ($t_{1/2}$=1.6 min.) (FIG. 15A), and α-VEGF-2 ($t_{1/2}$=0.20 min.) (FIG. 15B), and α/β-peptides α/β-VEGF-1 ($t_{1/2}$=59 min.) (FIG. 15C) and α/β-VEGF-2 ($t_{1/2}$=670 min.) (FIG. 15D) in 10 µg/mL proteinase K. All reactions carried out at 45 µM peptide in TBS, pH 7.5. Each condition was run in duplicate.

FIG. 18A: α/β-IgG-1-BSA conjugate with 30 µg/mL IgG1-κ. FIG. 18B. α/β-IgG-2-BSA conjugate with 10 µg/mL IgG1-κ. Filled markers represent signal when wells are incubated with the indicated amount of IgG1-κ. Unfilled markers indicate the signal when wells of immobilized peptide-BSA conjugates are incubated with no IgG1-κ. X's represent control wells in which no α/β-peptide has been immobilized.

FIG. 20A. Graph depicting results of blocking assay for α/β-TNFα-1 and α/β-TNFα-2, which block binding of TNF-α to immobilized tumor necrosis factor receptor (TNFR). FIG. 20B depicts $IC_{50}$ results for the compounds tested in FIG. 20A.

FIG. 21A: results for α/β-VEGF-1 and α/β-IgG-1. FIG. 21B: results for α/β-VEGF-1, α/β-IgG-1, and α/β-TNFα-1.

DETAILED DESCRIPTION

Abbreviations and Definitions

Figure 2:
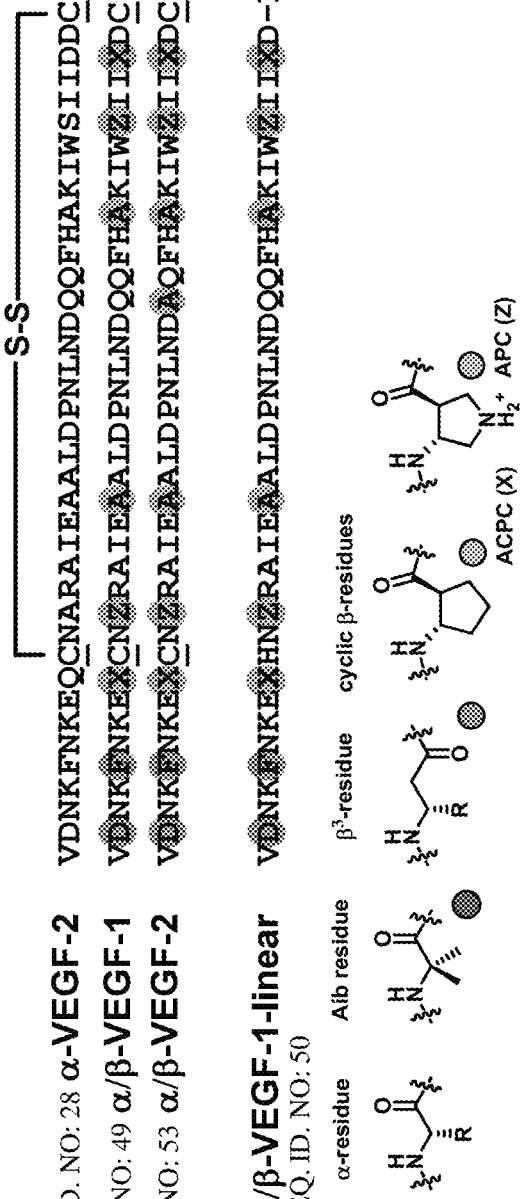
FIG. 2: Sequences of α- and α/β-peptides designed to target VEGF based on Z-VEGF. Oligomers containing cysteine residues (underlined) are cyclized via disulfide bonds. Colored circles indicate non-natural amino acid residues, as indicated in the structures shown. Green circles indicate Aib residues, blue circles indicate β³-residues, and tan circles indicate cyclic β-residues.

The term "amino acid" without qualification refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, O-phosphoserine, phosphothreonine, and phosphotyrosine. Categories of amino acids herein defined are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, in light of the detailed disclosure provided herein.

"Amino acid analog" refers to compounds that have the same basic chemical structure as a naturally occurring amino acid (i.e., a carbon that is bound to a hydrogen, a carboxyl group, and an amino group) including a non-conventional R group, (e.g., homoserine, norleucine, methionine sulfoxide, or methionine methyl sulfonium). Such analogs have modified R groups (e.g., norleucine) or modified peptide backbones (see definition of β-amino acids), but retain the same basic chemical structure as a naturally occurring amino acid.

ACPC=2-aminocyclopentanecarboxylic acid. APC=3-aminopyrrolidine-4-carboxylic acid. sAPC-N-succinyl-3-aminopyrrolidine-4-carboxylic acid.

"β-amino acids" are amino acid analogs having an extra methylene group. β-amino acids can be linked together to yield β-polypeptides:

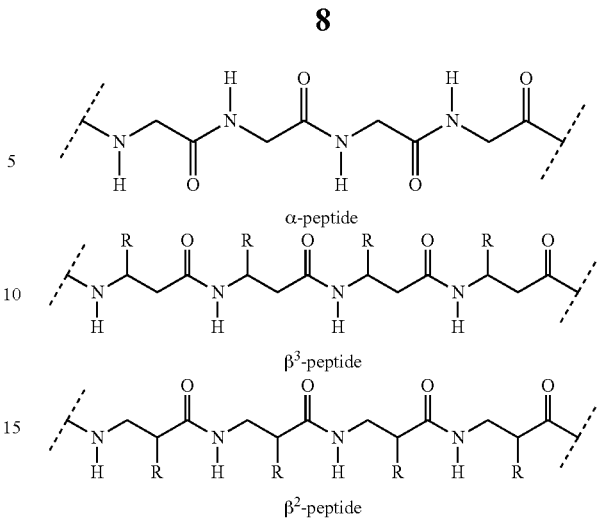

β-amino acids may be substituted at the $\beta^2$ and/or $\beta^3$ positions. The R groups may be the same as or different from the R groups found in the naturally occurring α-amino acids. Additionally, the two methylene carbon atoms in the backbone of a β-polypeptide may be incorporated into a rigidifying ring. See, for example, U.S. Pat. Nos. 6,060,585 and 8,642,536, both to Gellman et al.

As used herein, the term "binding" refers to the ability of a compound described herein to preferentially bind to a target with an affinity that is at least two-fold greater than its affinity for binding to a non-specific target (e.g., BSA or casein) other than the predetermined target or a closely-related target. The compounds disclosed herein preferably bind their respective targets with an affinity with a KD value less than about $5 \times 10^5 M^{-1}$, more preferably less than about $2 \times 10^7 M^{-1}$, and most preferably less than about $1 \times 10^8 M^{-1}$. Similarly, "specific binding" refers to the property of a binder to bind to a predetermined antigen with an affinity with a KD value less than about $2 \times 10^7 M^{-1}$.

The term "binding target" refers to any agent that may be bound by a α- or α/β-peptide. A binding target may include one or more of peptides, proteins (e.g., antibodies), nucleic acids (e.g., polynucleotides, DNA, RNA, or aptamers); polysaccharides (e.g., lectins or sugars), lipids, enzymes, enzyme substrates, ligands, receptors, antigens, or haptens. The target may include a discrete chemical moiety or a three-dimensional structural component (e.g., 3D structures that arises from peptide folding).

Amino acid sequence substitutions, deletions, or additions to a polypeptide or protein sequence that alter, add or delete a single amino acid or a small number (typically less than about 10% of amino acids) is a "conservative variant" where the alteration results in the substitution of an amino acid with a chemically similar amino acid. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

To detect binding of the α/β Z-domain mimic to its target, or for purposes of visualizing or modeling the interaction of a α/β Z-domain mimic to a target, the mimic may optionally be tagged or "labeled" with a molecular marker, label, or probe of any structure or configuration that can be detected by any means, both now known or developed in the future. The terms "marker," "label," and "probe," are used synonymously and include, without limitation, radioactive labels, fluorescent labels, chromophoric labels, affinity-based labels (such as antibody-type markers), and the like. Conventional radioactive isotopes used for detection include, without limitation, 32P, 2H and many others. A huge number of fluorescent and chromophoric probes are known in the art and commercially available from numerous worldwide suppliers, including Life Technologies (Carlsbad, Calif., USA), Enzo Life Sciences (Farmingdale, N.Y., USA), and Sigma-Aldrich (St. Louis, Mo., USA). For example, the α/β Z-domain mimics described herein are useful to inhibit specific protein-protein interactions, such as VEGF/VEGFR or TNFα/TNFR. The α/β Z-domain mimics described herein are also useful to target specific proteins, such as in imaging protocols or therapies designed to target a specific cell type or tissue type. For example, a label such as a fluorophore or a radiolabel, can be attached to an α/β Z-domain mimic that targets a protein that is overexpressed on a tumor surface (such as HER2 or EGFR). Fluorescence imaging, PET imaging, or autoradiographic imaging would then be used to detect the α/β Z-domain mimic localized specifically on that protein and thereby visualize the tumor.

PDB designates the Protein Data Bank, an online repository for three-dimensional structural data of large biological molecules, such as proteins and nucleic acids. The PDB is maintained by World Wide Protein Data Bank, http://www.wwpdb.org. See also H. M. Berman, K. Henrick, H. Nakamura (2003): Announcing the worldwide Protein Data Bank. *Nature Structural Biology* 10 (12), p. 980.

The polypeptide compounds disclosed herein may be prepared by synthetic chemical procedures, including procedures similar to those which may be used for the synthesis of polypeptides made exclusively from α-amino acid residues. Such procedures include both solution- and solid-phase procedures, e.g., using both Boc and Fmoc methodologies. Thus the subject polypeptides may be prepared by successive amide bond-forming procedures in which amide bonds are formed between the β-amino group of a first β-amino acid residue or a precursor thereof (or the amino group of a first α-amino acid or precursor) and the α-carboxyl group of a second β-amino acid residue or a precursor thereof (or the amino group of a second α-amino acid or precursor). The amide bond-forming step may be repeated as many times, and with specific α-amino acid residues and/or β-amino acid residues and/or precursors thereof, as required to give the desired final polypeptide. Solid-phase and liquid-phase methods of linking amino acid monomers to yield polypeptides are well known and will not be discussed in detail. See, for example, "Peptide Synthesis and Applications (Methods in Molecular Biology)," John Howl (Editor), ISBN-13: 978-1617374906, © 2010 Humana Press, Totowa, N.J. USA; "Fmoc Solid Phase Peptide Synthesis: A Practical Approach," W. C. Chan and Peter D. White (Editors) ISBN-13: 978-0199637249, © 2000 Oxford University Press, Inc. NY, USA. See the Examples for detailed experimental procedures.

Many β-amino acid monomers are available commercially. β-amino acids may also be produced enantioselectively from corresponding α-amino acids; for instance, by Arndt-Eisert homologation of N-protected α-amino acids. Conveniently such homologation may be followed by coupling of the reactive diazo ketone intermediate of the Wolff rearrangement with a β-amino acid residue.

A "pharmaceutically-suitable salt" is any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like.

A "protecting group" refers to a chemical moiety that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions from which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Carbamate-, sulfonamide-, sulfamate-, and ammonium-forming protecting groups may all be used. The term "protecting group" explicitly includes, without limitation t-butoxycarbonyl (tBOC), benzyloxycarbonyl (Cbz), benzyl (Bn), and allyloxycarbonyl (alloc). A "protected amine" is an amine moiety protected by a "protecting group." A "protected caboxy" is a carboxy moiety protected by a "protecting group." A host of suitable amine-protecting and carboxy-protecting groups, and how to use them, are known in the art. For a comprehensive guide to techniques for forming and cleaving protecting groups, see Greene & Wuts, "Greene's Protective Groups in Organic Synthesis," Fourth Edition,"© 2006, Wiley-Interscience/John Wiley & Sons, New York, N.Y. (ISBN-13: 978-0471697541).

When referring to a chemical moiety, the phrase "substituted or unsubstituted" means that the chemical moiety may appear as the basic unsubstituted moiety (e.g., a linear alkyl group having no other pendant moieties), or the chemical moiety is substituted with one or more additional substituents, e.g., alkyl, halogen, alkoxy, acyloxy, amino, hydroxy, mercapto, carboxy, benzyl, etc.

As used herein, the term "Z-domain scaffold peptide," without qualification, refers to an isolated polypeptide, derived from the Z domain (the immunoglobulin G-binding domain) of Staphylococcal protein A, and which, when left unmodified, consists essentially of three distinct alpha-helical domains (designated helix 1, helix 2, and helix 3) and which binds to the Fc portion of IgG's. This specific unmodified Z-domain scaffold peptide is also referred to herein as "Z-IgG." The phrase "Z-domain scaffold peptide," also encompasses peptides comprised exclusively of α-amino acid residues which are derived from Z-IgG through randomization of residues on the protein-binding faces of helix 1 and helix 2. Unmodified Z-domain scaffold peptides consist entirely of α-amino acid residues, consist essentially of from about 55 to about 60 total amino acid residues (typically 58), exhibit three distinct alpha-helical domains in aqueous solution, and lack disulfide bridges. As used herein the term "α/β-peptide mimics of Z-domain peptides" refers to isolated polypeptides, analogous to (and/or homologous to) the Z domain of protein A, that comprise at least one β-amino acid residue (and more preferably at least 2, 3, 4, 5, 6, 7, 8, 9, 10, 11, 12, 13, 14, or 15 β-amino acid residues), have from about 25 to about 60 total amino acid residues (or 45 to 59 total amino acid residues), optionally comprise at least one disulfide bridge (and/or 2, 3, 4 or more), and exhibit zero, one, two, or three distinct helical domains in aqueous solution.

Truncation of Z-VEGF and the Design of VEGF-Binding α/β-Peptides

We previously described α/β-peptide mimicry of the phage display-derived peptide v114, which binds to the receptor-binding region of VEGF in an irregular (yet defined) conformation. Holly S. Haase, Kimberly J. Peterson-Kaufman, Sheeny K. Lan Levengood, James W. Checco, William L. Murphy, and Samuel H. Gellman (May 2012) "Extending Foldamer Design Beyond A-Helix Mimicry: A/B-Peptide Inhibitors Of Vascular Endothelial Growth Factor Signaling," *J Am Chem Soc.* 134(18): 7652-7655. While several individual α→β-amino acid substitutions were tolerated in v114 analogs, the incorporation of multiple β-amino acid residues had a cumulative detrimental effect on binding affinity for VEGF. This suggests that the irregular conformation v114 and its analogs must adopt to bind VEGF is negatively perturbed by the incorporation of multiple additional methylene units when making α→β-amino acid substitutions.

In this disclosure Z-VEGF was chosen as the starting point for mimicry by α/β-peptides. Z-VEGF is a 59-amino acid phage-derived peptide developed by Fedorova et al. based on the Z-domain scaffold by randomizing nine (9) residues on the protein-binding face of helices 1 and 2 of the Z-domain scaffold and selecting for binding to VEGF. Fedorova A, Zobel K, Gill H S, Ogasawara A, Flores J E, Tinianow J N, Vanderbilt A N, Wu P, Meng Y G, Williams S P, Wiesmann C, Murray J, Marik J, Deshayes K (July 2011) "The development of peptide-based tools for the analysis of angiogenesis, *Chem Biol.* 18(7):839-45. The Z-VEGF:VEGF co-crystal structure shows that this peptide binds VEGF in the receptor binding region with high affinity (0.038 μM by Octet analysis, 0.41 μM in our solution fluorescence polarization assay; see Table 1) and adopts the well-defined structure made up of three α-helices that is characteristic of peptides derived from the Z-domain (FIG. 1B). The protein-binding face containing the randomized residues on helices 1 and 2 make contact with VEGF, as designed. Of particular note, during the selection process an alanine residue (Ala14) was unintentionally incorporated into the peptide, shifting the register of several residues in helix 1 by one amino acid position relative to the native Z-IgG and other Z-domain peptides.

TABLE 1

Binding of oligomers to VEGF and proteolysis data:

| Oligomer | $K_i$ (μM)[a] | $t_{1/2}$ (min)[b] |
|---|---|---|
| Z-VEGF | 0.41 | 1.6 |
| Z-VEGF (1-38) | >100 | — |
| α-VEGF-1 | >100 | — |
| α-VEGF-2 | 0.42 | 0.20 |
| α/β-VEGF-1 | 0.11 | 59 |
| α/β-VEGF-2 | 0.38 | 670 |
| α/β-VEGF-1-linear | >50 | — |

[a]$K_i$ values for VEGF binding determined by competition FP assay.
[b]Half-life of 45 μM α-peptide or α/β-peptide in the presence of 10 μg/mL proteinase K in TBS, pH 7.5

Because Z-VEGF is predominantly α-helical, it was hypothesized that it might tolerate α→β-amino acid residue substitutions better than v114. Furthermore, because the VEGF-binding residues of Z-VEGF are isolated to helices 1 and 2 of the peptide, it was further hypothesized that removal of helix 3 could lead to a truncated two-helix peptide that retains binding affinity for VEGF (FIG. 1C). In the present work, the removal of helix 3 may be beneficial for three primary reasons: First, the shorter length brings this peptide into a range more amenable to synthetic approaches (roughly 39 amino acids versus 59 for the full length Z-VEGF), which is important for oligomers containing unnatural residues that cannot be produced through recombinant expression or the incorporation of specific modifications such as fluorescent labeling or conjugation. Second, removal of helix 3 provides a region opposite the protein-binding face where non-natural amino acid substitutions can be rationally incorporated for the purpose increasing the oligomer's structural stability and decreasing its susceptibility to proteolytic degradation without making changes to the protein-binding face of helices 1 and 2 (FIG. 1C, second arrow). Finally, a protease-resistant VEGF antagonist with MW≤5000 is able to move passively across the sclera of the eye, providing a new therapeutic approach to treat wet macular degeneration. The target two-helix structure would be below this molecular weight limit, and so compounds of this type are administrable via eye drops. This represents an alternative to the currently used anti-VEGF therapies which involve injection of an engineered protein into the eye. The target two-helix peptide presents a protein-binding face larger than a single helix, but it has been found that the high helical content of this oligomer can accommodate substitution with helix-promoting residues such as cyclically constrained β-amino acid and/or Aib residues.

In addition to Z-VEGF, Fedorova et al. reported a VEGF-binding two-helix peptide derived from randomization of nine residues of the two-helix Z-IgG analog, selecting for binding to VEGF. The resulting two-helix peptide, termed Mini-Z-1, did bind VEGF with an affinity constant similar to that of the full-length Z-VEGF. However, the Mini-Z-1: VEGF co-crystal structure showed that this peptide required homodimerization to bind VEGF, showing that the randomization process lead to an alternative mode of binding by Mini-Z-1 than that which was desired. In the present work, it was therefore decided to truncate the longer Z-VEGF peptide rather than use Mini-Z-1 as a starting point for α→β-residue replacement. By keeping the residues that appear to bind VEGF in the Z-VEGF:VEGF co-crystal structure intact, it was hypothesized that the presently disclosed compounds would retain the same binding mode as the Z-VEGF peptide through the face of helices 1 and 2.

Removal of helix 3 from Z-VEGF to give Z-VEGF(1-38) resulted in a complete loss of binding to VEGF, as determined by competition fluorescence polarization assay. See FIG. 2 and Table 1. This is consistent with the loss of binding affinity seen for both Z-IgG and Z-HER2 upon removal of helix 3. In the development of the two-helix Z-IgG analog, several amino acid substitutions were identified using phage display that recovered binding affinity after truncation and were thought to stabilize the desired two-helix structure in the absence of helix 3. Incorporation of five of these substitutions not thought to be involved in the binding interface into the two-helix HER2-binding Z-domain peptide analog was adequate to recover binding affinity to HER2 after a loss of binding following the removal of helix 3. However, the incorporation of these same substitutions into Z-VEGF(1-38), along with the Met9→Gln substitution to avoid the presence of the oxidation-prone methionine residue, to give α-VEGF-1 did not recover binding to VEGF. (Note that the Ala→Arg substitution in the two-helix Z-IgG and Z-HER2 case corresponds to the Tyr→Arg substitution for Z-VEGF; this discrepancy is due to the register shift brought about by the extra Ala in Z-VEGF relative to other Z-domains.) Although α-VEGF-1 did not show affinity for VEGF, this peptide did display noticeably increased aqueous solubility relative to Z-VEGF(1-38), likely due to the substitution of a number of hydrophobic residues for charged residues on the face opposite the VEGF-binding face, and so these substitutions were retained moving forward.

Stabilizing the desired two-helix structure can be used to recover binding after the removal of helix 3 from Z-VEGF. Inspired by the increase in binding affinity seen for the previously described two-helix designs, it was hypothesized that the incorporation of a disulfide bond to connect the ends of the two helices would promote the adoption of the correct structure and orient the VEGF-binding residues in a manner that allows for binding to the receptor-binding region. By aligning helix 1 and helix 2 of Z-VEGF from the crystal structure with the reported NMR structure of the two-helix Z-IgG analog, two sites were identified for replacement with cysteine (His10 in helix 1 and Pro39 in helix 2) that could form a disulfide bond to constrain the termini of helices 1 and 2 in close proximity to one another, promoting the intended two-helix conformation. Incorporation of the His10→Cys and Pro39→Cys substitutions followed by oxidation to form an intramolecular disulfide bond lead to α-VEGF-2, which did indeed recover binding affinity for VEGF ($K_i$=0.42 μM). α-VEGF-2 is 39-amino acids in length, binds VEGF with a $K_i$ indistinguishable from that of the full length Z-VEGF, and is anticipated to adopt the structure of helices 1 and 2 of Z-VEGF.

After developing α-VEGF-2 as a potent two-helix VEGF-binding peptide, attempts were made to incorporate non-natural residues (e.g., β-amino acid residues) into this peptide with the goals of further stabilizing the VEGF-binding conformation and decreasing the susceptibility of this oligomer to proteolytic degradation. α-VEGF-2 is designed to adopt a conformation similar to the first two helices of Z-VEGF and thus has four conformationally distinct regions that must be mimicked: Residues 1-6 do not appear in the Z-VEGF:VEGF co-crystal structure and so their conformation when bound to VEGF is unknown. Residues 7-20 make up helix 1 of the peptide. Residues 21-24 make up a loop region containing stabilizing hydrophobic and hydrogen bonds, and residues 25-39 make up helix 2.

Figure 13:
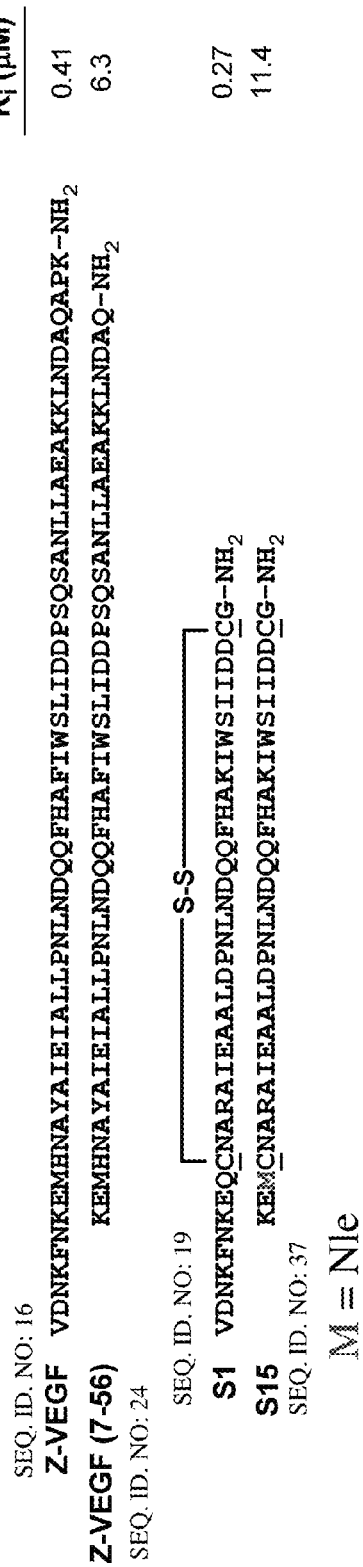
FIG. 13. Sequence for Z-VEGF and Z-VEGR (7-56) (i.e., 6-residue N-terminal truncation), S1 and S15. (Note: The S1, S15 designation here is as depicted in FIG. 11. Appendix A describes these and several additional supplemental sequences with different designations.)
Figure 14:
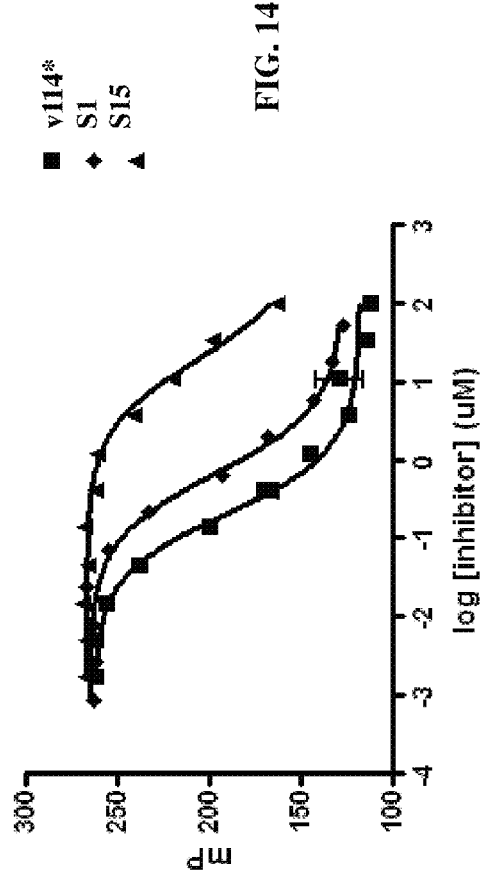
FIG. 14. A representative VEGF competition FP assay with S1 and S15 as shown in FIG. 13.

It has previously been shown that β-amino acid residues containing cyclic ring constraints (e.g., ACPC and APC) can enhance the folding propensity of helical α/β-peptides by constraining the Cα-Cβ backbone torsion. Using an iterative design strategy in which several sites were probed for tolerance to substitution by cyclically-constrained β-amino acid residues or the helix-promoting Aib residue, the compound α/β-VEGF-1 was made. α/β-VEGF-1 is an α/β-peptide which comprises non-natural β-amino acid residues throughout helix 1, helix 2, and the N-terminal six residues, and binds VEGF with a $K_i$=0.11 μM. (See FIG. 11, Examples, and Appendix A, attached hereto and incorporated herein for a detailed explanation of the strategy by which α/β-VEGF-1 was developed.) Because residues 1-6 are not present in the Z-VEGF:VEGF co-crystal structure, the conformation of these residues when bound to VEGF are unknown. Interestingly, these residues seem to be required for high binding affinity (see FIGS. 13 and 14). In order to reduce this region's susceptibility to proteolysis without removing the original side chains, two α→β³-amino acid residue substitutions were made (Asp2→β³Asp and Phe5→β³Phe). α/β-VEGF-1 contains a stretch of non-Aib α-amino acid residues from Ala18 to His29 which may be susceptible to proteolytic degradation. In order to protect this region from proteolytic degradation, α/β-VEGF-2 was designed. This compound contains additional Gln26Aib substitution at the N-terminus of helix 2. Gln26 is a residue that was randomized in the development of Z-VEGF and the side chain of this residue appears to make some contact with the VEGF protein in one molecule of the asymmetric unit of the Z-VEGF:VEGF co-crystal, while it does not in the other molecule. Despite this, it was found that α/β-VEGF-2 binds VEGF with a $K_i$=0.38 μM in our FP assay, which is experimentally indistinguishable from that of Z-VEGF. Residues in the loop region (Pro21 to Asn24) appear to be taking part in several hydrophobic and hydrogen bonding interactions within both helix 1 and helix 2. These may be important for overall stability of the two-helix structure, and so no substitutions were made in this region.

Using primarily rational design, two high-affinity VEGF-binding α/β-peptides were developed, α/β-VEGF-1 and α/β-VEGF-2, that are approximately two-thirds the length of the starting peptide (Z-VEGF), cyclized through a disulfide bond, and contain non-natural residues spaced throughout their sequences. α/β-VEGF-1 and α/β-VEGF-2 represent the first examples of a mimicry by α/β-peptides in which the final oligomers are designed to adopt a helix bundle rather than an extended helical structure. Unlike the efforts to mimic v114, the incorporation of helix-promoting non-natural residues (cyclic β-amino acid and Aib residues) was not detrimental to the binding affinity of these oligomers for VEGF. In the case of α/β-VEGF-1, the binding affinity was modestly improved over both Z-VEGF and α-VEGF-2, presumably because the incorporated non-natural residues are helix-promoting and rigidify the backbone into the helical conformation required for binding to VEGF.

Figure 3:
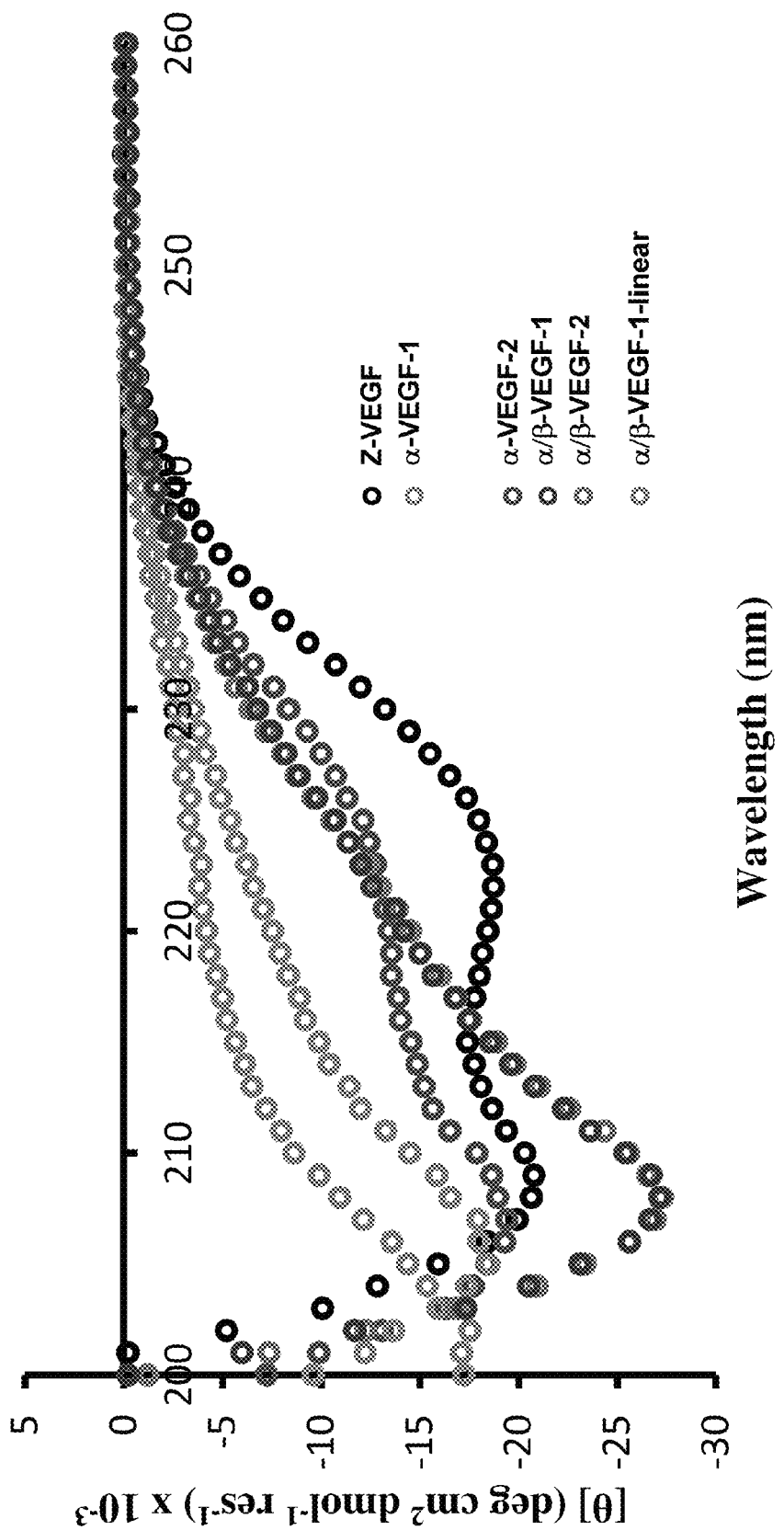
FIG. 3. Far-UV circular dichroism data for α- and α/β-peptides targeting VEGF based on Z-VEGF. All oligomers 75 µM in PBS, pH 7.5, 20° C.

Structural Analysis of Oligomers in Solution Using Circular Dichroism:

Examining the far-UV circular dichroism (CD) spectrum of Z-VEGF reveals that this peptide is predominately α-helical in solution, consistent with the structure observed when bound to VEGF in the co-crystal structure and of other peptides derived from the Z-domain (FIG. 3). Z-VEGF(1-38) is insoluble in PBS at 75 μM, which precluded obtaining CD spectra of this peptide. The spectra of Z-VEGF(1-38) at lower concentrations (50 μM and 25 μM) displayed a single broad minimum and ~210-213 nm, indicating aggregation in solution at these concentrations (data not shown). In contrast, α-VEGF-1, which contains six α-amino acid substitutions relative to Z-VEGF(1-38), three of which add charged residues, is fully soluble at 75 μM. The far-UV CD spectrum of α-VEGF-1 indicates that this peptide is unstructured in solution. Together, the CD spectrum and VEGF FP data indicate that helix 3 of Z-VEGF is necessary for stabilizing the secondary and tertiary structure that is required for high affinity binding. This is consistent with the results obtained for the development of the two-helix analogs of Z-IgG and Z-HER2.

The far-UV CD spectrum of α-VEGF-2 shows that this peptide contains higher helical content in solution than α-VEGF-1, indicating that the disulfide bond is promoting the adoption of a helical structure, as designed. α/β-VEGF-1 and α/β-VEGF-2 show a single intense minimum at 208 nm, which is characteristic of α/β-peptides that adopt a predominantly helical structure. α/β-VEGF-1-linear, an analog of α/β-VEGF-1 lacking the disulfide bond, shows a less intense minimum at 208 nm than α/β-VEGF-1. Consistent with this, α/β-VEGF-1-linear shows essentially no binding to VEGF ($K_i$>50 μM, Table 1), suggesting that the incorporation of helix promoting residues alone is not sufficient to constrain these oligomers in the conformation required for binding.

Proteolytic Susceptibility of Oligomers:

To examine the impact of non-natural residue incorporation on the relative susceptibility of the Z-scaffold α/β-peptides to proteolytic degradation, a subset of oligomers was evaluated in a protease digestion assay (Table 1). When incubated with proteinase K, a promiscuous and aggressive protease, it was found that Z-VEGF was rapidly degraded. HPLC analysis of peptide degradation over time showed that Z-VEGF has a half-life of 1.6 minutes under the assay conditions. α-VEGF-2, the two-helix, disulfide constrained peptide which bound VEGF with affinity indistinguishable to that of Z-VEGF, had a half-life of 0.20 minutes, with essentially complete degradation by the 1 minute time point. The over 7-fold increase rate of digestion by proteinase K for α-VEGF-2 relative to Z-VEGF likely arises from the decreased conformational stability of α-VEGF-2, consistent with the previously reported decrease in thermal stability of the two-helix Z-IgG analog relative to the full-length Z-IgG (Starovasnik PNAS 1997). In contrast, α/β-VEGF-1, which contains six β-amino acid residues and two Aib residues, has a half-life of 59 minutes, an over 36-fold increase relative to Z-VEGF and an over 290-fold increase relative to α-VEGF-2, the peptide from which it was directly derived. The half-life of α/β-VEGF-2, which contains one additional Aib residue relative to α/β-VEGF-1, has a half-life of 670 minutes, representing an over 400-fold increase relative to Z-VEGF and an over 3300-fold increase relative to α-VEGF-2.

These results indicate that truncation of Z-domain peptides down to the two-helix structure increases the susceptibility of these peptides to proteolytic degradation, even in the presence of the structurally stabilizing disulfide bond. Non-natural amino acid incorporation significantly decreases the susceptibility of these peptides to proteolytic degradation relative to both the parent minimized peptide and the full length Z-domain peptide without a loss of binding affinity for the protein target. The α/β-peptides disclosed herein are thus both shorter and significantly less susceptible to proteolytic degradation than the full-length Z-domain peptides and bind their protein target (VEGF) with binding affinity greater than or equal to the parent Z-domain peptide.

Figure 4:
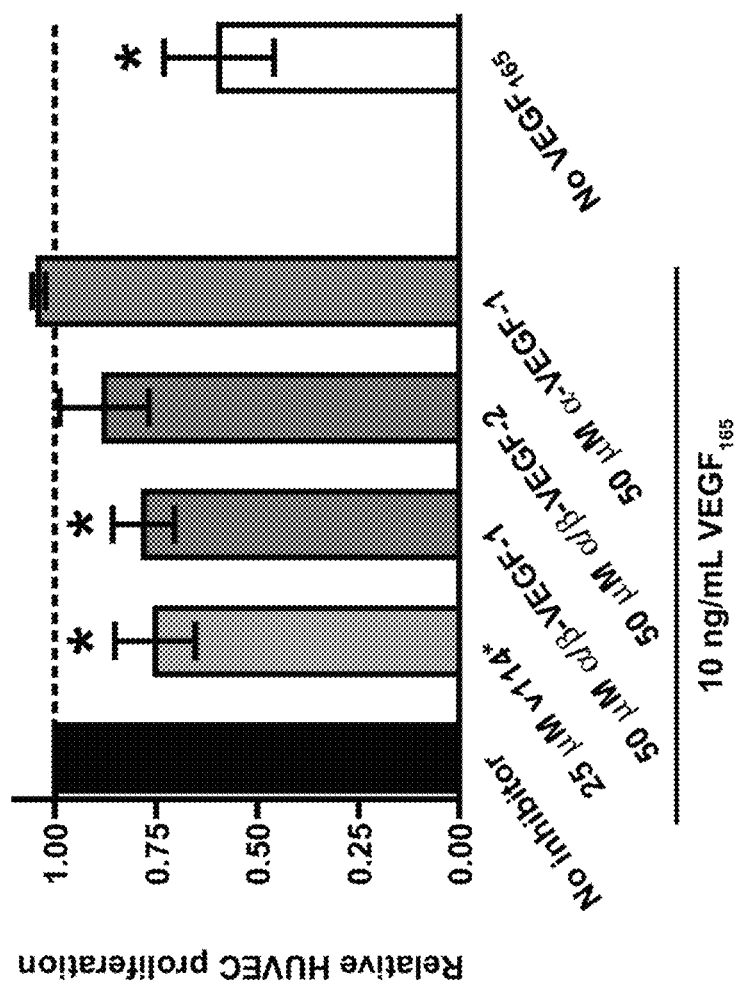
FIG. 4. Proliferation of HUVECs after treatment with 10 ng/mL VEGF$_{165}$ and the indicated concentration of inhibitor: v114* (positive control, n=6), α/β-VEGF-1 (n=7), α/β-VEGF-2 (n=6), or α-VEGF-1 (n=3). Each bar represents the mean±SD collected from eight independent experiments. Data from each experiment were normalized to the respective "No inhibitor" control condition treated with VEGF$_{165}$ only (black bar, dotted line). White bar indicates relative levels of proliferation when no exogenous VEGF$_{165}$ is added (n=8). Statistical differences are denoted for p-value≤0.01 (*) relative to "No inhibitor" (VEGF$_{165}$ only) control using a two-tailed ratio t-test.
Figures 7A, 7B:
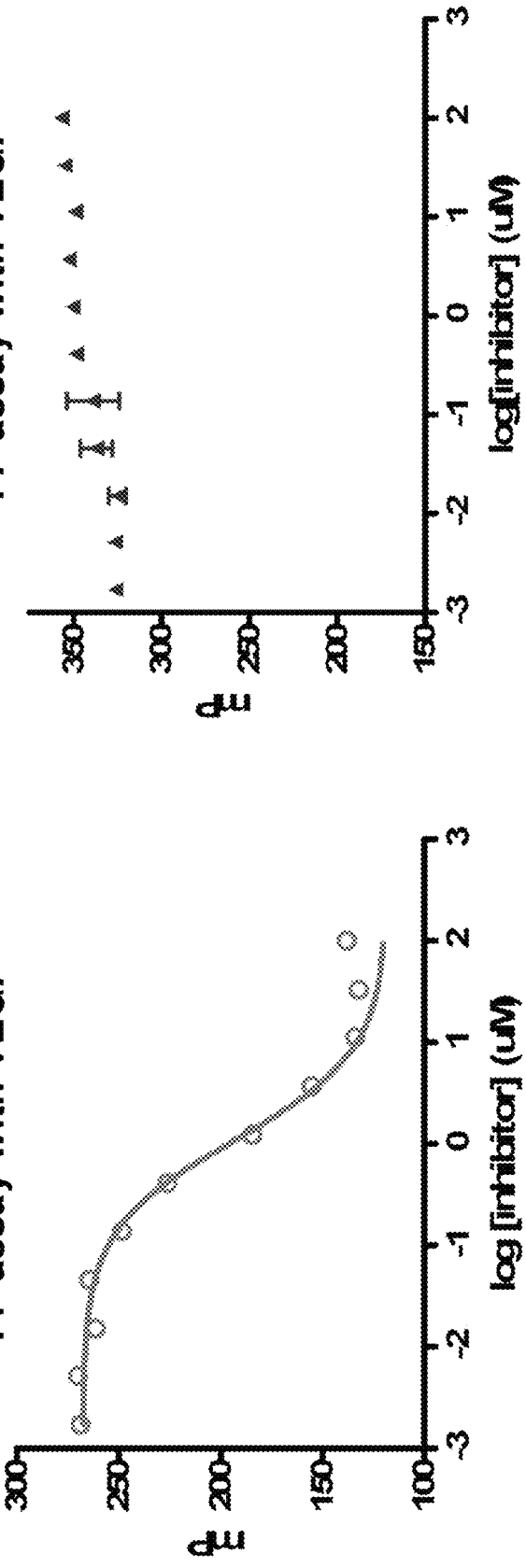
FIG. 7A. A representative Z-VEGF competition FP assay with VEGF.
FIG. 7B. A representative Z-VEGF (1-38) competition FP assay with VEGF.
Figure 8:
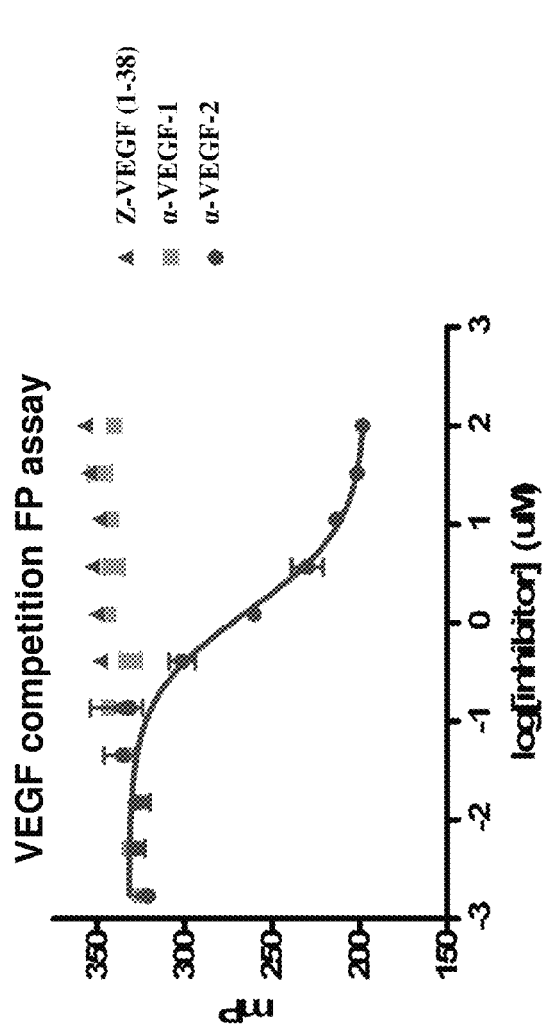
FIG. 8. A representative VEGF competition FP assay showing that incorporating disulfide bridges and solubilizing substitutions recovers VEGF binding.
Figure 9:
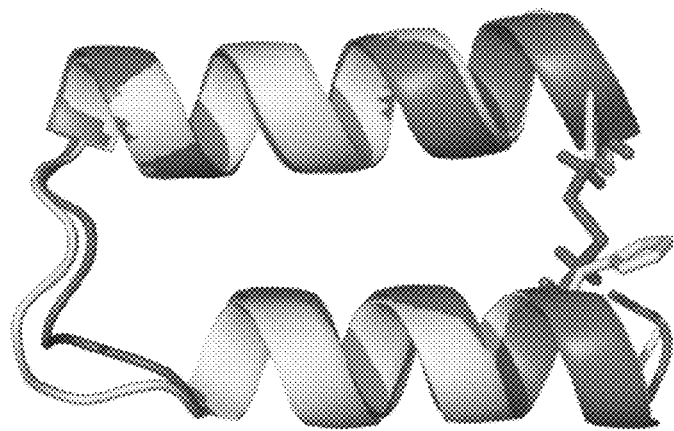
FIG. 9. Overlay of helices 1 and 2 of Z-VEGF (yellow, PDB: 3S1K) with the two-helix analog of Z-IgG, called Mini-Z (red, PDB: 1ZDC), disulfide bond is shown as sticks. The location of Cys residues in Mini-Z overlays very well with the His and Pro residues of Z-VEGF, indicating the correct positioning for a disulfide bond in the desired two-helix structure.
Figures 10A, 10B:
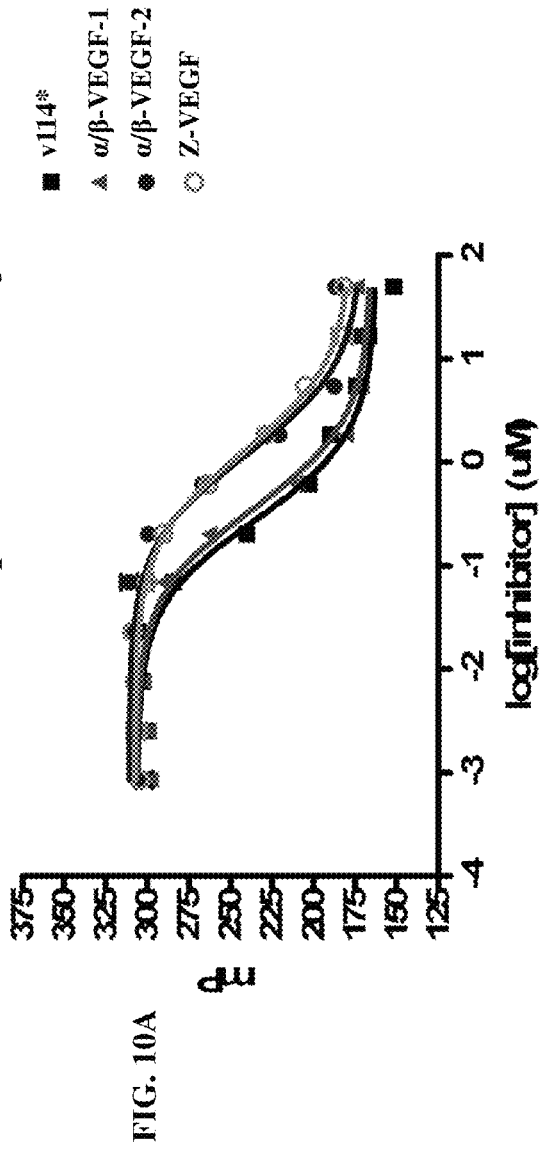
FIG. 10A. A representative competition FP assay (replicate 4 in FIG. 10B) showing the binding of α/β-VEGF-1 (red), α/β-VEGF-2 (blue), v114* (black), and Z-VEGF (orange) on the same plate. Each condition in this assay was run in duplicate.
FIG. 10B. Representative results of several replicate competition FP assays for α/β-VEGF-1 and α/β-VEGF-2 with v114* and Z-VEGF for comparison.
Figure 12:
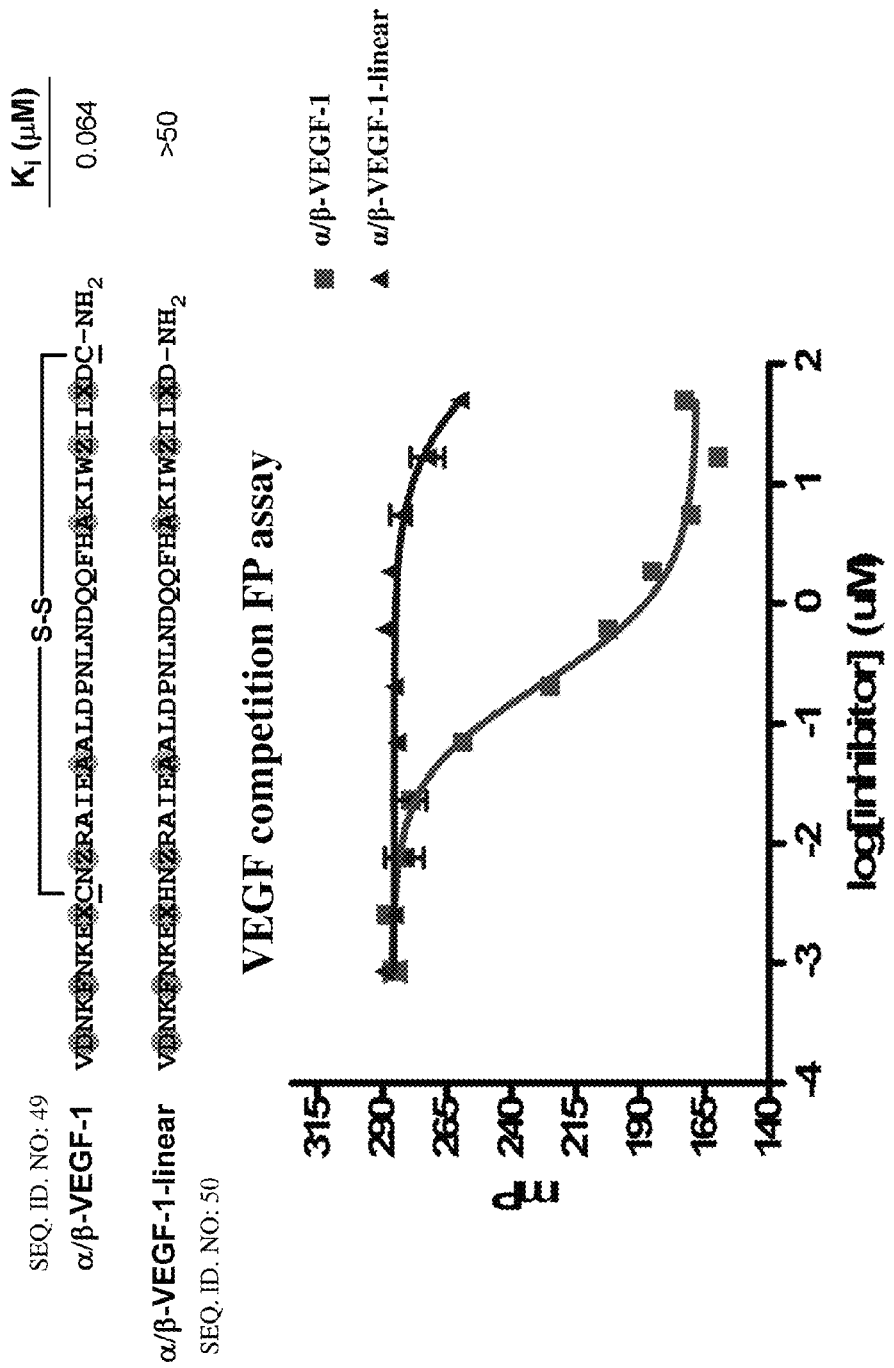
FIG. 12. A representative VEGF competition FP assay illustrating that a disulfide bond yields high binding affinities for two-helix α/β-peptide mimics of Z-VEGF.

Inhibition of VEGF-Induced HUVEC Proliferation:

The ability of Z-scaffold α/β-peptides to antagonize the VEGF-mediated proliferation of human umbilical vein endothelial cells (HUVECs) was assessed in cell culture. α/β-VEGF-1 and α/β-VEGF-2 at 50 μM were both able to inhibit VEGF-induced HUVEC proliferation relative to VEGF-only conditions without inhibitor (FIG. 4). The results for α/β-VEGF-2 (pooled data from 6 duplicate runs), however, were not statistically significant. This is consistent with the results showing α/β-VEGF-2 has a lower affinity for VEGF than does α/β-VEGF-1 in the competition FP assay.

As a positive control, α-peptide v114*, an analog of v114 which has previously been shown to be a potent inhibitor in this assay (Haase JAGS 2012), inhibited proliferation to about the same relative levels at 25 μM. As a negative control, α-VEGF-1, an α/β-peptide similar in sequence to α/β-VEGF-1 but does not bind VEGF, does not show any inhibition of HUVEC proliferation at 50 μM. The data presented in FIG. 4 are the pooled results of eight (8) independent experiments.

Figures 16A, 16B:
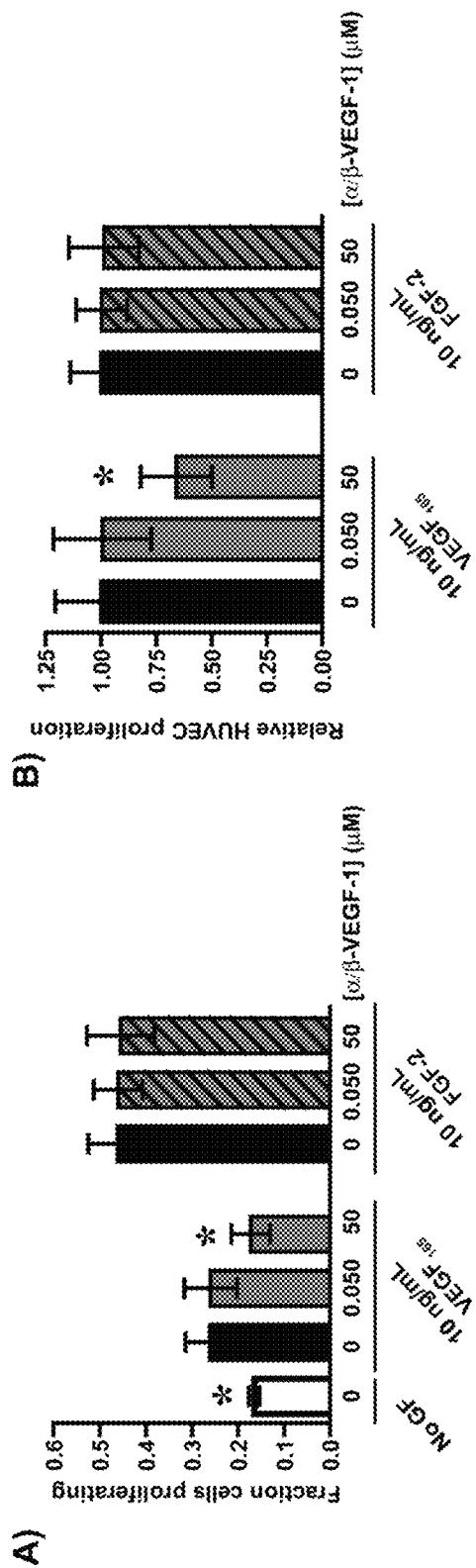
FIG. 16A. "Click-iT"®-brand EdU proliferation assay. *p<0.01 relative to 0 µM condition for appropriate growth factor, n=8, un-normalized values.
FIG. 16B. "Click-iT"®-brand EdU proliferation assay. *p<0.01 relative to 0 µM condition for appropriate growth factor, n=8. Relative proliferation normalized to the "0 µM" condition for each growth factor. ("Click-iT" is a registered trademark of Life Technologies Corporation, Carlsbad, Calif., USA.)
Figure 17:
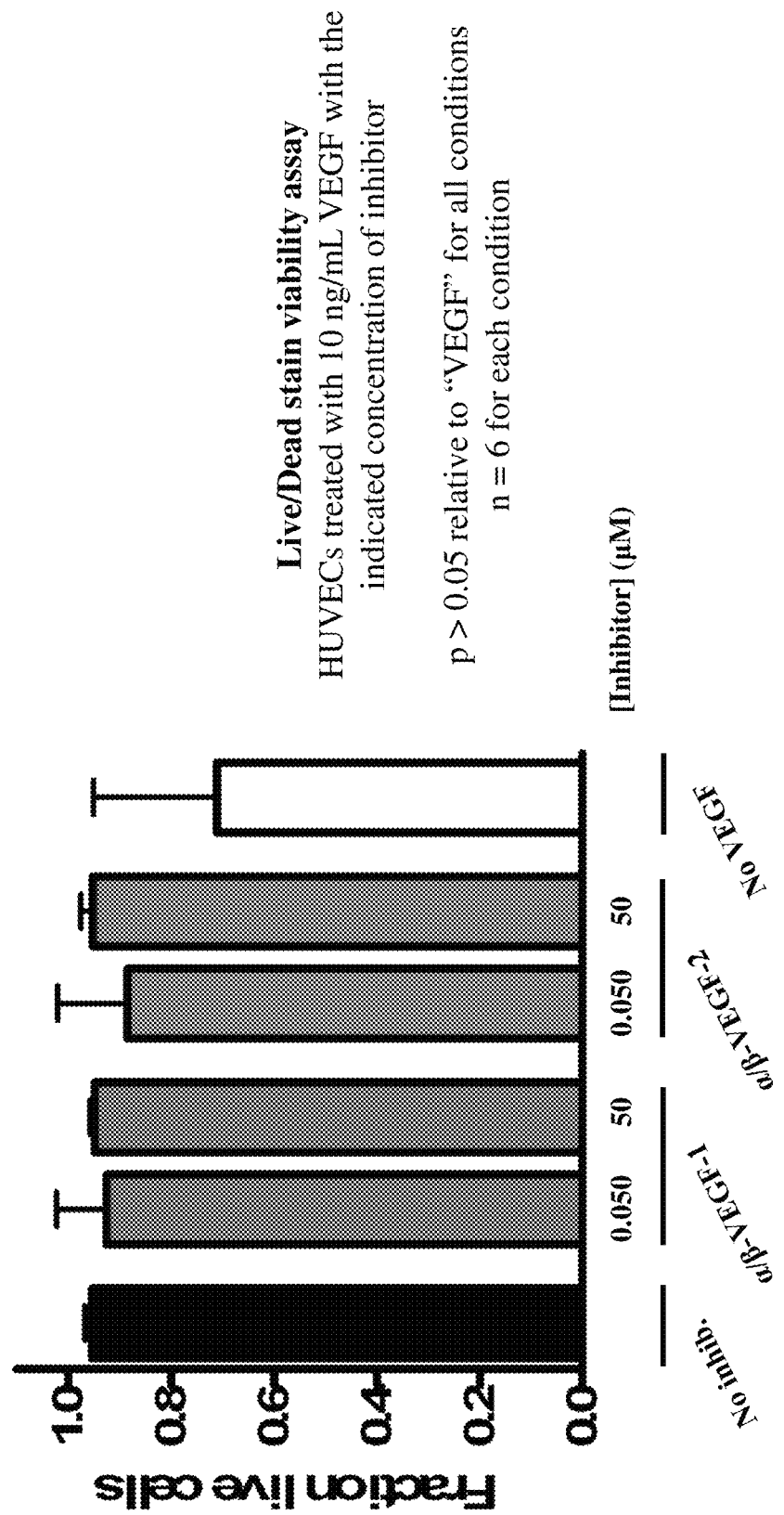
FIG. 17. LIVE/DEAD®-brand stain viability assay. p>0.05 relative "VEGF" for all conditions; n=6 for each condition. (LIVE/DEAD® is a registered trademark of Molecular Probes, Inc., Eugene, Oreg., USA.)

Both α/β-VEGF-1 and α/β-VEGF-2 do not cause a loss in HUVEC viability at 50 μM under the assay conditions, as evaluated by LIVE/DEAD cell viability assay, indicating that the inhibition of proliferation is not due to a non-specific cytotoxic effect (FIG. 17). As a further test of selectivity, α/β-VEGF-1 was evaluated for its ability to inhibit HUVEC proliferation induced by an unrelated growth factor, FGF-2. α/β-VEGF-1 at 50 μM was a potent inhibitor of proliferation induced by 10 ng/mL VEGF, but not by 10 ng/mL FGF-2, indicating that the antagonistic properties of α/β-VEGF-1 (and likely α/β-VEGF-2, though this compound was not tested in this experiment) are specific for VEGF. (FIGS. 16A and 16B.) Taken together, these data indicate that α/β-VEGF-1 and α/β-VEGF-2 are antagonists of VEGF in cell culture in a dose-dependent and specific manner, as designed.

α/β-Peptide Mimicry of the IgG-Binding Z-Domain:

Because peptides derived from the Z-domain are presumed to adopt very similar three-helix structures, it was hypothesized that strategies that proved successful for mimicry of Z-VEGF may also be applied to mimicry of other peptides derived from the Z-domain. To test this, attempts were made to mimic the first two helices of Z-IgG, the original Z-domain derived from domain B of staphylococcal protein A, using the same truncation and substitution pattern used in the development of α/β-VEGF-1, the tightest binding α/β-peptide for VEGF. The domain B:Fc fragment co-crystal structure (PDB: 1FC2) reveals that the three-helix scaffold binds the Fc portion of human IgG through the "protein binding face" of helices 1 and 2, and so it was reasoned that Z-IgG (which contains a Gly→Ala substitution relative to the native domain B) would be an ideal candidate for mimicry by the strategy described herein. Protein A is commonly used for the purification of IgGs and Fc-fusion proteins from various biological samples. Thus minimized, more stable versions of Z-IgG are also useful for these purposes.

Starting with Z-IgG, the same truncation of helix 3 and incorporation of α- and β-amino acid substitutions present in α/β-VEGF-1 was made to Z-IgG to give α/β-IgG-1 (FIG. 5). α/β-IgG-1 differs from α/β-VEGF-1 at 11 residues in helix 1 and helix 2, positions which correlate to the differences in Z-VEGF and Z-IgG and account for the differing protein binding specificity of these two peptides. Because Z-IgG contains one less residue than Z-VEGF (Ala14 in Z-VEGF), α/β-IgG-1 correspondingly has one less residue than α/β-VEGF-1. In the development of Z-VEGF, Ala12 was not a residue randomized to select for VEGF-binding and does not appear to make contact with VEGF in the Z-VEGF:VEGF co-crystal structure. As such, it was replaced with an APC residue during the design of α/β-VEGF-1 and α/β-VEGF-2. In contrast, the corresponding residue in fragment B (Asn11) appears to make contact with the Fc portion of human IgG in the co-crystal structure, and so α/β-IgG-2 was designed to maintain this native residue.

Figures 18A, 18B:
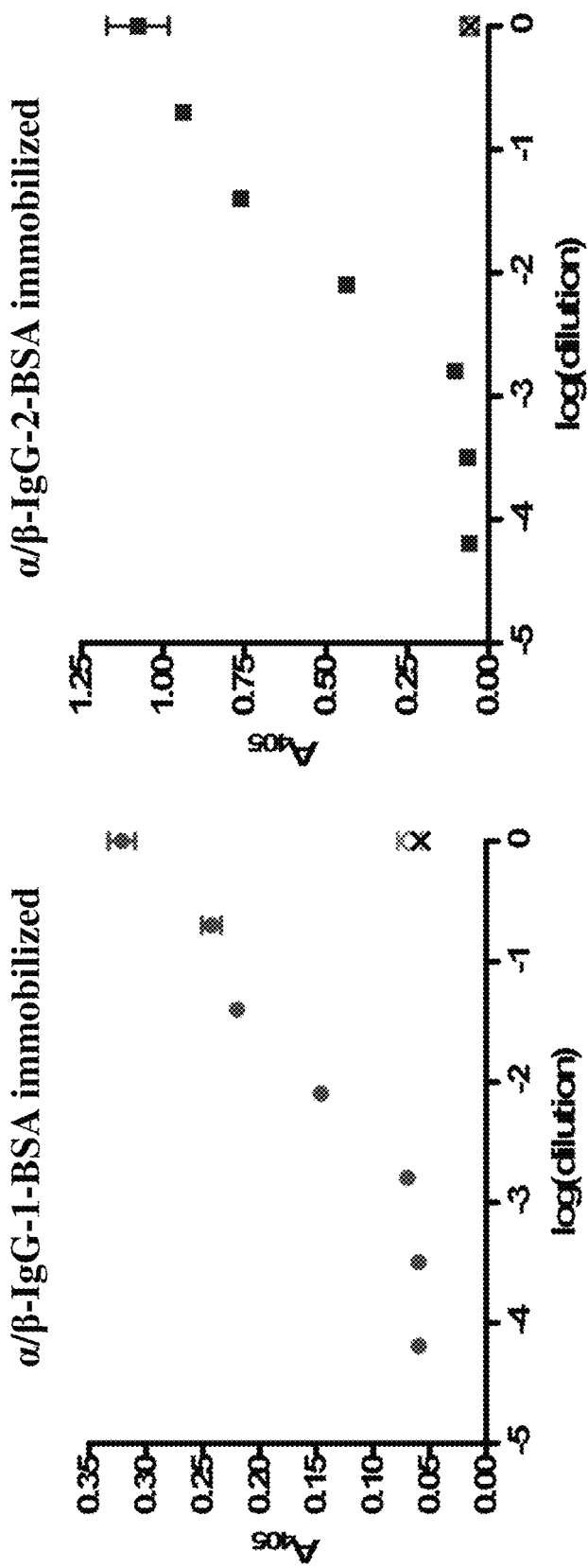
FIGS. 18A and 18B. Indirect ELISA detecting the binding of human IgG1-κ to immobilized peptide-BSA conjugates.

The ability of α/β-IgG-1 and α/β-IgG-2 to bind human IgG1-κ was evaluated by indirect ELISA. Both immobilized α/β-IgG-1 and α/β-IgG-2 bound human IgG1-κ, as detected using goat anti-human IgG-alkaline phosphatase (FIGS. 18A and 18B). A stronger signal was observed for immobilized α/β-IgG-2 than α/β-IgG-1 under these assay conditions. No ELISA signal was observed in the absence of α/β-peptide. Importantly, no increase in signal was observed in the absence of human IgG1-κ, indicating that the α/β-IgG-1 and α/β-IgG-2 are not binding the goat antibody used for detection (Z-IgG does not bind goat IgG with high affinity). Together these data indicate that α/β-IgG-1 and α/β-IgG-2 bind to human IgG1-κ, as designed.

Figure 19:
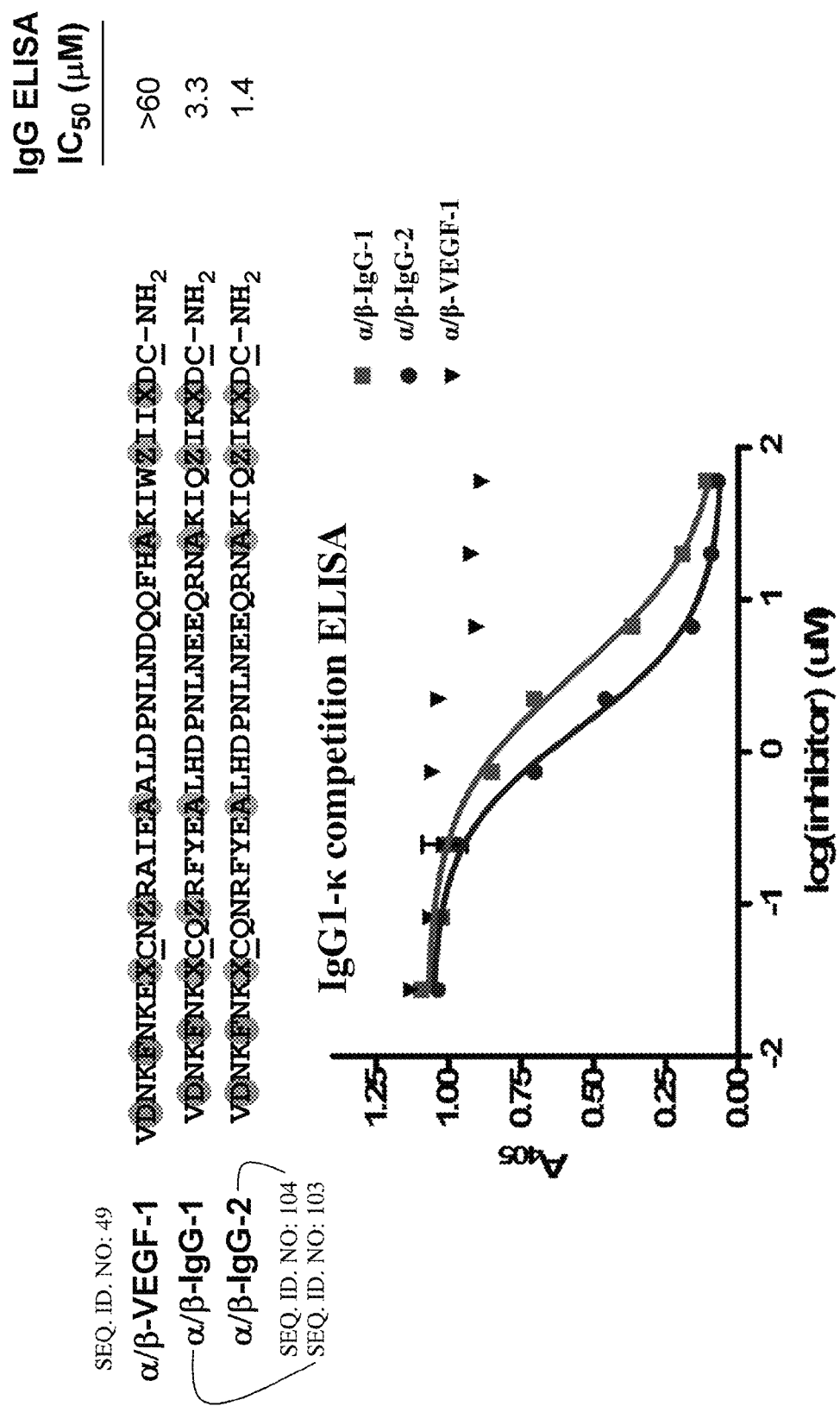
FIG. 19. A representative competition ELISA comparing different α/β-peptides based on Z-domain scaffold proteins. BSA conjugated with α/β-IgG-2 is immobilized onto the ELISA plate. 10 μg/mL of human IgG1-κ is pre-incubated with variable concentrations of α/β-IgG-1 (red), α/β-IgG-2 (blue), or α/β-VEGF-1 (black) and then allowed to bind to immobilized α/β-IgG-2 on the plate. After washing, wells are incubated with anti-human IgG (Fab-specific) AP conjugate from goat. Wells are washed again, followed by the addition of pNPP substrate. After 40 minutes, reactions were quenched with 1 M NaOH and the absorbance at 405 nm read. $IC_{50}$ is calculated using a sigmoidal dose-response model. Each condition was run in duplicate.
Figures 21A, 21B:
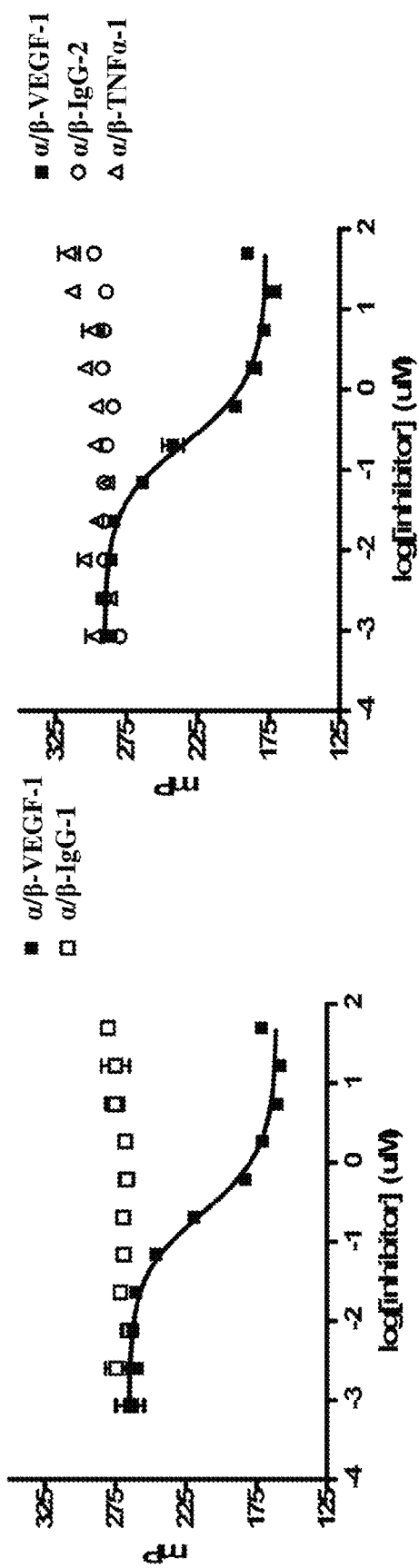
FIGS. 21A and 21B. Representative VEGF competition FP assays.

To more directly compare different α/β-peptides for IgG1 binding, the ability of α/β-peptides to bind human IgG1-κ was evaluated by competition ELISA (Table 2 and FIG. 19). Both soluble α/β-IgG-1 and α/β-IgG-2 are able to compete with immobilized α/β-IgG-2 for binding to human IgG1-κ, with $IC_{50}$ values in this assay of 3.3 μM and 1.4 μM, respectively. (Note that these $IC_{50}$ values are for this experimental ELISA set up only. They show that these α/β-peptides bind their target and can be used to compare efficacy within the same assay, but these values cannot be compared to previously published values using other assays, such as SPR.) α/β-VEGF-1, which has the same substitution pattern as α/β-IgG-1 and binds VEGF with high affinity, did not compete for binding to human IgG1-κ. In complementary experiments, α/β-IgG-1 and α/β-IgG-2 did not show binding to VEGF in the competition FP assay. See Table 4 below and FIGS. 21A and 21B.

TABLE 2

Binding of oligomers to human IgG1-κ:

| Oligomer | $IC_{50}$ (μM)[a] |
|---|---|
| α/β-IgG-1 | 3.3 |
| α/β-IgG-2 | 1.3 |
| α/β-VEGF-1 | >60 |

[a]$IC_{50}$ values represent the ability of α/β-peptides to compete with immobilized α/β-IgG-2 for binding to 10 μg/mL human IgG1-κ.

α/β-Peptide Mimicry of the TNF-α-Binding Z-Domain:

After successfully mimicking both Z-VEGF and Z-IgG, we sought to test the limits of our approach by extending our design to mimicry of a third Z-domain peptide of which there is not yet high resolution structural information on the peptide:protein interaction. Tumor necrosis factor-α (TNFα) is an inflammatory cytokine which has a variety of functions, including playing a key role in a number of inflammatory disorders. Agents that bind TNFα and inhibit binding to its receptors (TNFRs), which include monoclonal antibodies and soluble TNFR fragments, are currently used to treat inflammatory disorders such as rheumatoid arthritis and inflammatory bowel disease. Using phage display, Jonsson et al. previously developed Z-TNFα, a Z-domain peptide that binds to TNFα and is capable of blocking binding to TNFR in vitro. (Jonsson, A. et al. *Biotechnol. Appl. Biochem.* 2009, 54, 93)

TABLE 3

Inhibition of TNF-α/TNFR interaction:

| Oligomer | $K_i$ (μM)[a] |
|---|---|
| α/β-TNFα-1 | 0.024 |
| α/β-TNFα-2 | 0.0059 |
| α/β-VEGF-1 | >10 |
| α/β-IgG-1 | >10 |

[a]$IC_{50}$ values represent the ability of α/β-peptides to compete with immobilized TNFR1 for binding to 0.080 μg/mL TNFα.

TABLE 4

Binding of oligomers to VEGF:

| Oligomer | $K_i$ (μM)[a] |
|---|---|
| α/β-IgG-1 | >50 |
| α/β-IgG-2 | >50 |
| α/β-TNFα-1 | >50 |

[a]$K_i$ values for VEGF binding determined by competition FP assay.

Unlike Z-VEGF and Z-IgG, there is no high resolution structural information available illuminating the molecular-level interaction between Z-TNFα and TNFα. Despite this, it was reasoned that because TNFα binding was selected by altering only the residues on the "protein-binding" face of helices 1 and 2, the strategy that proved successful for mimicry of Z-VEGF and Z-IgG may be used to mimic Z-TNFα. α/β-TNFα-1 and α/β-TNFα-2 were thus designed by truncating helix 3 and incorporating the same substitutions as was successful for the VEGF- and IgG-binding α/β-peptides (FIG. 6).

The ability of α/β-TNFα-1 and α/β-TNFα-2 to bind to TNF-α and inhibit binding to TNFR was evaluated using competition ELISA (Table 3 and FIGS. 20A and 20B). Both α/β-TNFα-1 and α/β-TNFα-2, but not α/β-VEGF-1 or α/β-IgG-1 (which have the same substitution pattern as α/β-TNFα-1), were able to block binding of TNF-α to immobilized TNFR. Like α/β-IgG-1, α/β-TNFα-1 showed no binding to VEGF in the VEGF competition FP assay (Table 4), further highlighting the selectivity of these α/β-peptides for the proteins they were designed to target. Because these α/β-peptides contain β-amino acid/Aib content very similar to α/β-VEGF-1, these α/β-peptides should similarly have significantly decreased susceptibility to proteolytic degradation relative to the full-length Z-TNFα. As TNFα requires trimerization to bind TNFR, this example also highlights the versatility by which Z-domain scaffold α/β-peptide mimics can be used to inhibit a variety of different protein-protein interactions.

Conclusions:

Protein-based affinity scaffolds such as the Z-domain can be used as alternatives to antibodies as protein-targeting molecules. Their small size, relative stability, and presentation of a large, flat protein-binding surface that can be diversified while retaining the overall scaffold structure has led to a variety of Z-domain structures that selectively bind many different target proteins for a variety of different functions.

Described herein is the successful development of α/β-peptide mimics of the first two helices of Z-VEGF which antagonize VEGF with high binding affinity and display significantly decreased susceptibility to proteolytic degradation relative to Z-VEGF and α-VEGF-2. Furthermore, it has been shown that the same steps of truncation, cyclization through disulfide bond incorporation, and non-natural amino acid substitutions can be used to develop minimized α/β-peptide mimics of other Z-domain peptides (Z-IgG and Z-TNFα) relatively easily. These working examples show that the approach has general utility to all Z-scaffold peptides that can be generated for specific affinity interaction with a target. Despite high sequence homology, these different α/β-peptides show no evidence of cross-binding to proteins other than the one they were designed to target (e.g., α/β-VEGF-1 does not inhibit the TNFα/TNFR interaction and α/β-IgG-1 does not bind VEGF). The developed α/β-peptides differ from each other effectively only on the "protein-binding" face of helix 1 and 2 and, because altering these binding residues allows for rational selection for protein-binding specificity, it is presumed that these α/β-peptides present the protein-binding residues in the same orientation as the Z-domain peptides from which they were derived.

The α/β-peptide design strategy disclosed herein can be generalized to mimic other peptides based on the Z-domain scaffold. Because of their small size relative to the full-length Z-domains, the oligomers disclosed herein are more synthetically accessible and able to easily be modified compared to both full-length Z-domain peptides and antibodies. Because techniques such as phage display can generate Z-domain peptides to target many different proteins, the strategies described herein can be used to design α/β-peptides that target a variety of different protein-protein interactions without the need to synthesize and evaluate every possible α→β-amino acid residue substitution.

Screening for Biological Activity and Pharmaceutical Compositions:

The Z-scaffolds compounds having desired biological activities may be identified using appropriate screening assays. For example the following screening assays may be used to screen for particular biological activities indicative of corresponding pharmaceutical uses.

Anti-inflammatory and immunosuppressive activities of the subject compounds are determined by means of the following and similar assays: the IL-1β secretion inhibition, LPS fever, cytokine release from THP-1 cells, and functional IL-1 antagonist assays and the assay of carrageenan induced paw edema in the rat (as described in EP 0606044 and EP 0618223); the macrophilin binding, Mixed Lymphocyte Reaction (MLR), IL-6 mediated proliferation, localized graft-versus-host (GvH) reaction, kidney allograft reaction in the rat, experimentally induced allergic encephalomyelitis (EAE) in the rat, Freund's adjuvant arthritis, FKBP binding, steroid potentiation and Mip and Mip-like factor inhibition assays (as described in WO 94/09010, EP 0296123 and EP 0296122).

Central Nervous System (CNS) activity of the subject compounds is determined by means of the following and similar assays: serotonin ID (5HT 10) receptor agonist assays including the method of Weber et al. (Schmiedeberg's Arch. Pharmacol. 337, 595-601 (1988)) (and as described in EP 0641787)); 5HT3 receptor agonist assays (as described in GB 2240476 and EP 0189002); assays for activity in treatment of psychotic disorders and Parkinson's Disease, such as the apomorphine induced gnawing in the rat assay and dopamine receptor (D1 and D2) binding assays (as described in GB 20206115 B); assays for dopamine receptor antagonist activity (in relation to schizophrenia and related diseases, as described in EP 0483063 and EP 0544240); assays for activity in relation to senile dementia and Alzheimer's Disease (as described in EP 0534904); assays for activity in relation to cerebral ischaemia (as described in EP 0433239), and assays in relation to gastrointestinal motility such as the peristaltic reflex in isolated guinea pig ileum and assays of antiserotoninergic effects (specifically at the 5-HT4 receptors) (as described in EP 0505322).

Activity of the subject compounds in relation to bone and calcium metabolism is determined by assays as or similar to those described in WO 94/02510, GB 2218102B and WO 89/09786.

Activity of the compounds of formula I in relation to asthma and other allergic and inflammatory conditions is determined by the following assay procedures: the PDE isoenzyme inhibition, inhibition of eosinophil activation by formyl Met Leu Phe (f MLP), inhibition of TNFα secretion, inhibition of SRS-A production, bacterial endotoxin (LPS) induced lethality in the guinea pig, arachidonic acid induced irritant dermatitis in the mouse, relaxation of the human bronchus, suppression of SRS-A induced bronchoconstriction, suppression of bombesin induced bronchoconstriction, suppression of methacholine (MeCH) induced bronchoconstriction in the rhesus monkey and suppression of airways hyperactivity in the guinea pig assays (as described in European patent application No. 94810628.1 (EP 0664289), WO 94/12493 and GB 2213482).

Serine protease, e.g. Thrombin, inhibition activity of the subject compounds is determined using assays such as those described in WO 94/20526. Glycoprotein IIb/IIIa antagonist activity of the subject compounds is determined using the assay procedures described by Cook et al. (Thrombosis and Haemostasis, 70(3), 531-539 (1993) and Thrombosis and Haemostasis, 70(5), 838-847 (1993)) Müller et al. (J. Biol. Chem., Vol. 268, No. 9, 6800-6808 (1993)).

Anticancer activity of the subject compounds is determined by the anti-tumor activity assay as described in EP 0296122 or by trial procedures, for instance as described in GB 2239178. Multidrug resistance (MDR)-reversing activity is determined by the assays described in EP 0296122.

The relevant teachings of the patent documents and other publications referred to above is incorporated herein by reference. The subject compounds which have appropriate levels of activity in these assays are useful as pharmaceuticals in relation to the corresponding therapies or disease states.

Thus, included within the scope of the present disclosure are Z-scaffold polypeptide mimetics as described herein for use as pharmaceuticals and the use of these compounds for manufacturing a medicament to treat any disease associated with any of the assays previously described. Also disclosed herein is the use of the subject compounds as a pharmaceutical, as well as pharmaceutical compositions comprising an effective amount of a Z-scaffold polypeptide mimetic as described herein together with a pharmaceutically acceptable diluent or carrier.

Also disclosed herein are pharmaceutical compositions comprising one or more of the Z-scaffold mimetics disclosed herein or a pharmaceutically suitable salt thereof as described herein. More specifically, the pharmaceutical composition may comprise one or more of the subject compounds, as well as a standard, well-known, non-toxic pharmaceutically suitable carrier, adjuvant, or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, indictable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. In addition to such inert diluents, the composition may also include adjuvants, such as wetting agents, emulsifying and suspending agents, sweetening agents, flavoring agents, perfuming agents, and the like.

The pharmaceutical composition is preferably formulated by means generally known the industry. Thus, the pharmaceutical compositions disclosed herein comprise an effective amount of a Z-scaffold polypeptide mimetic or a pharmaceutically acceptable salt thereof together with a pharmaceutically acceptable carrier. Optionally, other therapeutically active substances or accessory agents may be included in addition to the α/β-polypeptide or the salt thereof. The pharmaceutical compositions comprise an amount of α/β-polypeptide or a pharmaceutically acceptable salt thereof that is effective to treat the maladies listed above in a mammal suffering therefrom (including humans). The carrier must be pharmaceutically acceptable in the sense of being compatible with the other ingredients in the particular composition and not deleterious to the recipient of the composition. The compositions include those suitable for oral, topical, rectal or parenteral (including subcutaneous, intramuscular, intradermal and intravenous) administration.

In a particular aspect, the pharmaceutical compositions comprise the active ingredient (a α/β-polypeptide Z-scaffold mimetic or a pharmaceutically acceptable salt thereof) presented in unit dosage form. The term "unit dosage" or "unit dose" designates a predetermined amount of the active ingredient sufficient to be effective to treat each of the indicated activities. Preferred unit dosage formulations are those containing a daily dose, daily sub-dose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form.

Compositions of the present invention suitable for oral administration may be presented as discrete unit dosages, e.g., as capsules, cachets, tablets, boluses, lozenges and the like, each containing a predetermined amount of the active ingredient; as a powder or granules; or in liquid form, e.g., as a collyrium, suspension, solution, syrup, elixir, emulsion, dispersion and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients or excipients, e.g., binders, lubricants, inert diluents, surface-active or dispersing agents. Molded tablets may be made by molding in a suitable machine a mixture of the powdered active compound with any suitable carrier.

Compositions suitable for parenteral administration conveniently comprise a sterile injectable preparation of the active ingredient in, for example, a solution which is preferably isotonic with the blood of the recipient. Useful formulations also comprise concentrated solutions or solids containing the active ingredient which upon dilution with an appropriate solvent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredient formulated into pharmaceutically-acceptable topical vehicles by conventional methodologies. Common formulations include drops, collyriums, aerosol sprays, lotions, gels, ointments, plasters, shampoos, transferosomes, liposomes and the like.

Compositions suitable for inhalation administration, for example, for treating bronchial infections, wherein the carrier is a solid, include a micronized powder or liquid formulation having a particle size in the range of from about 5 microns or less to about 500 microns, for rapid inhalation through the nasal or oral passage from a conventional inhalation squeeze or spray container. Suitable liquid nasal compositions include conventional nasal sprays, nasal drops and the like, of aqueous solutions of the active ingredient and optional adjuvants.

In addition to the aforementioned ingredients, the pharmaceutical compositions may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like.

The amount of active ingredient required to be effective for each of the indicated activities will, of course, vary with the individual mammal being treated and is ultimately at the discretion of the medical or veterinary practitioner. The factors to be considered include the species and sex of the mammal, the ailment being treated, the route of administration, the nature of the formulation, the mammal's body weight, surface area, age and general condition, and the particular compound to be administered. In general, the pharmaceutical compositions of this invention contain from about 0.5 to about 500 mg and, preferably, from about 5 to about 350 mg of the active ingredient, preferably in a unit dosage form, for each of the indicated activities. However, a suitable effective dose is in the range of about 0.1 to about 200 mg/kg body weight per day, preferably in the range of about 1 to about 100 mg/kg per day, calculated as the non-salt form of the α/β-polypeptide. The total daily dose may be given as a single dose, multiple doses, e.g., two to six times per day, or by intravenous infusion for a selected duration. Dosages above or below the range cited above are within the scope of the present disclosure and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of the active agent, twice per day. In topical formulations, the subject compounds are preferably utilized at concentrations of from about 0.1% to about 5.0% by weight.

the above-described pharmaceutical compositions may be utilized in connection with non-human animals, both domestic and non-domestic, as well as humans.

EXAMPLES

Materials

Protected α-amino acids and benzotriazole-1-yl-oxy-tris-pyrrolidino-phosphonium hexafluorophosphate (PyBOP) were purchased from Novabiochem (a part of EMD Biosciences, an affiliate of Merck, KGaA, Darmstadt, Germany) and Chem-Impex International (Wood Dale, Ill., USA). Protected $β^3$-amino acids were purchased from Chem-Impex International and PepTech Corporation (Bedford, Mass., USA). Fmoc-(1S,2S)-2-aminocycopentane carboxylic acid (ACPC) was purchased from Chem-Impex international (15073). Fmoc-APC(Boc) was synthesized as previously described (Lee, H. et al. *J. Org. Chem.* 2001, 66, 3597-3599). NovaPEG Rink Amide resin was purchased from Novabiochem (855047). All other solvents and reagents used for peptide synthesis were purchased from Sigma-Aldrich (St. Louis, Mo., USA) or Fisher Scientific (Waltham, Mass., USA).

Peptide Synthesis and Purification:

α-Peptides were either synthesized on solid phase using a Symphony-brand automated peptide synthesizer (Protein Technologies, Tucson, Ariz., USA) as previously reported (Lee, E. F. et al., *ChemBioChem*. 2011, 12, 2025-2032) or synthesized on NovaPEG Rink Amide resin using microwave-assisted solid-phase conditions, as described below. Z-VEGF was synthesized on a Symphony-brand peptide synthesizer, double coupling each amino acid, as previously described (Fedorova, A. et al, *Chem. Biol.* 2011, 18, 839-845). α/β-peptides were synthesized on NovaPEG Rink Amide resin using microwave-assisted solid-phase conditions based on Fmoc protection of the main chain amino groups, as previously reported. (Horne, S. W. et al., *Proc. Natl. Acad. Sci. USA* 2008, 105, 9151-9156) In brief, coupling reactions were carried out by treating the resin with a solution of protected amino acid, activated with PyBOP, and 1-hydroxybenzotriazole (HOBt) in the presence of N,N-diisopropylethylamine (DIEA) in 1-methyl-2-pyrrolidone (NMP). Deprotection of the Fmoc protecting group was carried out using a solution of 5% piperazine, 0.1 M HOBt in N,N-dimethylformamide (DMF). After the completion of the synthesis, α- and α/β-peptides containing no cysteine residues were cleaved from the resin using a solution of 95% trifluoroacetic acid (TFA), 2.5% $H_2O$, 2.5% triisopropylsilane (TIS). α- and α/β-peptides containing cysteine residues were cleaved from the resin using a solution of 94% TFA, 2.5% $H_2O$, 2.5% 1,2-ethanedithiol, and 1% TIS. Excess TFA was removed under a stream of nitrogen, and the crude peptides were precipitated by the addition of cold diethyl ether. For α- and α/β-peptides without a disulfide bond, solutions of crude peptide were purified using preparative scale reverse-phase HPLC on C18 columns. For α- and α/β-peptides containing a disulfide bond, crude ether-precipitated peptides were dissolved in DMSO (10 mL for 50 μmol synthesis) and ammonium hydroxide ($NH_4OH$) was added to make the solution basic (approximately 25 drops for 50 μmol synthesis). These DMSO solutions were exposed to air and the peptides allowed to oxidize over the course of 4-7 days. Progress of oxidation could be monitored by HPLC. Peptides were then purified by reverse-phase HPLC. Final peptide purity was assessed by analytical HPLC and identity confirmed by MALDI-TOF-MS.

Protein Expression and Purification:

$VEGF_{165}$ expression and purification was performed as previously described (Peterson, K. J. et al., *Anal. Biochem.* 2008, 378, 8-14).

VEGF Fluorescence Polarization Assays:

Inhibitors of the VEGF/VEGFR interaction were evaluated using VEGF direct binding and competition fluorescence polarization (FP) assays, as previously described (Peterson, K. J. et al., *Anal. Biochem.* 2008, 378, 8-14), but using a modified tracer. The tracer used in the assays reported here was the Met→norleucine variant of the previously reported tracer (peptide BODIPY-v114*$_{ANT}$, sequence ((BODIPY$^{TMR}$)-X-CDIHV(Nle)WEWECFERL-$NH_2$ (SEQ. ID. NO: 101), X=[2-(2-amino-ethoxy)-ethoxy]acetic acid, (Nle)=norleucine, where cysteines are linked in intramolecular disulfide; $K_D$=21 nM.) To account for slight variations in amount of active protein resulting from each expression, the $K_d$ for BODIPY-v114$_{ANT}$ was re-measured for each VEGF stock by direct binding FP assay, and the resulting $K_d$ value was used for the determination of inhibitor dissociation constant ($K_i$) values derived from competition FP assays using that stock. DMSO stock solutions of α- and α/β-peptide inhibitors were prepared and concentration determined by UV absorbance at 280 nm. Extinction coefficients for α- and α/β-peptides were calculated based on the number of tryptophans ($\epsilon_{280}$=5690 $M^{-1}$ $cm^{-1}$), tyrosines ($\epsilon_{280}$=1280 $M^{-1}$ $cm^{-1}$), and cystines ($\epsilon_{280}$=120 $M^{-1}$ $cm^{-1}$) in each primary sequence (Gill, S. C, et al. *Anal. Biochem.* 1989, 182, 319-326). Competition FP assays were performed by adding 2 μL of serial dilutions of inhibitor in DMSO to 48 μL of solution containing BODIPY-v114$_{ANT}$ (final concentration=10 nM) and VEGF (final concentration=40 nM) in FP buffer (50 mM NaCl, 16.2 mM $Na_2HPO_4$, 3.8 mM $KH_2PO_4$, 0.15 mM $NaN_3$, 0.15 mM EDTA, 0.5 mg/mL Pluoronic-F68, pH 7.5) in 384-well, black polystyrene plates (Costar, purchased from Fisher Scientific). Plates were incubated at room temperature for 5-7 hours, and read on a BioTek Synergy 2 microplate reader (BioTek US, Winooski, Vt., USA). Each condition was run in duplicate in each assay. Inhibition constants ($K_i$) were determined from FP data using methods described for a competitive binding model with GraphPad Prism 4.0 (Peterson, K. J. et al., *Anal. Biochem.* 2008, 378, 8-14). Reported $K_i$ values are representative values from multiple replicate assays.

Circular Dichroism Spectroscopy:

Circular dichroism measurements were performed on an Aviv Model 420 Circular Dichroism Spectrometer (Aviv Biomedical, Inc., Lakewood, N.J., USA). Solutions of α- and α/β-peptides (75 μM) were prepared in PBS, pH 7.5. Spectra were collected at 20° C. in a 0.1 cm quartz cell with a wavelength step size of 1 nm and a 10 second averaging time. Spectra were normalized to units of $[\theta] \times 10^{-3}$ (deg $cm^2$ $dmol^{-1}$ $res^{-1}$) using the exact concentration determined by UV absorbance (see above) to account for slight variations in concentration between solutions.

Proteinase K Susceptibility Assay:

Stock solutions of 50 μg/mL proteinase K (Novagen, 70663-4) were prepared in Tris-buffered saline (TBS), pH 7.5. Stock solutions of 90 μM α-peptide or α/β-peptide in TBS were prepared, as determined by UV absorbance. For each proteolysis reaction, the peptide stock was diluted with TBS to achieve a final peptide concentration of 45 μM. Proteinase K stock was added (final concentration=10 μg/mL) and the reaction was allowed to proceed at room temperature. At each time point, 50 μL of the reaction mixture was removed and quenched by the addition of 100 μL of 1:1 $H_2O$/acetonitrile with 1% TFA. 125 μL of the resulting quenched solution was injected onto analytical reverse-phase HPLC and the relative amount of peptide remaining was quantified by integration of the peak at 220 nm in a series of HPLC chromatograms. Each reaction was run at least in duplicate. Half-lives were determined by fitting the time course of peptide degradation to an exponential decay model using GraphPad Prism 4.0.

HUVEC Proliferation Assay:

Human umbilical vein endothelial cells (HUVECs) (Lonza, Basel, Switzerland, catalog no. CC2519) were cultured using Medium 199 (M199) (Mediatech, Herndon, Va., USA; 50-050-PB) supplemented with penicillin/steptomycin (HyClone-brand, Thermo Fisher Scientific, Herndon, Va., USA; SV30010) and EGM-2 (Lonza, CC4176) at 37° C. in 5% $CO_2$. Cells were grown to 60-80% confluence and then serum-starved in M199 with 2% cosmic calf serum (CCS) (HyClone-brand, SH30087) overnight. Cells were then trypsinized and reseeded in gelatin-coated 96-well plates at a density of 3000-4000 cells/well in M199 with 2% CCS and allowed to attach for 6-8 hours. Filter sterilized stock solutions of α- or α/β-peptide in PBS were made at a concentration of 200 μM, as determined by UV absorbance. Appropriate dilutions of α- or α/β-peptide were made with PBS, and the resulting solutions were premixed with recombinant human $VEGF_{165}$ (R&D Systems, 293-VE-010) or recombinant human FGF basic (FGF-2) (R&D Systems, a wholly owned subsidiary of TECHNE Corporation, Minneapolis, Minn., USA; 233-FB-025) in M199/2% CCS and incubated at room temperature for 1 hour. For controls with no inhibitor, the same amount of PBS was pre-incubated with growth factor. After pre-incubation, these solutions were then added to the cells to give a final concentration of 10 ng/mL growth factor (except in "no growth factor" controls), between 0 µM and 50 µM peptide, and 25% PBS. Cells were then cultured in the presence/absence of inhibitors and/or VEGF for 36 hours. Relative cell proliferation was quantified using the "Click-iT"-brand EdU Alexa Flour 488 Assay (Life Technologies, C10337). After 24 hours of exposure to assay conditions, EdU was added (final concentration=10 µM), and then the cells were maintained under normal culture conditions for an additional 12 hours (36 hours total) before being fixed with formalin. EdU incorporation was detected using Life Technologies' assay protocol. All cell nuclei were stained with the Hoechst 33342 stain supplied with the Click-iT EdU assay kit (1:1000 dilution in PBS). Plates were imaged using a Nikon Eclipse TI inverted microscope with filters for FITC (detecting Alexa Fluor 488, EdU labeled cells) and DAPI (detecting Hoescht 33342, labeling all cells). Images were analyzed using NIS-Elements AR Imaging Software (Nikon Instruments, Inc., Melville, N.Y., USA) to count the number of proliferating cells (EdU stained) and total number of cells (Hoechst stained). For analysis, data were scaled relative to control conditions in which no inhibitor was present (10 ng/mL VEGF in M199 with 2% CSS, 25% PBS, but with no inhibitor present).

LIVE/DEAD Viability Assay:

HUVECs were cultured and treated with inhibitors and VEGF, as described above. After 36 hours in culture under the experimental conditions, cells were stained using a LIVE/DEAD®-brand Viability/Cytotoxicity kit (Life Technologies, L3224). 4 µM calcein-AM and 2 µM ethidium homodimer-1 in M199 without serum was used to stain live and dead cells, respectively. After 30 minutes incubation with staining reagents, the media was removed from wells and replaced with fresh media for imaging. Plates were imaged using a Nikon Eclipse TI inverted microscope under 10× objective and filters for FITC (detecting calcien-AM, live cells) and TexasRed (detecting ethidium homodimer-1, dead cells). Images were analyzed using NIS-Elements AR Imaging Software to count the number of live and dead cells. The fraction of live cells was determined by dividing the number of live cells by the total number of cells (live cells+dead cells). Data were analyzed using a two-tailed t-test to determine statistical significance.

Human IgG1-κ ELISA:

The binding of α/β-peptides to human IgG1-κ was determined by indirect and competition ELISA. α/β-IgG-1 and α/β-IgG-2 were each conjugated to BSA by dissolving approximately 1 mg of purified α/β-peptide in a solution containing 3% BSA, 8 mM glutaraldehyde in 0.1 M NaOAc, pH 7.0, at a total volume of 330 µL. The conjugation reaction was allowed to proceed on a rocker at room temperature for 2 hours and quenched by the addition of 5-6 mg glycine and additional incubation for 1 hour. After quenching, the reaction solution was diluted to 3 mL with PBS, pH 7.0 and dialyzed overnight into PBS at 4° C. After dialysis, the α/β-peptide-BSA conjugates were concentrated to approximately 500 µL using 10,000 MWCO Amcon Ultra-15 centrifugal filter units (EMD Millipore, UCF901024). These concentrated solutions were stored at −20° C., diluted and used directly for indirect and competition ELISA experiments.

For indirect ELISA, 50 µL of serial dilutions (starting with 1:50 dilution in PBS, pH 7.4) of α/β-IgG-1 or α/β-IgG-2 conjugated to BSA were immobilized onto a Nunc clear polystyrene 96-well ELISA plate (Thermo Scientific, 430341) in PBS, incubated overnight at 4° C. After immobilization, the plate was washed with PBS/0.05% TWEEN 20 (for this and all subsequent washes, wells were rinsed 3-5 times with 200 µL PBS/0.05% TWEEN) and blocked with 200 µL of 1% BSA in PBS/0.05% TWEEN for 1-2 hours at room temperature. The plate was then washed with PBS/0.05% TWEEN and 100 µL of human IgG1-κ (Sigma, 15154) was added and incubated at room temperature for about 1.5 hours. Because a stronger signal was observed for the α/β-IgG-2-BSA conjugate relative to the α/β-IgG-1-BSA conjugate (possibly due to a difference in conjugation efficiency or binding affinity), 30 µg/mL human IgG1-κ in PBS/0.05% TWEEN was used for assays in which α/β-IgG-1 was immobilized and 10 µg/mL human IgG1-κ in PBS/0.05% TWEEN was used for assays in which α/β-IgG-2 was immobilized. After allowing the Fc portion of human IgG1-κ to bind to immobilized α/β-peptide, the plate was washed with PBS/0.05% TWEEN and the binding of human IgG1-κ detected by adding 100 µL of 1:2000 dilution of goat Anti-Human IgG (Fab specific)-Alkaline Phosphatase antibody (Sigma A8542) and incubating at room temperature for 1 hour. After washing with PBS/0.05% TWEEN, 50 µL of SIGMAFAST p-Nitrophenyl phosphate solution (Sigma, N1891) was added to each well and the alkaline phosphatase reaction allowed to proceed at room temperature. Plates were read during the time course of the reaction on a BioTek Synergy 2 microplate reader, reading $A_{405}$. Each condition was run in duplicate. As a control, no signal was observed in wells in which no α/β-peptide was immobilized, indicating that human IgG1-κ is not binding non-specifically to immobilized BSA. In addition, no signal was observed for either α/β-peptide when no human IgG1-κ was incubated, indicating that the Anti-Human IgG (Fab specific)-Alkaline Phosphatase antibody does not bind non-specifically to the α/β-peptides or BSA.

For competition ELISA, 50 µL of a 1:100 dilution of the α/β-IgG-2-BSA conjugate in PBS was immobilized onto the ELISA plate and incubated at 4° C. overnight. After immobilization, the plate was washed with PBS/0.05% TWEEN, blocked with 1% BSA for 1-2 hours, and then washed with PBS/0.05% TWEEN. Serial dilutions of soluble α/β-peptides in DMSO were prepared (final concentrations=3 nM-50 µM), and 10 µL of each of these solutions added to 240 µL of human IgG1-κ (final concentration=10 µg/mL) in PBS/0.05% TWEEN. The soluble α/β-peptides were allowed to pre-incubate with human IgG1-κ for 1 hour, and then 100 µL of each α/β-peptide/IgG1-κ mixture was added to the ELISA plate and incubated at room temperature for 1.5 hours. The binding of human IgG1-κ to the immobilized α/β-IgG-2 was measured using goat Anti-Human IgG (Fab specific)-Alkaline Phosphatase antibody, as described above. Each condition was run in duplicate. Plates were read during the time course of the reaction on a BioTek Synergy 2 microplate reader, reading $A_{405}$. To compare the ability of each soluble α/β-peptide to bind human IgG1-κ and inhibit binding to the immobilized α/β-IgG-2, $IC_{50}$ values were calculated by fitting the ELISA absorbance data to a sigmoidal dose-response equation. As controls, no signal was observed in the absence of human IgG1-κ, in the absence of immobilized α/β-IgG-2, or the absence of both human IgG1-κ and immobilized α/β-IgG-2.

TNFα/TNFR Competition ELISA:

The binding of α/β-peptides to TNFα to inhibit binding to TNFR was determined by competition ELISA. For each competition ELISA experiment, 50 µL of 1 µg/mL recombinant human sTNF RI/TNFRSF1A (R&D Systems, 636-R1-025) in PBS was added to each well and incubated at 4° C. overnight to immobilize TNFR onto the ELISA plate. After immobilization, the plate was washed with PBS/0.05%

TWEEN, blocked with 1% BSA in PBS for 2 hours, and then washed with PBS/0.05% TWEEN. Serial dilutions of soluble α/β-peptides in DMSO were prepared (final concentrations=0.04 nM-10 μM), and 10 μL of each of these solutions added to 240 μL of recombinant human TNFα (R&D Systems, 210-TA-020, final concentration=0.080 μg/mL) in PBS/0.05% TWEEN. The α/β-peptides were allowed to preincubate with TNFα for 3 hours and then 50 μL of each α/β-peptide/TNFα mixture was added to wells on the ELISA plate and incubated at room temperature for 1 hour. The plate was then washed with PBS/0.05% TWEEN and the presence of TNFα detected by adding 100 μL of a 1:500 dilution of Human TNFα Biotinylated Affinity Purified PAb (R&D Systems, BAF210) and incubating at room temperature for 1 hour. The plate was washed with PBS/0.05% TWEEN and 100 μL of 1:1000 dilution of Streptavidin-Alkaline Phosphatase (R&D Systems, AR001) in PBS/0.05% TWEEN was added and allowed to incubate at room temperature for 30 minutes. After washing with PBS/0.05% TWEEN, 50 μL of SIGMAFAST p-Nitrophenyl phosphate solution (Sigma, N1891) was added to each well and the alkaline phosphatase reaction allowed to proceed at room temperature. Plates were read during the time course of the reaction on a BioTek Synergy 2 microplate reader, reading $A_{405}$. Each condition was run in duplicate. To compare the ability of each soluble α/β-peptide to inhibit the binding of TNFα to immobilized TNFR, $IC_{50}$ values were calculated by fitting the ELISA absorbance data to a sigmoidal dose-response equation.

Illustrative Z-Domain Scaffold Peptide Mimics:

All peptides and α/β-peptides were synthesized and purified using previously reported methods. $K_i$ values are derived from VEGF competition FP assays displacing the Met10 to Nle variant of the v114-based tracer BODIPY-v114$_{ANT}$ developed in Peterson, K. J. et al. *Anal. Biochem.* 2008, 378, 8-14. FP assays were only run once to test binding affinity. For "lead compound" oligomers (such as α/β-VEGF-1), competition FP assays have been run multiple times and reported value is representative of the value obtained.

In all of the following tables, NB=no binding, indicates that oligomer showed $K_i$>50 μM in VEGF competition FP assay. Some α/β-peptides contain the sAPC (U) residue, a cyclic β-amino acid residue developed for use as a cyclic residue that bears a negative charge APC and ACPC (the latter is commercially available, see also Gellman et al., U.S. Pat. Nos. 6,683,154, 6,958,384, and 7,858,737, incorporated herein by reference) may also be used in place of sAPC. (See tables below for structures.) The removal of the negative charge at positions replaced by β-amino acid residues was not detrimental to binding affinity for VEGF.

1. Early Experiments:

See Table 5 for the first peptide mimics fabricated. E1-E4 are early attempts to truncate Z-VEGF and rigidify it with different disulfide bond placements, ACPC substitutions, etc. These modifications were rational designs based on the crystal structures. Mini-Z-1 1-3 are analogs of Mini-Z-1 (from Fedorova, A. et al. *Chem. Biol.* 2011, 18, 839-845) that are designed to bind VEGF as a monomer (Mini-Z-1 is a two-helix VEGF-binding peptide that binds VEGF as a dimer due to phage display developing an unintended binding mode) Mini-Z-1 H2 1-8 are analogs of helix 2 of Mini-Z-1 that were rigidified using salt bridging or Aib residues.

TABLE 5

Early Mimics.

| ID | Sequence | Ki (μM) |
|---|---|---|
| E1 | KE(Nle)HNRYAIEAALDPNLNDQQFHAKIWSIIDDPS (SEQ. ID. NO: 1) | NB |
| E2 | KE(Nle)HNRYAIEAAL<u>C</u>PNLNDQQFHA<u>C</u>IWSIIDDPS (SEQ. ID. NO: 2) | NB |
| E3 | <u>C</u>NKE<u>X</u>HNAYAIEIALLPNLNDQQFHAXIWXLIDDP<u>C</u>Q (SEQ. ID. NO: 3) | NB |
| E4 | KEXHNAXAIEIALLPNLNDQQFHAXIWXLIDDPS (SEQ. ID. NO: 4) | NB |
| Mini-Z-1 1 | FNKEALLRYKEAALDPNLNLYQRIAKIVSIDDDA (SEQ. ID. NO: 5) | NB |
| Mini-Z-1 2 | FNKEALLRYKEAALDPNLGGGGGNLYQRIAKIVSIDDDA (SEQ. ID. NO: 6) | NB |
| Mini-Z-1 3 | FNKEALLRYKEAALDPNLGGGGGGNLYQRIAKIVSIDDDA (SEQ. ID. NO: 7) | NB |
| Mini-Z-1 H2 1 | Ac-RRLYEEIRRIVEEDRRA (SEQ. ID. NO: 8) | NB |
| Mini-Z-1 H2 2 | Ac-ARLYEAIARIVEADARA (SEQ. ID. NO: 9) | NB |
| Mini-Z-1 H2 3 | Ac-EELYRRIEEIVRRDEEA (SEQ. ID. NO: 10) | NB |
| Mini-Z-1 H2 4 | Ac-AELYRAIAEIVRADAEA (SEQ. ID. NO: 11) | NB |
| Mini-Z-1 H2 5 | Ac-LELYRRIAEIVRIDDEA (SEQ. ID. NO: 12) | NB |

TABLE 5-continued

Early Mimics.

| ID | Sequence | Ki (µM) |
|---|---|---|
| Mini-Z-1 H2 6 (SEQ. ID. NO: 13) | Ac-LRLYERIARIVEIDDRA | NB |
| Mini-Z-1 H2 7 (SEQ. ID. NO: 14) | Ac-LNLY<u>A</u>RIAKIVSIDD<u>A</u>A | NB |
| Mini-Z-1 H2 8 (SEQ. ID. NO: 15) | Ac-LNLY<u>A</u>RIA<u>A</u>IV<u>A</u>IDD<u>A</u>A | NB |

<u>C</u> = underlined Cys residues form disulfide.
Aib = <u>A</u>; ACPC = <u>X</u>

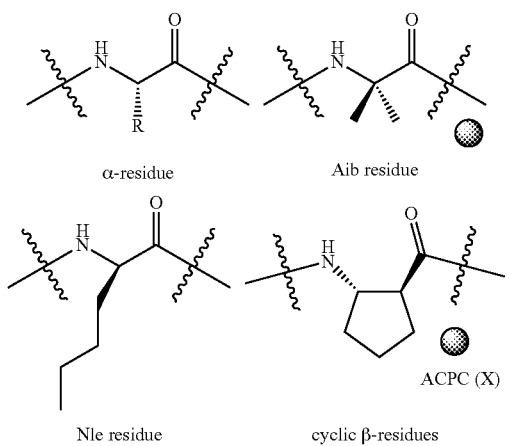

α-residue    Aib residue

Nle residue    cyclic β-residues

2. Truncated Z-VEGF:

Table 6 shows a series of variations in which Z-VEGF was truncated and then modified with various beta-amino acid substitutions. Z-VEGF binds with $K_i$=0.52 µM by VEGF competition fluorescence polarization (FP) assay.

Fluorescently-labeled Z-VEGF (Flu-Z-VEGF) binds to VEGF in direct binding FP assay at 0.088 µM. (Reported Z-VEGF SPR direct binding value=0.038 µM from Fedorova, A. et al. *Chem. Biol.* 2011, 18, 839-845.)

Z-VEGF (7-40), which corresponds to residues of helix 1 and helix 2 in the Z-VEGF crystal structure (PDB: 3S1K) showed no binding.

The analogs which rigidified the two-helix structure and incorporated a disulfide link on residues 7-40 (S1-S5) increased binding affinity.

Z-VEGF shows high binding affinity for VEGF, but Z-VEGF(7-56) does not. Thus, it appears residues 1-6, play a role in strong binding to VEGF despite being absent from the crystal structure.

TABLE 6

Truncated Z-VEGF.

| ID | Sequence | Ki (µM) |
|---|---|---|
| Z-VEGF | VDNKFNKEMHNAYAIEIALLPNLNDQQFH AFIWSLIDDPSQSANLLAEAKKLNDAQAPK (SEQ. ID. NO: 16) | 0.41 |
| Flu-Z-VEGF | FAM-VDNKFNKEMHNAYAIEIALLPNLNDQ QFHAFIWSLIDDPSQSANLLAEAKKLNDAQAPK (SEQ. ID. NO: 17) | Direct binding Kd = 0.088 |
| Z-VEGF (7-40) | KEMHNAYAIEIALLPNLNDQQFHAFIWSLIDDPS (SEQ. ID. NO: 18) | NB |
| S1 | KE(Nle)<u>C</u>NARAIEAALDPNLNDQQFHAKIWSIIDD<u>C</u>G (SEQ. ID. NO: 19) | 9.5 |
| S2 | KEQ<u>C</u>NARAIEAALDPNLNDQQFHAKIWSIIDD<u>C</u>G (SEQ. ID. NO: 20) | 1.9 |
| S3 | KEQ<u>C</u>NARAIEAALDPNLNDQQFHAKIWAIIDD<u>C</u>G (SEQ. ID. NO: 21) | 2.2 |
| S4 | KEQ<u>C</u>NAAAIEAALDPNLNDQQFHAKIWAIIDD<u>C</u>G (SEQ. ID. NO: 22) | 4.3 |
| S5 | KEQ<u>C</u>NAZAIEAALDPNLNDQQFHXKIWXIIDD<u>C</u>G (SEQ. ID. NO: 23) | NB |

TABLE 6-continued

Truncated Z-VEGF.

| ID | Sequence | Ki (µM) |
|---|---|---|
| Z-VEGF (7-56) | KEMHNAYAIEIALLPNLNDQQFHAFIW SLIDDPSQSANLLAEAKKLNDAQ (SEQ. ID. NO: 24) | 6.3 |

FAM = 6-carboxyfluorescein
C = underlined Cys residues form disulfide
Aib = A; ACPC = X; APC = Z

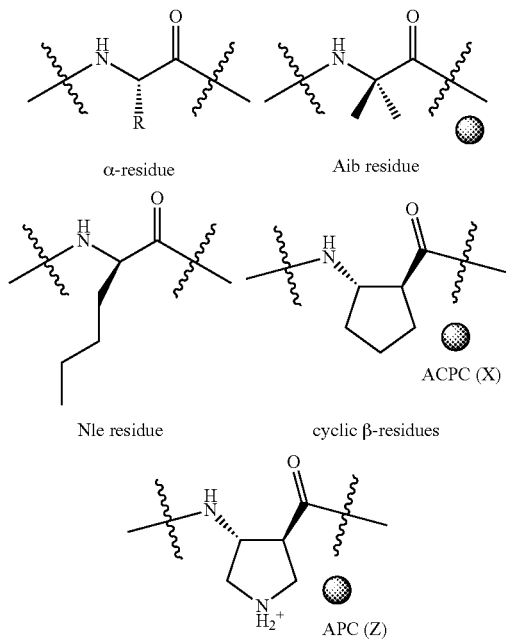

α-residue
Aib residue
Nle residue
cyclic β-residues
ACPC (X)
APC (Z)

3. Residues 1-6 and Disulfide Constraint Impact Binding Affinity:

Table 7 depicts a series of modification positions 1-6, as well as compound having an inserted disulfide bond. Z-VEGF (1-38) (corresponding to Z-VEGF without helix 3; SEQ. ID. NO: 25), includes residues 1-6 but shows no binding.

Incorporating a disulfide bond at the appropriate position (determined by a crystal structure alignment of Z-VEGF with a two-helix analog of Z-IgG) regains binding affinity (S6). This peptide showed low solubility and was difficult to handle, likely do to presence of many hydrophobic groups on the back face of helix 1 and helix 2.

Incorporating five of the α-amino acid substitutions (identified by phage display to develop a two-helix Z-IgG analog and also used to develop a two-helix Z-HER2 analog) into helix 1 and helix 2 gives α-VEGF-1. This peptide does not show binding to VEGF, but shows increased solubility. Incorporation of a disulfide bond gives α-VEGF-2, which shows binding affinity to VEGF indistinguishable from full-length Z-VEGF.

S7 is identical to α-VEGF-2, but includes a C-terminal glycine residue. The C-terminus glycine residue provides a short spacer between the terminus and the cysteine present in the disulfide bond. Many of the early peptide sequences contain this residue, but its presence/absence has no effect on binding affinity to VEGF; α-VEGF-2 and S7 bind VEGF with indistinguishable binding affinity.

TABLE 7

Modifications at Positions 1-6 and Introducing Disulfide Links.

| ID | Sequence | Ki (µM) |
|---|---|---|
| Z-VEGF (1-38) | VDNKFNKEMHNAYAIEIALLPNLNDQQFHAFIWSLIDD (SEQ. ID. NO: 25) | NB |
| S6 | VDNKFNKEQCNAYAIEIALLPNLNDQQFHAFIWSLIDDCG (SEQ. ID. NO: 26) | 0.92 |
| α-VEGF-1 | VDNKFNKEQHNARAIEAALDPNLNDQQFHAKIWSIIDD (SEQ. ID. NO: 27) | NB |
| α-VEGF-2 | VDNKFNKEQCNARAIEAALDPNLNDQQFHAKIWSIIDDC (SEQ. ID. NO: 28) | 0.42 |
| S7 | VDNKFNKEQCNARAIEAALDPNLNDQQFHAKIWSIIDDCG (SEQ. ID. NO: 29) | 0.27 |

C = underlined Cys residues form disulfide

4. Initial Attempts to Incorporate α-Residues into Truncated Z-VEGF:

Table 8 presents a series of truncated Z-VEGF analogs in which select alpha-amino acid residues have been replaced with beta-amino acid residues. S8-S12 are compounds that incorporate β-amino acid residues into helix 2 of α-VEGF-2/S7. The positions for β-amino acid incorporation were chosen based on rational inspection of the Z-VEGF:VEGF co-crystal structure and replacing residues that did not appear to make contacts with VEGF or interhelical contacts.

S8 replaces a subset of residues with $\beta^3$-residues in an αβαααβ pattern, as has been successful in many past attempts to mimic α-helical structures. This peptide showed no binding. S8 thus shows that the effects of the beta-amino acid substitutions on binding are not predictable. S9 replaces two residues with cyclic β-amino acid residues. This showed reduced binding affinity. S10-S11 show individual α→β replacements. S10 shows that Ala30 is not tolerant to cyclic β-amino acid residue replacement. S11 and S12 show that two other positions are moderately tolerant to cyclic β-amino acid residue replacement.

TABLE 8

β-Residues into Truncated Z-VEGF.

| ID | Sequence | Ki (μM) |
|---|---|---|
| S8 | VDNKFNKEQCNARAIEAALDPNLNDQQFHAKIWSIIDDCG (SEQ. ID. NO: 30) | NB |
| S9 | VDNKFNKEQCNARAIEAALDPNLNDQQFHXKIWXIIDDCG (SEQ. ID. NO: 31) | 42 |
| S10 | VDNKFNKEQCNARAIEAALDPNLNDQQFHXKIWSIIDDCG (SEQ. ID. NO: 32) | 20 |
| S11 | VDNKFNKEQCNARAIEAALDPNLNDQQFHAKIWXIIDDCG (SEQ. ID. NO: 33) | 1.3 |
| S12 | VDNKFNKEQCNARAIEAALDPNLNDQQFHAKIWSIIDUCG (SEQ. ID. NO: 34) | 2.3 |

C = underlined Cys residues form disulfide
Aib = A; ACPC = X; APC = Z; sAPC = U:
$\beta^3$ residues K, S, and D in S8 are bold underlined.

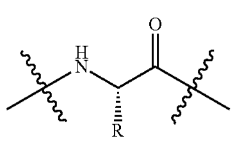

α-residue 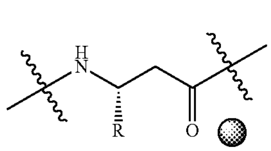 $\beta^3$-residue

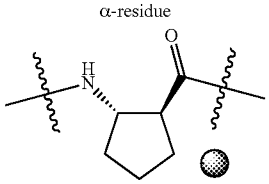

ACPC (X)

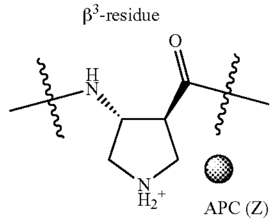

APC (Z)

cyclic β-residues

-continued 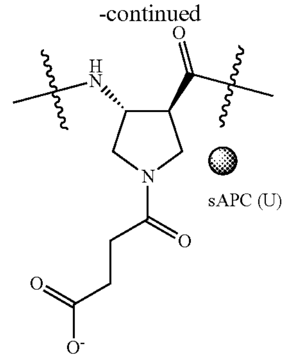 sAPC (U)

5. Incorporation of Non-Natural Helix-Promoting Residues Through Iterative Design in Helix 2:

Because Ala30 was intolerant to cyclic β-amino acid residue replacement, it was hypothesized that residues close to the loop region may be more tolerant to Aib residue replacement. (Aib can promote helical conformation, but does not introduce an extra methylene unit, so it is potentially less perturbing of the overall structure in certain cases.)

Referring now to Table 9, S13 shows that several Aib residues can be incorporated near the loop region. S14 shows that even in the presence of the stabilizing Aib residues, Ala30 replacement with a cyclic β-amino acid residue is not tolerated. S15 shows that cyclic β-amino acid residue replacement can be used together with Aib replacement to yield an α/β-peptide with high binding affinity. S16 and S17 test replacement of one additional cyclic β-amino acid residue. S17 indicates the position more favored for replacement, though both are tolerated.

TABLE 9

Incorporation of Non-Natural Helix-Promoting Residues.

| ID | Sequence | Ki (μM) |
|---|---|---|
| S13 | VDNKFNKEQCNARAIEAALDPNLNDQQFHAKIWAIIDDCG (SEQ. ID. NO: 35) | 0.22 |
| S14 | VDNKFNKEQCNARAIEAALDPNLNDQQFHXKIWAIIDDCG (SEQ. ID. NO: 36) | 26.8 |
| S15 | VDNKFNKEQCNARAIEAALDPNLNDQQFHAKIWXIIDDCG (SEQ. ID. NO: 37) | 0.19 |
| S16 | VDNKFNKEQCNARAIEAALDPNLNDQQFHAKIWXIIDUCG (SEQ. ID. NO: 38) | 0.51 |
| S17 | VDNKFNKEQCNARAIEAALDPNLNDQQFHAKIWXIIUDCG (SEQ. ID. NO: 39) | 0.065 |

C = underlined Cys residues form disulfide
Aib = A; ACPC = X; APC = Z; sAPC = U

6. Extending Non-Natural Residue Incorporation into Helix 1:

Table 10 presents a series of analogs which extend the unnatural beta-amino acid substitutions into helix 1. Referring to Table 10, S18 and S19 extended Aib replacements into helix 1. These positions were chosen rationally based on structure/parallels to what we discovered to be successful in helix 2. S20 and S21 replace each of these individually with cyclic β-amino acid residues.

Both positions near the N-terminus of helix 1 were revealed to be tolerant to cyclic β-amino acid residue replacement. Thus, S22 combines both of these substitutions with the substitutions shown to be successful for helix 2 to yield an α/β-peptide with high affinity for VEGF.

TABLE 10

| ID  | Sequence | Ki (μM) |
|---|---|---|
| S18 | VDNKFNKEQCNARAIEAALDPNLNDQQFHAKIWXIIDDCG (SEQ. ID. NO: 40) | 0.35 |
| S19 | VDNKFNKEACNARAIEAALDPNLNDQQFHAKIWXIIDDCG (SEQ. ID. NO: 41) | 0.71 |
| S20 | VDNKFNKEQCNXRAIEAALDPNLNDQQFHAKIWXIIDDCG (SEQ. ID. NO: 42) | 0.29 |
| S21 | VDNKFNKEXCNARAIEAALDPNLNDQQFHAKIWXIIDDCG (SEQ. ID. NO: 43) | 0.26 |
| S22 | VDNKFNKEXCNXRAIEAALDPNLNDQQFHAKIWXIIUDCG (SEQ. ID. NO: 44) | 0.071 |

C = underlined Cys residues form disulfide
Aib = A; ACPC = X; APC = Z; sAPC = U

7. Truncating at N-Terminus:

Table 11 presents a series of compounds in which the N-terminus of the native VEGF Z-domain was truncated. Referring to the table, S23 keeps the same pattern of non-natural residues as S22, but now replaces the sAPC residues with ACPC residues. S24 and S25 attempt to truncate the N-terminus of the α/β-peptide which is now rigidified by both a disulfide bond and several helix-promoting residues. Removal of residues 1-3 (S24) is tolerated, but removal of residues 1-6 (S25) is not. This is consistent with early experiments showing that residues 1-6 are important for binding in the full length Z-VEGF (see above).

TABLE 11

N-Terminus Truncations.

| ID | Sequence | Ki (μM) |
|---|---|---|
| S23 | VDNKFNKEXCNXRAIEAALDPNLNDQQFHAKIWXIIXDCG (SEQ. ID. NO: 45) | 0.104 |
| S24 | KFNKEXCNXRAIEAALDPNLNDQQFHAKIWXIIXDCG (SEQ. ID. NO: 46) | 0.204 |
| S25 | KEXCNXRAIEAALDPNLNDQQFHAKIWXIIXDCG (SEQ. ID. NO: 47) | 4 |

C = underlined Cys residues form disulfide
Aib = A; ACPC = X; APC = Z; sAPC = U

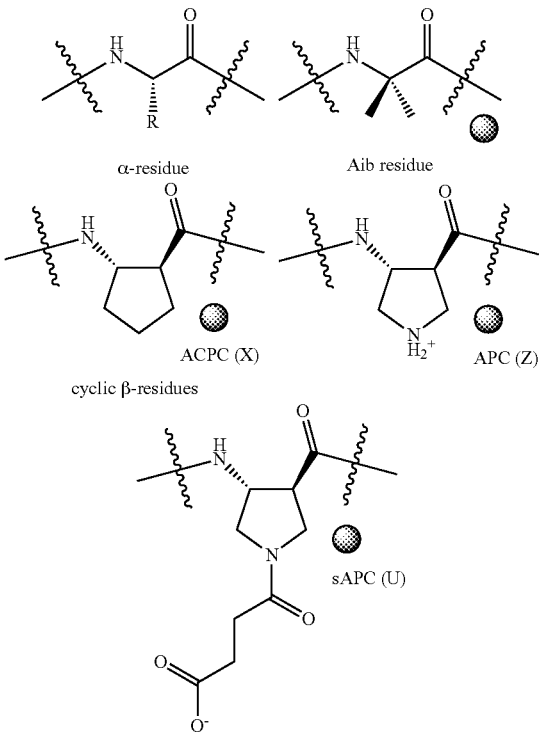

α-residue    Aib residue cyclic β-residues    ACPC (X)    APC (Z)

sAPC (U)

8. Development of Optimized Designs:

Table 12 depicts a series of variations that incorporate some of the modifications discussed above, as well as additional changes.

Referring to Table 12, S26 removes the C-terminal glycine and also switches the identity of the cyclic β-amino acid residues to increase solubility. APC (Z) is charged, and so this helps to promote aqueous solubility. α/β-VEGF-1 incorporates two $β^3$-residues into the N-terminus to increase this region's resistance to proteolysis without removing any of the side-chains. α/β-VEGF-1-linear has no disulfide bond. Its lack of binding to VEGF indicates that the helix-promoting residues are not sufficient to promote the correct VEGF-binding conformation alone. S27 shows that residues 1-3 are not required (similar to S24) for VEGF binding. S28 is an analog of S26 with one additional Aib residue in helix 2 to increase proteolytic resistance. α/β-VEGF-2 incorporates two $β^3$-residues into the N-terminal region of S28. S29 shows that residues 1-3 are not required (similar to S24 and S27) for VEGF binding.

TABLE 12

Optimized Designs.

| ID | Sequence | Ki (μM) |
|---|---|---|
| S26 | VDNKFNKEXCNZRAIEAALDPNLNDQQFHAKIWZIIXDC (SEQ. ID. NO: 48) | 0.10 |
| α/β-VEGF-1 | VDNKFNKEXCNZRAIEAALDPNLNDQQFHAKIWZIIXDC (SEQ. ID. NO: 49) | 0.11 |
| α/β-VEGF-1-linear | VDNKFNKEXHNZRAIEAALDPNLNDQQFHAKIWZIIXD (SEQ. ID. NO: 50) | NB |
| S27 | KFNKEXCNZRAIEAALDPNLNDQQFHAKIWZIIXDC (SEQ. ID. NO: 51) | 0.15 |

TABLE 12-continued

Optimized Designs.

| ID | Sequence | Ki (μM) |
|---|---|---|
| S28 | VDNKFNKEXCNZRAIEAALDPNLNDAQFHAKIWZIIXDC (SEQ. ID. NO: 52) | 0.34 |
| α/β-VEGF-2 | VDNKFNKEXCNZRAIEAALDPNLNDAQFHAKIWZIIXDC (SEQ. ID. NO: 53) | 0.38 |
| S29 | KFNKEXCNZRAIEAALDPNLNDAQFHAKIWZIIXDC (SEQ. ID. NO: 54) | 0.45 |

9. Salt Bridging (Ion Pairing) Interactions can be Used to Varying Effectiveness to Stabilize Two-Helix Structure and Identify Positions Tolerant to Charge Substitutions:

Table 13 presents a series of analogs in which residues were inserted that were thought to stabilize a two-helix structure via intra-molecular salt bridging. S30-35 are α-peptides that explore the possibility of enhancing helicity of two-helix analogs of Z-VEGF using salt-bridging/ion pairing interactions (e.g., Glu/Arg pairs near each other in the int TABLE 14-continued Z-TNF-α Mimics.

| ID | Sequence | TNFa-TNFR ELISA IC$_{50}$ (nM) | S-S Bond? |
|---|---|---|---|
| α/β-TNFα-1 | VDNKFNKXCGZRIGEAGTDPNLNHQQFRAKILZIWXDC-NH2 (SEQ. ID. NO: 63) | 30 | Yes |
| α/β-TNFα-2 | VDNKFNKXCGWRIGEAGTDPNLNHQQFRAKILZIWXDC-NH2 (SEQ. ID. NO: 64) | 6.6 | Yes |
| α/β-TNFα-2ND | VDNKFNKXLGWRIGEAGTDPNLNHQQFRAKILZIWXDP-NH2 (SEQ. ID. NO: 65) | 32 | No |
| α/β-TNFα-4 | VDNKFNKXCGWRIGEAGTDPNLNHQQFRAKILZIWXDC-NH2 (SEQ. ID. NO: 66) | 24 | Yes |
| α/β-TNFα-5 | NKXCGZRIGEAGTDPNLNHQQFRAKILZIWXDC-NH2 (SEQ. ID. NO: 67) | 35 | Yes |
| α/β-TNFα-6 | VDNKFNKXLGZRIGEAGTDPNLNHQQFRAKILZIWXDP-NH2 (SEQ. ID. NO: 68) | 1900 | No |
| α/β-TNFα-7 | NKXLGWRIGEAGTDPNLNHQQFRAKILZIWXDP-NH2 (SEQ. ID. NO: 69) | 52 | No |
| α/β-TNFα-8 | VDNKFNKXLGWAIGELGTDPNLNHQQFRAKALZLWXDP-NH2 (SEQ. ID. NO: 70) | 114 | No |
| α/β-TNFα-9 | VDNKFNKXCGWAIGELGTDPNLNHQQFRAKALZLWXDC-NH2 (SEQ. ID. NO: 71) | 26 | Yes |
| α/β-TNFα-10 | CGWRIGEAGTDPNLNHQQFRAKILZIWXDC-NH2 (SEQ. ID. NO: 72) | 7.6 | Yes |
| α/β-TNFα-11 | LGWRIGEAGTDPNLNHQQFRAKILZIWXDP-NH2 (SEQ. ID. NO: 73) | 1000 | No |
| α/β-TNFα-12 | WRIGEAGTDPNLNHQQFRAKILZIWXDP-NH2 (SEQ. ID. NO: 74) | >10,000 | No |
| α/β-TNFα-13 | WRIGEAGTDPNLNHQQFRAKILZIWXDP-NH2 (SEQ. ID. NO: 75) | | |
| α/β-TNFα-14 | LGWRIGEAGTDPNLNHQQFRAKILZIWX-NH2 (SEQ. ID. NO: 76) | 1000 | No |
| α/β-TNFα-15 | XWRIGEAGTDPNLNHQQFRAKILZIWX-NH2 (SEQ. ID. NO: 77) | >10,000 | No |
| α/β-TNFα-16 | XLGWRIGEAGTDPNLNHQQFRAKILZIWX-NH2 (SEQ. ID. NO: 78) | 510 | No |
| α/β-TNFα-17 | XLGWCIGEAGTDPNLNHQQFRAKILZCWX-NH2 (SEQ. ID. NO: 79) | 6.2 | Yes |
| α/β-TNFα-18 | XLGWRIGECGTDPNLNHQQFRACILZIWX-NH2 (SEQ. ID. NO: 80) | 154 | Yes |
| sTNFR1 | soluble TNF-receptor 1 extracellular domain fragment | 6.9 | |

A = Aib
D, F = beta3 analogue of corresponding alpha residue
X = ACPC
Z = APC

10. Z-HER2 Mimics:

Likewise, using the protocols detailed herein, a series of α/β peptide mimetics of the Z-domain of HER2 were constructed. Binding of the mimics to soluble TNFα to block binding to immobilized receptor was then tested. The results are shown in Tables 15 and 16. The native Z-HER2 is 58 amino acids long and includes three distinct alpha-helical domains. Helix 1 spans residues 8-18. Helix 2 spans residues 25-36. Helix 3 spans residues 41-54. As shown in Table 16, in the various mutations, the Z-HER2 was truncated, a disulfide bridge between cysteine residues or homo-cysteine residues were introduced, and various beta-amino acid residues were inserted into the derivatives. The results these modifications had on the binding of the various derivatives is presented in Table 16.

TABLE 15

Z-HER2 Mimics - Sequences.

| | | |
|---|---|---|
| ZHER2: 343 | VDNKFNKEMRNAYWEIALLPNLNNQQKRAFIRSLYDDPSQSANLLAEAKKLNDAQAPK (SEQ. ID. NO: 81) | |
| 1 (truncated) | VENKFNKEMRNAYWEIALLPNLNNQQKRAFIRSLYDDPG (SEQ. ID. NO: 82) | |
| 2 (5-39C) | VENKCNKEMRNAYWEIALLPNLNNQQKRAFIRSLYDDPC (SEQ. ID. NO: 83) | |
| 3 (5-39C2) | VENKCNKEMRNAYWEIALLPNLNNQQKRAFIRSLYDDPC (SEQ. ID. NO: 84) | |
| 4 (helicity) | FNKEMRNRYWEAALDPNLNNQQKRAKIRSIYDDPS (SEQ. ID. NO: 85) | |
| 5 (α-5-39, 5-39C) | CNKEMRNRYWEAALDPNLNNQQKRAKIRSIYDDC (SEQ. ID. NO: 86) | |
| 6 (α-5-39, 5-39C2) | C2NKEMRNRYWEAALDPNLNNQQKRAKIRSIYDDC2 (SEQ. ID. NO: 87) | |
| 7 (α/β-1-38, 9-38C) | VDNKFNKXCRZRYWEAALDPNLNNQQKRAKIRZIYXDC (SEQ. ID. NO: 88) | |
| 8 (α/β 6-38, 9-38C) | NKXCRZRYWEAALDPNLNNQQKRAKIRZIYXDC (SEQ. ID. NO: 89) | |
| 9 (α/β 9-38, 9-38C) | CRZRYWEAALDPNLNNQQKRAKIRZIYXDC (SEQ. ID. NO: 90) | |
| 10 (α-5-38, 9-38C) | NKECRNRYWEAALDPNLNNQQKRAKIRSIYDDC (SEQ. ID. NO: 91) | |
| 11 (α/β 5-39, 5-39C) | CNKXMRZRYWEAALDPNLNNQQKRAKIRZIYXDPC (SEQ. ID. NO: 92) | |
| 12 (α/β 5-39, 5-39C, X36D) | CNKXMRZRYWEAALDPNLNNQQKRAKIRZIYDDPC (SEQ. ID. NO: 93) | |
| 13 (α/β 5-39) | FNKXMRZRYWEAALDPNLNNQQKRAKIRZIYXDPS (SEQ. ID. NO: 94) | |
| 14 (α/β 5-39) | FNKXMRZRYWEAALDPNLNNQQKRAKIRZIYDDPS (SEQ. ID. NO: 95) | |
| 15 (α/β E15Aib) | FNKXMRZRYWAAALDPNLNNQQKRAKIRZIYDDPS (SEQ. ID. NO: 96) | |
| 16 (α/β Q25Aib) | FNKXMRZRYWEAALDPNLNNAQKRAKIRZIYDDPS (SEQ. ID. NO: 97) | |
| 17 (α/β D37X) | FNKXMRZRYWEAALDPNLNNQQKRAKIRZIYDXPS (SEQ. ID. NO: 98) | |
| 18 (c α/β 8-39C) | FNKCMRZRYWEAALDPNLNNQQKRAKIRZIYDDPC (SEQ. ID. NO: 99) | |
| 19 (c α/β 8-39C2) | FNKC2MRZRYWEAALDPNLNNQQKRAKIRZIYDDPC2 (SEQ. ID. NO: 100) | |

C = Cysteine engaged in disulfide
C2 = Homocysteine engaged in disulfide
A = Aib
X = ACPC
Z = APC

TABLE 16

Z-HER2 Mimics - Binding.

| SEQ. ID. NO: | reported Kd (nM) | ELISA 1 Ki (nM) calcd. | ELISA 2 Ki (nM) | ELISA 3 Ki (nM) calcd. | half-life $t_{1/2}$ (min) |
|---|---|---|---|---|---|
| 81 | 0.022 | 0.0008 | 0.051 | 0.06 | |
| 82 | no blinding | | | | |
| 83 | 259 | | | | |
| 84 | 78 | | | | |
| 85 | 44 | | 15 | | |
| 86 | 15 | 0.6 | 1.6 | 1.2 | 0.13 |
| 87 | 5 | 1.8 | | | |
| 88 | | 66 | | | |
| 89 | | 42 | 43 | | |
| 90 | | 350 | | | |

TABLE 16-continued

Z-HER2 Mimics - Binding.

| SEQ. ID. NO: | reported Kd (nM) | ELISA 1 Ki (nM) calcd. | ELISA 2 Ki (nM) | ELISA 3 Ki (nM) calcd. | half-life $t_{1/2}$ (min) |
|---|---|---|---|---|---|
| 91 | | | 7.5 | | |
| 92 | | | 20 | | |
| 93 | | | 4.0 | 2.9 | 41 |
| 94 | | | 111 | | |
| 95 | | | | 20 | 70 |
| 96 | | | | 28 | |
| 97 | | | | 33 | 260 |
| 98 | | | | 8300 | |
| 99 | | | | 16 | |
| 100 | | | | 9.7 | |

REFERENCES

Protein-Protein Interactions:
Wells, J. et al. *Nature* 2007, 450, 1001.
Foldamers:
Haase, H. et al. *J. Am. Chem. Soc.* 2012, 134, 7652 (v114 mimicry).
Horne, W. *Proc. Natl. Acad. Sci. U.S.A.* 2009, 106, 14751 (gp41 mimicry).
Horne, W. *Angew. Chem., Int. Ed.* 2008, 47, 2853 (Puma BH3 mimicry).
Horne, W. *Exp. Opin. Drug Discov.* 2011, 6, 1247 (review: peptide and peptoid foldamers in medicinal chemistry).
Johnson, L. et al. *Method Enzymol.* 2013, 523, 407 (review on α-helix mimicry with α/β-peptides).
Mandal, K. et al. *Proc. Natl. Acad. Sci. U.S.A.* 2012, 37, 14779 (mirror image phage display of VEGF).
Karle, I. et al. *Biochemistry* 1990, 29, 6747 (Aib structures review).
Steer, D. et al. *Curr. Med. Chem.* 2002, 9, 811 (β-amino acids as peptidomimietics review).
Yamaguchi, H. et al. *Biosci. Biotechnol. Biochem.* 2003, 67, 2269 (Aib increases resistance to proteases example).
v114 and v107:
Fairbrother, W. et al. *Biochemistry* 1998, 37, 17754 (v107 and v114 phage display).
Pan, B. et al. *J. Mol. Biol.* 2002, 316, 769 (v107 NMR structure).
Non-IgG scaffolds Reviews:
Binz, H. et al. *Nat. Biotech.* 2005, 23, 1257 (review of novel binding proteins from non-IgG scaffolds).
Gilbreth, R. et al. *Curr. Opin. Struc. Biol.* 2012, 22, 413 (review of structures for binding proteins based on scaffolds).
Gerbauer, M. et al. *Curr. Opin. Chem. Biol.* 2009, 13, 245 (Review on uses and different scaffolds).
Grönwall, C. et al. *J. Biotechnol.* 2009, 140, 254 (Review of binding proteins with emphasis on affibody).
Nygren, P. *J. Immunol. Methods* 2004, 290, 3 (binding proteins from alternative scaffolds).
Nygren, P. *FEBS J.* 2008, 275, 2668 (Affibody protein review).
Skerra, A. *Curr. Opin. Biotech.* 2007, 18, 295 (Review).
Skerra, A. *J. Mol. Recognit.* 2000, 13, 167 (Review).
Nilsson, F. et al *Curr. Opin. Drug Disc.* 2007, 10, 167 (affibody review).
Lofblom, J. et al. *FEBS Lett.* 2010, 584, 2670 (affibody-specific review).
Tolmachev, W. et al. *Minerva Biotecnol.* 2009, 21, 21 (Update on Affibodies for in vivo imaging).

Protein A/Z Domain (Study of Domain B and Development of Z):
Langone, J. et al. *Adv. Immunol.* 1982, 32, 157 (Protein A review).
Langone, J. et al. *J. Immunol. Methods* 1982, 55, 277 (applications of immobilized Protein A review).
Deisenhofer, J. *Biochemistry* 1981, 20, 2361 (structure of domain B and Fc).
Nilsson, B. et al. *Protein Eng.* 1987, 1, 107 (development of Z domain).
Gouda, H. et al. *Biochemistry* 1992, 31, 9665 (low resolution domain B NMR structure).
Jendeberg, L. et al. *Biochemistry* 1996, 35, 22 (low resolution NMR structure of Z domain, helix 3 does not unwind when binding).
Tashiro, M. et al. *J. Mol. Biol.* 1997, 272, 573 (high resolution NMR structure of Z domain).
Z-Scaffold Molecules:
Nord L. et al. *Protein Eng.* 1995, 8, 601 (shows phage display on Z-domain to form combinatorial library).
Nord, K. et al. *Nat. Biotech.* 1997, 15, 772 (uses phage for the first time to develop affibody to a new protein, Taq).
Nord, K. et al. *Eur. J. Biochem.* 2001, 268, 4269 (develop human factor VIII-specific affibody).
Eklan, M. et al. *Proteins Struc. Funct. Genet.* 2002, 48, 454 (develop Z-SPA1).
Wahlberg, E. et al. *Proc. Natl. Acad. Sci. U.S.A.* 2003, 100, 3185 (solution structure of Z-SPA1:Z-IgG complex).
Hoghom, M. et al. *Proc. Natl. Acad. Sci. U.S.A.* 2003, 100, 3191.
Wahlberg, E. et al. *J. Am. Chem. Soc.* 2006, 128, 7651 (stabilize Z-SPA1 using disulfide to increase binding).
Engfeldt, T. et al. *Chembiochem* 2005, 6, 1043 (Use of triple-labeled affibody for protein binding assay).
Lendel, C. et al. *J. Mol. Biol.* 2006, 359, 1293 (structure of Z-Taq with anti-Z-Taq affibody).
Friedman, M. et al. *Protein Eng.* 2007, 20, 189 (development of Z-EGFR affibody by phage display).
Friedman, M. et al. *J. Mol. Biol.* 2008, 376, 1388 (Z-EGFR affinity maturation to develop Z-EGFR$_{1907}$).
Hoyer, W. et al. *Proc. Natl. Acad. Sci. U.S.A.* 2008, 105, 5099 (Affibody targeting A13 peptide. Binds in unexpected way).
Ahlgren, S. et al. *J. Nucl. Med.* 2010, 51, 1131 (Imaging of HER2 using re-engineered scaffold to increase stability).
Wallberg, H. et al. *Prot. Express. Purif.* 2011, 76, 127 (Affinity chromatography with affibody).
Lindborg, M. et al. *J. Mol. Biol.* 2011, 407, 298 (PDGFRβ-targeted affibody blocks receptor in vivo).
Z-HER2:
Wikman, M. et al. *Protein Eng. Des. Sel.* 2004, 17, 455 (Original Z-HER2 phage development by phage display).
Orlova, A. et al. *Cancer Res.* 2006, 66, 4339 (affinity maturation of Z-HER2, imaging).
Orlova, A. et al. *Cancer Res.* 2007, 67, 2178 (Z-HER2 peptide made from peptide synthesis, imaging, emphasizes site specific modifications made possible by synthetic approaches, well defined and homogenous).
Eigenbrot, G. et al. *Proc. Natl. Acad. Sci. U.S.A.* 2010, 107, 15039 (crystal structure of Z-HER2).
Orlova, A. et al. *J. Nucl. Med.* 2009, 50, 417 (Z-HER2 comparison to antibody for imaging).
Baum, R. et al. *J. Nucl. Med.* 2010, 51, 892 (first clinical evaluation of affibody for imaging, Z-HER2).
Tolmachev, V. et al. *Cancer Res.* 2007, 67, 2273 (Targeted radionuclide therapy with Z-HER2+ABD to increase half life).

Z-VEGF:
Fedorova, A. et al. *Chem. Biol.* 2011, 18, 839 (development of Z-VEGF).

Z-TNFα:
Jonsson, A. et al. *Biotechnol. Appl. Biochem.* 2009, 54, 93 (development of Z-TNFα).
LöFdahl, P. et al. *Biotechnol. Appl. Biochem.* 2010, 55, 111 (affinity maturation of affibody proteins to TNFα).
Kronqvist, N. et al. *Protein Eng. Des. Sel.* 2008, 21, 247 (TNFα affibodies using staphylococcal display).

Two-Helix Z-Domain Analogs:
Braisted, A. et al. *Proc. Natl. Acad. Sci. U.S.A.* 1996, 93, 5688 (two helix Z-IgG development).
Starovasnik, M. et al. *Proc. Natl. Acad. Sci. U.S.A.* 1997, 94, 10080 (two helix Z-IgG disulfide incorporation and NMR structure).
Webster, J. et al. *ChemBioChem* 2009, 10, 1293 (two helix Z-HER2 development).
Ren, G. et al. *Amino Acids* 2012, 43, 405 (imaging with two-helix Z-HER2).
Jarver, P. et al. *J. Pept. Sci.* 2011, 17, 463 (Backbone cyclized two-helix Z-IgG).
Honarvar, H. et al. *Nucl. Med. Biol.* 2013, 40, 378 (Evaluation of backbone cyclized two-helix HER2 for imaging).

VEGF:
Ferrara, N. et al. *Nature* 2005, 438, 967 (review: angiogenesis as a target).
Ferrara, N. et al. *Nat. Med.* 2003, 9, 669 (review: the biology of VEGF and its receptors).
Ferrara, N. et al. *Nat. Rev. Drug Disc.* 2004, 3, 391 (Bevacizamab review).
Muller, Y. et al. *Proc. Natl. Acad. Sci. U.S.A.* 1997, 94, 7192 (VEGF crystal structure).
Wiesmann, C. et al. *Cell* 1997, 91, 695 (crystal structure of VEGF with VEGFR1D2).

Methods:
Gill, S. et al. *Anal. Biochem.* 1989, 182, 319 (protein extinction coefficients from sequence).
Lee, H. et al. *J. Org. Chem.* 2001, 66, 3597 (APC synthesis).
Peterson, K. et al. *Anal. Biochem.* 2008, 378, 8 (VEGF FP assay).
Horne, S. et al. *J. Am. Chem. Soc.* 2007, 129, 4178; Price, J. et al. *J. Am. Chem. Soc.* 2010, 132, 12378 (CD signature of helical α/β-peptides).

What is claimed is:

1. A method of making peptidomimetic affinity reagents, the method comprising:
generating a Z-domain scaffold peptide having affinity recognition and/or binding to a desired target compound substituting at least one β-amino acid residue into at least one helical domain of the Z-domain scaffold peptide, thereby generating an α/β-peptide mimic of a Z-domain scaffold peptide.

2. The method of claim 1, wherein the at least one β-amino acid residue is cyclically constrained by a ring structure that incorporates alpha-position and beta-position carbon atoms of the β-amino acid residue.

3. The method of claim 1, wherein the Z-domain scaffold peptide comprises three helical domains designated helix 1, helix 2, and helix 3, and further comprising cleaving helix 3 from the α/β-peptide mimic, and wherein the at least one β-amino acid residue is substituted into helix 1 or helix 2.

4. The method claim 1, further comprising forming at least one disulfide bond between two residues in the α/β-peptide mimic.

5. The method of claim 1, wherein the unnatural α/β-peptide mimic of the Z-domain scaffold peptide is labeled.

6. A method of making peptidomimetic affinity reagents, the method comprising: generating an unnatural α/β-peptide mimic of a Z-domain scaffold comprising no more than 60 amino acid residues, and including at least one β-amino acid residue, and having specific affinity recognition and/or binding to a desired target compound.

7. The method of claim 6, further comprising incorporating into the α/β-peptide mimic of a Z-domain scaffold at least two amino acid residues that are capable of forming a disulfide bridge between them and forming a disulfide bond between the at least two amino acid residues.

8. The method of claim 6, wherein the at least one β-amino acid residue is cyclically constrained by a ring structure that incorporates alpha-position and beta-position carbon atoms of the β-amino acid residue.

9. The method of claim 6, wherein the α/β-peptide mimic of a Z-domain scaffold adopts three distinct helical domains in aqueous solution.

10. The method of claim 6, wherein the α/β-peptide mimic of a Z-domain scaffold has no more than 45 residues and adopts two distinct helical domains in aqueous solution.

11. The method of claim 6, wherein the unnatural α/β-peptide mimic of the Z-domain scaffold peptide is labeled.

12. A method of inhibiting proteolytic degradation of a Z-domain scaffold peptide, the method comprising providing an unnatural α/β-peptide mimic of the Z-domain scaffold peptide in which at least one α-amino acid residue present in the Z-domain scaffold peptide is replaced with at least one β-amino acid residue.

13. The method of claim 12, comprising providing an unnatural α/β-peptide mimic having at least three β-amino acid residues.

14. The method of claim 12, wherein the unnatural α/β-peptide mimic of the Z-domain scaffold peptide is labeled.

15. An unnatural α/β-peptide mimic of a Z-domain scaffold peptide, the α/β-peptide mimic comprising from 25 to 60 amino acid residues, having zero, one, two, or three distinct helical domains in aqueous solution, wherein at least one of the amino acid residues is a β-amino acid residue, and salts thereof.

16. The α/β-peptide mimic of a Z-domain scaffold of claim 15, wherein the α/β-peptide mimic of the Z-domain scaffold peptide is labeled.

17. The α/β-peptide mimic of a Z-domain scaffold of claim 15, conjugated, bound, or linked to a therapeutic agent.

18. An unnatural α/β-peptide mimic of a Z-domain scaffold peptide, the α/β-peptide mimic comprising no more than 45 amino acid residues, having no more than two distinct helical domains in aqueous solution, wherein at least one of the amino acid residues is a β-amino acid residue, and including at least one disulfide bond, and salts thereof.

19. The α/β-peptide mimic of a Z-domain scaffold of claim 18, wherein the α/β-peptide mimic of the Z-domain scaffold peptide is labeled.

20. The α/β-peptide mimic of a Z-domain scaffold of claim 18, wherein the at least one β-amino acid residue is a cyclically constrained β-amino acid residue.

21. The α/β-peptide mimic of a Z-domain scaffold of claim 18, conjugated, bound, or linked to a therapeutic agent.

22. A method of selectively delivering a therapeutic agent to a specific cell type or a specific tissue, the method comprising conjugating, binding, or linking the therapeutic agent to an α/β-peptide mimic of a Z-domain scaffold as recited in claim 15 to yield a mimic-agent conjugate, wherein the α/β-peptide mimic selectively binds to the specific cell type or the specific tissue, and then contacting the mimic-agent conjugate with the specific cell type or specific tissue.

23. The method of claim 22, wherein the α/β-peptide mimic selectively binds to a neoplastic cell.

* * * * *